US012762360B2

(12) United States Patent
Giobbi

(10) Patent No.: US 12,762,360 B2
(45) Date of Patent: Oct. 13, 2026

(54) PROXIMITY-BASED SYSTEM FOR OBJECT TRACKING AND AUTOMATIC APPLICATION INITIALIZATION

(71) Applicant: Proxense, LLC, Bend, OR (US)

(72) Inventor: John J. Giobbi, Bend, OR (US)

(73) Assignee: Proxense, LLC, Bend, OR (US)

( * ) Notice: Subject to any disclaimer, the term of this patent is extended or adjusted under 35 U.S.C. 154(b) by 41 days.

(21) Appl. No.: 18/756,469

(22) Filed: Jun. 27, 2024

(65) Prior Publication Data

US 2024/0386222 A1 Nov. 21, 2024

Related U.S. Application Data

(63) Continuation of application No. 17/372,189, filed on Jul. 9, 2021, now Pat. No. 12,056,558, which is a (Continued)

(51) Int. Cl.

*G06K 7/01* (2006.01)
*A61B 5/11* (2006.01)

(Continued)

(52) U.S. Cl.

CPC .............. *G06K 7/01* (2013.01); *A61B 5/1113* (2013.01); *G06K 7/10267* (2013.01);

(Continued)

(58) Field of Classification Search

None

See application file for complete search history.

(56) References Cited

U.S. PATENT DOCUMENTS 3,665,313 A 5/1972 Trent
3,739,329 A 6/1973 Lester (Continued)

FOREIGN PATENT DOCUMENTS

EP 1478152 A2 11/2004
EP 1536306 A1 6/2005

(Continued)

OTHER PUBLICATIONS

Malan, "Here come Wireless Sensors," Machine Design, Jun. 10, 2004, 3 pgs., archived at https://web.archive.org/web/20040610131354/http:/www.machinedesign.com/ASP/viewSelectedArticle.asp?strArticleId=56796&strSite=MDSite&Screen=CURRENTISSUE.

(Continued)

*Primary Examiner* — Muhammad Adnan

(74) *Attorney, Agent, or Firm* — Patent Law Works LLP

(57) ABSTRACT

A system and method provides for one or more of tracking of an object and providing automatic access to applications or data. Depending upon the embodiment, the system includes a personal digital key (PDK), a reader, a computing device and one or more of an auto login server and a tracking server. The PDK stores one or more profiles in memory. A reader is configured to wirelessly communicate with the PDK. The computing device is coupled to the reader and one or more of the auto login server and tracking server. The auto login server is configured to communicate with the reader and launches one or more applications associated with a user name identified by a profile received from the PDK. The tracking server is configured to communicate with the reader and to track and log information received from the PDK associated with the object.

20 Claims, 35 Drawing Sheets

Related U.S. Application Data continuation of application No. 16/247,111, filed on Jan. 14, 2019, now Pat. No. 11,132,882, which is a continuation of application No. 14/981,607, filed on Dec. 28, 2015, now Pat. No. 10,217,339, which is a continuation of application No. 13/401,702, filed on Feb. 21, 2012, now Pat. No. 9,265,450.

(60) Provisional application No. 61/445,035, filed on Feb. 21, 2011.

(51) Int. Cl.
*G01V 15/00* (2006.01)
*G06K 7/10* (2006.01)
*G06K 19/07* (2006.01)
*G08B 13/24* (2006.01)

(52) U.S. Cl.
CPC ..... *G06K 7/10356* (2013.01); *G06K 19/0718* (2013.01); *G08B 13/2462* (2013.01); *G01V 15/00* (2013.01)

(56) References Cited

U.S. PATENT DOCUMENTS 3,761,883 A 9/1973 Alvarez et al.
3,906,166 A 9/1975 Cooper et al.
4,101,873 A 7/1978 Anderson et al.
4,430,705 A 2/1984 Cannavino et al.
4,476,469 A 10/1984 Lander
4,598,272 A 7/1986 Cox
4,661,821 A 4/1987 Smith
4,736,094 A 4/1988 Yoshida
4,759,060 A 7/1988 Hayashi et al.
4,814,742 A 3/1989 Morita et al.
4,871,997 A 10/1989 Adriaenssens et al.
4,993,068 A 2/1991 Piosenka et al.
5,043,702 A 8/1991 Kuo
5,052,049 A 9/1991 Andros et al.
5,187,352 A 2/1993 Blair et al.
5,212,369 A 5/1993 Karlisch et al.
5,224,164 A 6/1993 Elsner
5,296,641 A 3/1994 Stelzel
5,307,349 A 4/1994 Shloss et al.
5,317,572 A 5/1994 Satoh
5,325,285 A 6/1994 Araki
5,392,287 A 2/1995 Tiedemann et al.
5,392,433 A 2/1995 Hammersley et al.
5,410,588 A 4/1995 Ito
5,416,780 A 5/1995 Patel
5,422,632 A 6/1995 Bucholtz et al.
5,428,684 A 6/1995 Akiyama et al.
5,450,489 A 9/1995 Ostrover et al.
5,473,690 A 12/1995 Grimonprez et al.
5,481,265 A 1/1996 Russell
5,506,863 A 4/1996 Meidan et al.
5,517,502 A 5/1996 Bestler et al.
5,530,232 A 6/1996 Taylor
5,541,583 A 7/1996 Mandelbaum
5,544,321 A 8/1996 Theimer et al.
5,552,776 A 9/1996 Wade et al.
5,563,947 A 10/1996 Kikinis
5,578,808 A 11/1996 Taylor
5,589,838 A 12/1996 Mcewan
5,594,227 A 1/1997 Deo
5,598,474 A 1/1997 Johnson
5,611,050 A 3/1997 Theimer et al.
5,615,277 A 3/1997 Hoffman
5,619,251 A 4/1997 Kuroiwa et al.
5,623,552 A 4/1997 Lane
5,629,980 A 5/1997 Stefik et al.
5,644,354 A 7/1997 Thompson et al.
5,666,412 A 9/1997 Handelman et al.
5,689,529 A 11/1997 Johnson
5,692,049 A 11/1997 Johnson et al.
5,708,423 A * 1/1998 Ghaffari ............ G08B 13/2471 340/5.8
5,719,387 A 2/1998 Fujioka
5,729,237 A 3/1998 Webb
5,760,705 A 6/1998 Glessner et al.
5,760,744 A 6/1998 Sauer
5,773,954 A 6/1998 Vanhorn
5,784,464 A 7/1998 Akiyama et al.
5,799,085 A 8/1998 Shona
5,821,854 A 10/1998 Dorinski et al.
5,825,876 A 10/1998 Peterson, Jr.
5,835,595 A 11/1998 Fraser et al.
5,838,306 A 11/1998 O'Connor et al.
5,854,891 A 12/1998 Postlewaite et al.
5,857,020 A 1/1999 Peterson, Jr.
5,886,634 A 3/1999 Muhme
5,892,825 A 4/1999 Mages et al.
5,892,900 A 4/1999 Ginter et al.
5,894,551 A 4/1999 Huggins et al.
5,898,880 A 4/1999 Ryu
5,910,776 A 6/1999 Black
5,917,913 A 6/1999 Wang
5,923,757 A 7/1999 Hocker et al.
5,928,327 A 7/1999 Wang et al.
5,942,985 A 8/1999 Chin
5,991,399 A 11/1999 Graunke et al.
5,991,749 A 11/1999 Morrill, Jr.
6,009,333 A 12/1999 Chaco
6,016,476 A 1/2000 Maes et al.
6,018,739 A 1/2000 Mccoy et al.
6,025,780 A 2/2000 Bowers et al.
6,035,038 A 3/2000 Campinos et al.
6,035,329 A 3/2000 Mages et al.
6,038,334 A 3/2000 Hamid
6,038,549 A 3/2000 Davis et al.
6,038,666 A 3/2000 Hsu et al.
6,040,786 A 3/2000 Fujioka
6,041,410 A 3/2000 Hsu et al.
6,042,006 A 3/2000 Van Tilburg et al.
6,044,470 A 3/2000 Kuriyama
6,045,039 A 4/2000 Stinson et al.
6,052,468 A 4/2000 Hillhouse
6,055,314 A 4/2000 Spies et al.
6,068,184 A 5/2000 Barnett
6,069,647 A 5/2000 Sullivan et al.
6,070,796 A 6/2000 Sirbu
6,076,164 A 6/2000 Tanaka et al.
6,088,450 A 7/2000 Davis et al.
6,088,730 A 7/2000 Kato et al.
6,104,290 A 8/2000 Naguleswaran
6,104,334 A 8/2000 Allport
6,110,041 A 8/2000 Walker et al.
6,121,544 A 9/2000 Petsinger
6,134,283 A 10/2000 Sands et al.
6,137,480 A 10/2000 Shintani
6,138,010 A 10/2000 Rabe et al.
6,148,142 A 11/2000 Anderson
6,148,210 A 11/2000 Elwin et al.
6,161,179 A 12/2000 Seidel
6,175,921 B1 1/2001 Rosen
6,177,887 B1 1/2001 Jerome
6,185,316 B1 2/2001 Buffam
6,189,105 B1 2/2001 Lopes
6,209,089 B1 3/2001 Selitrennikoff et al.
6,219,109 B1 4/2001 Raynesford et al.
6,219,439 B1 4/2001 Burger
6,219,553 B1 4/2001 Panasik
6,237,848 B1 5/2001 Everett
6,240,076 B1 5/2001 Kanerva et al.
6,247,130 B1 6/2001 Fritsch
6,249,869 B1 6/2001 Drupsteen et al.
6,250,557 B1 6/2001 Forslund et al.
6,256,737 B1 7/2001 Bianco et al.
6,266,415 B1 7/2001 Campinos et al.
6,270,011 B1 8/2001 Gottfried
6,279,111 B1 8/2001 Jensenworth et al.
6,279,146 B1 8/2001 Evans et al.
6,295,057 B1 9/2001 Rosin et al.
6,307,471 B1 10/2001 Xydis

(56) References Cited

U.S. PATENT DOCUMENTS 6,317,755 B1 11/2001 Rakers et al.
6,325,285 B1 12/2001 Baratelli
6,336,121 B1 1/2002 Lyson et al.
6,336,142 B1 1/2002 Kato et al.
6,343,280 B2 1/2002 Clark
6,345,347 B1 2/2002 Biran
6,363,485 B1 3/2002 Adams et al.
6,367,019 B1 4/2002 Ansell et al.
6,369,693 B1 4/2002 Gibson
6,370,376 B1 4/2002 Sheath
6,381,029 B1 4/2002 Tipirneni
6,381,747 B1 4/2002 Wonfor et al.
6,385,596 B1 5/2002 Wiser et al.
6,392,664 B1 5/2002 White et al.
6,397,387 B1 5/2002 Rosin et al.
6,401,059 B1 6/2002 Shen et al.
6,411,307 B1 6/2002 Rosin et al.
6,424,249 B1 7/2002 Houvener
6,424,715 B1 7/2002 Saito
6,425,084 B1 7/2002 Rallis et al.
6,434,403 B1 8/2002 Ausems et al.
6,434,535 B1 8/2002 Kupka et al.
6,446,004 B1 9/2002 Cao et al.
6,446,130 B1 9/2002 Grapes
6,456,958 B1 9/2002 Xydis
6,463,534 B1 10/2002 Geiger et al.
6,480,101 B1 11/2002 Kelly et al.
6,480,188 B1 11/2002 Horsley
6,484,182 B1 11/2002 Dunphy et al.
6,484,260 B1 11/2002 Scott et al.
6,484,946 B2 11/2002 Matsumoto et al.
6,487,663 B1 11/2002 Jaisimha et al.
6,490,443 B1 12/2002 Freeny, Jr.
6,510,350 B1 1/2003 Steen et al.
6,522,253 B1 2/2003 Saltus
6,523,113 B1 2/2003 Wehrenberg
6,529,949 B1 3/2003 Getsin et al.
6,546,418 B2 4/2003 Schena et al.
6,550,011 B1 4/2003 Sims, III
6,563,465 B2 5/2003 Frecska
6,563,805 B1 5/2003 Ma et al.
6,564,380 B1 5/2003 Murphy
6,577,238 B1 6/2003 Whitesmith et al.
6,593,887 B2 7/2003 Luk et al.
6,597,680 B1 7/2003 Lindskog et al.
6,607,136 B1 8/2003 Atsmon et al.
6,621,528 B1 9/2003 Kessler et al.
6,624,752 B2 9/2003 Klitsgaard et al.
6,628,302 B2 9/2003 White et al.
6,632,992 B2 10/2003 Hasegawa
6,633,981 B1 10/2003 Davis
6,645,077 B2 11/2003 Rowe
6,647,417 B1 11/2003 Hunter et al.
6,657,538 B1 12/2003 Ritter
6,658,566 B1 12/2003 Hazard
6,667,684 B1 12/2003 Waggamon et al.
6,669,096 B1 12/2003 Saphar et al.
6,671,808 B1 12/2003 Abbott et al.
6,683,954 B1 1/2004 Searle
6,695,207 B1 2/2004 Norris, Jr.
6,697,944 B1 2/2004 Jones et al.
6,709,333 B1 3/2004 Bradford et al.
6,711,464 B1 3/2004 Yap et al.
6,714,168 B2 3/2004 Berenbaum
6,715,246 B1 4/2004 Frecska et al.
6,728,397 B2 4/2004 Mcneal
6,737,955 B2 5/2004 Ghabra et al.
6,738,772 B2 5/2004 Regelski et al.
6,758,394 B2 7/2004 Maskatiya et al.
6,771,969 B1 8/2004 Chinoy et al.
6,775,655 B1 8/2004 Peinado et al.
6,785,474 B2 8/2004 Hirt et al.
6,788,640 B2 9/2004 Celeste
6,788,924 B1 9/2004 Knutson et al.
6,795,425 B1 9/2004 Raith
6,804,825 B1 10/2004 White et al.
6,806,887 B2 10/2004 Chernock et al.
6,819,219 B1 11/2004 Bolle et al.
6,839,542 B2 1/2005 Sibecas et al.
6,839,772 B1 1/2005 Kowalski et al.
6,850,147 B2 2/2005 Prokoski et al.
6,853,988 B1 2/2005 Dickinson et al.
6,859,812 B1 2/2005 Poynor
6,861,980 B1 3/2005 Rowitch et al.
6,871,063 B1 3/2005 Schiffer
6,873,975 B1 3/2005 Hatakeyama et al.
6,879,567 B2 4/2005 Callaway et al.
6,879,966 B1 4/2005 Lapsley et al.
6,886,741 B1 5/2005 Salveson
6,889,067 B2 5/2005 Willey
6,891,822 B1 5/2005 Gubbi et al.
6,892,307 B1 5/2005 Wood et al.
6,930,643 B2 8/2005 Byrne et al.
6,934,855 B1 8/2005 Kipnis et al.
6,947,003 B2 9/2005 Huor
6,950,941 B1 9/2005 Lee et al.
6,957,086 B2 10/2005 Bahl et al.
6,961,858 B2 11/2005 Fransdonk
6,963,270 B1 11/2005 Gallagher et al.
6,963,971 B1 11/2005 Bush et al.
6,973,576 B2 12/2005 Giobbi
6,975,202 B1 12/2005 Rodriguez et al.
6,980,087 B2 12/2005 Zukowski
6,983,882 B2 1/2006 Cassone
6,999,032 B2 2/2006 Pakray et al.
7,012,503 B2 3/2006 Nielsen
7,020,635 B2 3/2006 Hamilton et al.
7,020,785 B2 3/2006 Kim et al.
7,031,945 B1 4/2006 Donner
7,049,963 B2 5/2006 Waterhouse et al.
7,055,171 B1 5/2006 Martin et al.
7,058,806 B2 6/2006 Smeets et al.
7,061,380 B1 6/2006 Orlando et al.
7,068,623 B1 6/2006 Barany et al.
7,072,900 B2 7/2006 Sweitzer et al.
7,079,079 B2 7/2006 Jo et al.
7,080,049 B2 7/2006 Truitt et al.
7,082,415 B1 7/2006 Robinson et al.
7,090,126 B2 8/2006 Kelly et al.
7,090,128 B2 8/2006 Farley et al.
7,100,053 B1 8/2006 Brown et al.
7,107,455 B1 9/2006 Merkin
7,107,462 B2 9/2006 Fransdonk
7,111,789 B2 9/2006 Rajasekaran et al.
7,112,138 B2 9/2006 Hedrick et al.
7,119,659 B2 10/2006 Bonalle et al.
7,123,149 B2 10/2006 Nowak et al.
7,130,668 B2 10/2006 Chang et al.
7,131,139 B1 10/2006 Meier
7,137,008 B1 11/2006 Hamid et al.
7,137,012 B1 11/2006 Kamibayashi et al.
7,139,914 B2 11/2006 Arnouse
7,150,045 B2 12/2006 Koelle et al.
7,155,416 B2 12/2006 Shatford
7,159,114 B1 1/2007 Zajkowski et al.
7,159,765 B2 1/2007 Frerking
7,167,987 B2 1/2007 Angelo
7,168,089 B2 1/2007 Nguyen et al.
7,176,797 B2 2/2007 Zai et al.
7,185,363 B1 2/2007 Narin et al.
7,188,110 B1 3/2007 Ludtke et al.
7,191,466 B1 3/2007 Hamid et al.
7,194,438 B2 3/2007 Sovio et al.
7,209,955 B1 4/2007 Major et al.
7,218,944 B2 5/2007 Cromer et al.
7,225,161 B2 5/2007 Lam et al.
7,230,908 B2 6/2007 Vanderaar et al.
7,231,068 B2 6/2007 Tibor
7,231,451 B2 6/2007 Law et al.
7,239,226 B2 7/2007 Berardi et al.
7,239,241 B2 7/2007 Claudatos et al.
7,242,923 B2 7/2007 Perera et al.
7,245,221 B2 7/2007 Claudatos et al.
7,249,177 B1 7/2007 Miller

(56) References Cited

U.S. PATENT DOCUMENTS 7,272,723 B1 9/2007 Abbott et al.
7,277,737 B1 10/2007 Vollmer et al.
7,278,025 B2 10/2007 Saito et al.
7,283,650 B1 10/2007 Sharma et al.
7,295,106 B1 11/2007 Jackson et al.
7,295,119 B2 11/2007 Rappaport et al.
7,305,560 B2 12/2007 Giobbi
7,310,042 B2 12/2007 Seifert
7,314,164 B2 1/2008 Bonalle et al.
7,317,799 B2 1/2008 Hammersmith et al.
7,319,395 B2 1/2008 Puzio et al.
7,323,991 B1 1/2008 Eckert et al.
7,330,108 B2 2/2008 Thomas
7,333,002 B2 2/2008 Bixler et al.
7,333,615 B1 2/2008 Jarboe et al.
7,336,181 B2 2/2008 Nowak et al.
7,336,182 B1 2/2008 Baranowski et al.
7,337,326 B2 2/2008 Palmer et al.
7,341,181 B2 3/2008 Bonalle et al.
7,342,503 B1 3/2008 Light et al.
7,349,557 B2 3/2008 Tibor
7,356,393 B1 4/2008 Schlatre et al.
7,356,706 B2 4/2008 Scheurich
7,361,919 B2 4/2008 Setlak
7,363,494 B2 4/2008 Brainard et al.
7,370,366 B2 5/2008 Lacan et al.
7,378,939 B2 5/2008 Sengupta et al.
7,380,202 B1 5/2008 Lindhorst et al.
7,382,799 B1 6/2008 Young et al.
7,387,235 B2 6/2008 Gilbert et al.
7,401,731 B1 7/2008 Pletz et al.
7,404,088 B2 7/2008 Giobbi
7,408,799 B1 8/2008 Kang
7,424,134 B2 9/2008 Chou
7,437,330 B1 10/2008 Robinson et al.
7,443,297 B1 * 10/2008 Baranowski ....... G08B 13/1436
340/572.1
7,447,911 B2 11/2008 Chou et al.
7,448,087 B2 11/2008 Ohmori et al.
7,458,510 B1 12/2008 Zhou
7,460,836 B2 12/2008 Smith et al.
7,461,444 B2 12/2008 Deaett et al.
7,464,053 B1 12/2008 Pylant
7,464,059 B1 12/2008 Robinson et al.
7,466,232 B2 12/2008 Neuwirth
7,472,280 B2 12/2008 Giobbi
7,477,285 B1 1/2009 Johnson
7,512,806 B2 3/2009 Lemke
7,525,413 B2 4/2009 Jung et al.
7,529,944 B2 5/2009 Hamid
7,533,809 B1 5/2009 Robinson et al.
7,545,312 B2 6/2009 Kiang et al.
7,552,872 B2 6/2009 Tokita et al.
7,565,329 B2 7/2009 Lapsley et al.
7,573,382 B2 8/2009 Choubey et al.
7,573,841 B2 8/2009 Lee et al.
7,574,734 B2 8/2009 Fedronic et al.
7,578,442 B2 8/2009 Knowles et al.
7,583,238 B2 9/2009 Cassen et al.
7,583,643 B2 9/2009 Smith et al.
7,587,502 B2 9/2009 Crawford et al.
7,587,611 B2 9/2009 Johnson et al.
7,594,611 B1 9/2009 Arrington, III
7,595,765 B1 9/2009 Hirsch et al.
7,603,564 B2 10/2009 Adachi
7,606,733 B2 10/2009 Shmueli et al.
7,617,523 B2 11/2009 Das et al.
7,620,184 B2 11/2009 Marque Pucheu
7,624,073 B1 11/2009 Robinson et al.
7,624,417 B2 11/2009 Dua
7,640,273 B2 12/2009 Wallmeier et al.
7,644,043 B2 1/2010 Minowa
7,644,443 B2 1/2010 Matsuyama et al.
7,646,307 B2 1/2010 Plocher et al.
7,652,892 B2 1/2010 Shiu et al.
7,653,883 B2 1/2010 Hotelling et al.
7,676,380 B2 3/2010 Graves et al.
7,681,050 B2 3/2010 Blom et al.
7,689,005 B2 3/2010 Wang et al.
7,701,858 B2 4/2010 Werb et al.
7,706,896 B2 4/2010 Music et al.
7,711,152 B1 5/2010 Davida et al.
7,711,586 B2 5/2010 Aggarwal et al.
7,715,593 B1 5/2010 Adams et al.
7,724,713 B2 5/2010 Del Prado Pavon et al.
7,724,717 B2 5/2010 Porras et al.
7,724,720 B2 5/2010 Korpela et al.
7,726,566 B2 6/2010 Brown et al.
7,734,476 B2 6/2010 Wildman et al.
7,764,236 B2 7/2010 Hill et al.
7,765,164 B1 7/2010 Robinson et al.
7,765,181 B2 7/2010 Thomas et al.
7,766,243 B2 8/2010 Adams et al.
7,768,960 B1 8/2010 Barratt
7,773,754 B2 8/2010 Buer et al.
7,774,613 B2 8/2010 Lemke
7,780,082 B2 8/2010 Handa et al.
7,796,551 B1 9/2010 Machiraju et al.
7,813,822 B1 10/2010 Hoffberg
7,865,448 B2 1/2011 Pizarro
7,865,937 B1 1/2011 White et al.
7,883,003 B2 2/2011 Giobbi et al.
7,883,417 B2 2/2011 Bruzzese et al.
7,904,718 B2 3/2011 Giobbi et al.
7,943,868 B2 5/2011 Anders et al.
7,957,536 B2 6/2011 Nolte
7,961,078 B1 6/2011 Reynolds et al.
7,984,064 B2 7/2011 Fusari
7,996,514 B2 8/2011 Baumert et al.
8,011,588 B2 9/2011 Kon et al.
8,026,821 B2 9/2011 Reeder et al.
8,036,152 B2 10/2011 Brown et al.
8,041,582 B2 10/2011 Godschall et al.
8,049,594 B1 11/2011 Baranowski
8,077,041 B2 12/2011 Stern et al.
8,081,215 B2 12/2011 Kuo et al.
8,082,160 B2 12/2011 Collins et al.
8,089,354 B2 1/2012 Perkins
8,112,066 B2 2/2012 Ben Ayed
8,117,125 B1 2/2012 Kawan et al.
8,125,624 B2 2/2012 Jones et al.
8,135,624 B1 3/2012 Ramalingam et al.
8,171,528 B1 5/2012 Brown
8,193,923 B2 6/2012 Rork et al.
8,200,980 B1 6/2012 Robinson et al.
8,215,552 B1 7/2012 Rambadt
8,219,129 B2 7/2012 Brown et al.
8,248,263 B2 8/2012 Shervey et al.
8,258,942 B1 9/2012 Lanzone et al.
8,284,748 B2 * 10/2012 Borghei ................ H04W 8/186
455/457
8,294,554 B2 10/2012 Shoarinejad et al.
8,296,573 B2 10/2012 Bolle et al.
8,307,414 B2 11/2012 Zerfos et al.
8,325,011 B2 12/2012 Butler et al.
8,327,151 B2 12/2012 Awatsu et al.
8,333,317 B2 12/2012 Buer et al.
8,340,672 B2 12/2012 Brown et al.
8,352,730 B2 1/2013 Giobbi
8,373,562 B1 * 2/2013 Heinze .................. G06Q 10/06
340/572.1
8,387,124 B2 2/2013 Smetters et al.
8,390,456 B2 3/2013 Puleston et al.
8,395,484 B2 3/2013 Fullerton
8,410,906 B1 4/2013 Dacus et al.
8,412,949 B2 4/2013 Giobbi et al.
8,417,643 B2 4/2013 Mardikar
8,421,606 B2 4/2013 Collins et al.
8,424,079 B2 4/2013 Adams et al.
8,432,262 B2 4/2013 Talty et al.
8,433,919 B2 4/2013 Giobbi et al.
8,448,858 B1 5/2013 Kundu et al.
8,457,672 B2 6/2013 Brown et al.
8,467,969 B2 6/2013 Nielsen et al.

(56) References Cited

U.S. PATENT DOCUMENTS 8,473,748 B2 6/2013 Sampas
8,484,696 B2 7/2013 Gatto et al.
8,494,576 B1 7/2013 Bye et al.
8,508,336 B2 8/2013 Giobbi et al.
8,511,555 B2 8/2013 Babcock et al.
8,519,823 B2 8/2013 Rinkes
8,522,019 B2 8/2013 Michaelis
8,558,699 B2 10/2013 Butler et al.
8,572,391 B2 10/2013 Golan et al.
8,577,091 B2 11/2013 Ivanov et al.
8,600,674 B1 12/2013 Barbeau et al.
8,646,042 B1 2/2014 Brown
8,659,427 B2 2/2014 Brown et al.
8,678,273 B2 3/2014 Mcneal
8,717,346 B2 5/2014 Claessen
8,738,925 B1 5/2014 Park et al.
8,799,574 B2 8/2014 Corda
8,838,993 B2 9/2014 Giobbi et al.
8,856,539 B2 10/2014 Weiss
8,857,716 B1 10/2014 Giobbi et al.
8,886,954 B1 11/2014 Giobbi
8,907,861 B2 12/2014 Hirt
8,914,477 B2 12/2014 Gammon
8,918,854 B1 12/2014 Giobbi
8,931,698 B2 1/2015 Ishikawa et al.
8,977,860 B2 3/2015 Barrus et al.
8,979,646 B2 3/2015 Moser et al.
9,020,854 B2 4/2015 Giobbi
9,024,719 B1 5/2015 Saunders
9,037,140 B1 5/2015 Brown
9,042,819 B2 5/2015 Dua
9,049,188 B1 6/2015 Brown
9,098,954 B1 * 8/2015 Byrd ...................... G06V 20/52
9,113,464 B2 8/2015 Brown et al.
9,165,233 B2 10/2015 Testanero
9,189,788 B1 11/2015 Robinson et al.
9,208,300 B2 12/2015 Chastain et al.
9,230,399 B2 1/2016 Yacenda
9,235,700 B1 1/2016 Brown
9,251,326 B2 2/2016 Giobbi et al.
9,251,332 B2 2/2016 Giobbi
9,265,043 B2 2/2016 Brown et al.
9,265,450 B1 2/2016 Giobbi
9,269,221 B2 2/2016 Brown et al.
9,276,914 B2 3/2016 Woodward et al.
9,298,905 B1 3/2016 Giobbi
9,305,312 B2 4/2016 Kountotsis et al.
9,322,974 B1 4/2016 Giobbi
9,405,898 B2 8/2016 Giobbi
9,418,205 B2 8/2016 Giobbi
9,430,624 B1 8/2016 Mortensen et al.
9,450,956 B1 9/2016 Giobbi
9,542,542 B2 1/2017 Giobbi et al.
9,613,483 B2 4/2017 Giobbi
9,679,289 B1 6/2017 Brown
9,728,080 B1 8/2017 Giobbi et al.
9,807,091 B2 10/2017 Giobbi
9,830,504 B2 11/2017 Masood et al.
9,892,250 B2 2/2018 Giobbi
9,898,662 B2 2/2018 Tsuda et al.
9,904,816 B1 2/2018 Giobbi et al.
9,990,628 B2 6/2018 Giobbi
10,026,253 B2 7/2018 Giobbi
10,073,960 B1 9/2018 Brown
10,104,062 B2 10/2018 Chastain et al.
10,110,385 B1 10/2018 Rush et al.
10,140,073 B2 11/2018 Chang et al.
10,171,460 B2 1/2019 Giobbi
10,217,339 B1 2/2019 Giobbi
10,229,294 B1 3/2019 Giobbi et al.
10,303,867 B2 5/2019 Schrder
10,313,336 B2 6/2019 Giobbi
10,334,541 B1 6/2019 Brown
10,341,483 B2 * 7/2019 Dods ......................... G01T 7/00
10,362,483 B2 7/2019 Frusina
10,374,795 B1 8/2019 Giobbi et al.
10,383,112 B2 8/2019 Brown et al.
10,403,128 B2 9/2019 Giobbi et al.
10,405,181 B2 9/2019 Li et al.
10,437,976 B2 10/2019 Giobbi
10,455,533 B2 10/2019 Brown
10,469,456 B1 11/2019 Giobbi
10,567,965 B2 2/2020 Boettcher et al.
10,572,700 B2 * 2/2020 Sengstaken, Jr. ........ G08B 7/06
10,579,997 B2 3/2020 Sibert et al.
10,698,989 B2 6/2020 Giobbi
10,755,300 B2 8/2020 Goodhart et al.
10,764,044 B1 9/2020 Giobbi et al.
10,769,939 B2 9/2020 Brown et al.
10,778,670 B2 9/2020 Chastain et al.
10,817,964 B2 10/2020 Guillama et al.
10,856,148 B2 12/2020 Li et al.
10,902,723 B2 * 1/2021 Doyle, III ................ G08G 1/20
10,909,229 B2 2/2021 Giobbi
10,929,869 B2 2/2021 Rosenberg
10,943,471 B1 3/2021 Giobbi et al.
11,086,979 B1 8/2021 Giobbi
11,212,797 B2 12/2021 Brown et al.
11,219,022 B2 1/2022 Brown et al.
11,562,644 B2 1/2023 Brown et al.
11,914,695 B2 2/2024 Giobbi
12,373,538 B2 7/2025 Giobbi
2001/0000535 A1 4/2001 Lapsley et al.
2001/0011276 A1 8/2001 Durst et al.
2001/0014885 A1 8/2001 Yanagi
2001/0018763 A1 8/2001 Ikeda et al.
2001/0021950 A1 9/2001 Hawley et al.
2001/0024428 A1 9/2001 Onouchi
2001/0026619 A1 10/2001 Howard et al.
2001/0027121 A1 10/2001 Boesen
2001/0027439 A1 10/2001 Holtzman et al.
2001/0034659 A1 10/2001 Kobayashi
2001/0036297 A1 11/2001 Ikegami et al.
2001/0044337 A1 11/2001 Rowe et al.
2002/0004783 A1 1/2002 Paltenghe et al.
2002/0007456 A1 1/2002 Peinado et al.
2002/0010679 A1 1/2002 Felsher
2002/0013772 A1 1/2002 Peinado
2002/0014954 A1 2/2002 Fitzgibbon et al.
2002/0015008 A1 2/2002 Kishida et al.
2002/0015494 A1 2/2002 Nagai et al.
2002/0019811 A1 2/2002 Lapsley et al.
2002/0022455 A1 2/2002 Salokannel et al.
2002/0023032 A1 2/2002 Pearson et al.
2002/0023217 A1 2/2002 Wheeler et al.
2002/0026424 A1 2/2002 Akashi
2002/0037732 A1 3/2002 Gous et al.
2002/0046336 A1 4/2002 Kon et al.
2002/0049806 A1 4/2002 Gatz et al.
2002/0052193 A1 5/2002 Chetty
2002/0055908 A1 5/2002 Di Giorgio et al.
2002/0056043 A1 5/2002 Glass
2002/0059114 A1 5/2002 Cockrill et al.
2002/0062249 A1 5/2002 Iannacci
2002/0064074 A1 5/2002 Kamise et al.
2002/0065778 A1 5/2002 Bouet et al.
2002/0068605 A1 6/2002 Stanley
2002/0069364 A1 6/2002 Dosch
2002/0071416 A1 6/2002 Carlson et al.
2002/0071559 A1 6/2002 Christensen et al.
2002/0073042 A1 6/2002 Maritzen et al.
2002/0073293 A1 6/2002 Mac et al.
2002/0076051 A1 6/2002 Nii
2002/0078367 A1 6/2002 Lang et al.
2002/0080969 A1 6/2002 Giobbi
2002/0083178 A1 6/2002 Brothers
2002/0083318 A1 6/2002 Larose
2002/0086690 A1 7/2002 Takahashi et al.
2002/0089890 A1 7/2002 Fibranz et al.
2002/0091562 A1 7/2002 Siegel et al.
2002/0091646 A1 7/2002 Lake et al.
2002/0095586 A1 7/2002 Doyle et al.
2002/0095587 A1 7/2002 Doyle et al.
2002/0097876 A1 7/2002 Harrison

(56) References Cited

U.S. PATENT DOCUMENTS

2002/0098888 A1 7/2002 Rowe et al.
2002/0100798 A1 8/2002 Farrugia et al.
2002/0103027 A1 8/2002 Rowe et al.
2002/0103881 A1 8/2002 Granade et al.
2002/0104006 A1 8/2002 Boate et al.
2002/0104019 A1 8/2002 Chatani et al.
2002/0105918 A1 8/2002 Yamada et al.
2002/0108049 A1 8/2002 Xu et al.
2002/0109580 A1 8/2002 Shreve et al.
2002/0111919 A1 8/2002 Weller et al.
2002/0112183 A1 8/2002 Baird et al.
2002/0115444 A1 8/2002 Yu et al.
2002/0116615 A1 8/2002 Nguyen et al.
2002/0124251 A1 9/2002 Hunter et al.
2002/0128017 A1 9/2002 Virtanen
2002/0128057 A1 9/2002 Walker et al.
2002/0129262 A1 9/2002 Kutaragi et al.
2002/0138438 A1 9/2002 Bardwell
2002/0138445 A1 9/2002 Laage et al.
2002/0138767 A1 9/2002 Hamid et al.
2002/0138768 A1 9/2002 Murakami et al.
2002/0139848 A1 10/2002 Catan
2002/0140542 A1 10/2002 Prokoski et al.
2002/0141586 A1 10/2002 Margalit et al.
2002/0143623 A1 10/2002 Dayley
2002/0143634 A1 10/2002 Kumar et al.
2002/0143655 A1 10/2002 Elston et al.
2002/0144116 A1 10/2002 Giobbi
2002/0144117 A1 10/2002 Faigle
2002/0146347 A1 10/2002 McNeil
2002/0147653 A1 10/2002 Shmueli et al.
2002/0147658 A1 10/2002 Kwan
2002/0147912 A1 10/2002 Shmueli et al.
2002/0148892 A1 10/2002 Bardwell
2002/0150282 A1 10/2002 Kinsella
2002/0152391 A1 10/2002 Willins et al.
2002/0153996 A1 10/2002 Chan et al.
2002/0158121 A1 10/2002 Stanford-Clark
2002/0158750 A1 10/2002 Almalik
2002/0158765 A1 10/2002 Pape et al.
2002/0160820 A1 10/2002 Winkler
2002/0162009 A1 10/2002 Shmueli et al.
2002/0165803 A1 11/2002 Iwase et al.
2002/0174348 A1 11/2002 Ting
2002/0177460 A1 11/2002 Beasley et al.
2002/0178063 A1 11/2002 Gravelle et al.
2002/0184208 A1 12/2002 Kato
2002/0187746 A1 12/2002 Cheng et al.
2002/0191816 A1 12/2002 Maritzen et al.
2002/0196963 A1 12/2002 Bardwell
2002/0199120 A1 12/2002 Schmidt
2003/0001016 A1 1/2003 Fraier et al.
2003/0018522 A1 1/2003 Denimarck et al.
2003/0022701 A1 1/2003 Gupta
2003/0023882 A1 1/2003 Udom
2003/0024975 A1 2/2003 Rajasekharan
2003/0033203 A1 2/2003 Inoue et al.
2003/0034877 A1 2/2003 Miller et al.
2003/0036416 A1 2/2003 Pattabiraman et al.
2003/0036425 A1 2/2003 Kaminkow et al.
2003/0044050 A1 3/2003 Clark et al.
2003/0046228 A1 3/2003 Berney
2003/0046237 A1 3/2003 Uberti
2003/0046552 A1 3/2003 Hamid
2003/0048174 A1 3/2003 Stevens et al.
2003/0051173 A1 3/2003 Krueger
2003/0054868 A1 3/2003 Paulsen et al.
2003/0054881 A1 3/2003 Hedrick et al.
2003/0055689 A1 3/2003 Block et al.
2003/0055792 A1 3/2003 Kinoshita et al.
2003/0061154 A1 3/2003 Chacko
2003/0061172 A1 3/2003 Robinson
2003/0063619 A1 4/2003 Montano et al.
2003/0074575 A1 4/2003 Hoberock et al.
2003/0079133 A1 4/2003 Breiter et al.
2003/0087601 A1 5/2003 Agam et al.
2003/0088441 A1 5/2003 Mcnerney
2003/0105719 A1 6/2003 Berger et al.
2003/0109274 A1 6/2003 Budka et al.
2003/0115227 A1 6/2003 Guthery
2003/0115351 A1 6/2003 Giobbi
2003/0115473 A1 6/2003 Sugimura et al.
2003/0115474 A1 6/2003 Khan et al.
2003/0117969 A1 6/2003 Koo et al.
2003/0117980 A1 6/2003 Kim et al.
2003/0120934 A1 6/2003 Ortiz
2003/0127511 A1 7/2003 Kelly et al.
2003/0128866 A1 7/2003 Mcneal
2003/0137404 A1 7/2003 Bonneau et al.
2003/0139190 A1 7/2003 Steelberg et al.
2003/0140221 A1 7/2003 Garnett
2003/0142041 A1 7/2003 Barlow et al.
2003/0146835 A1 8/2003 Carter
2003/0149744 A1 8/2003 Bierre et al.
2003/0152059 A1 8/2003 Odman
2003/0156742 A1 8/2003 Witt et al.
2003/0159040 A1 8/2003 Hashimoto et al.
2003/0163388 A1 8/2003 Beane
2003/0167207 A1 9/2003 Berardi et al.
2003/0169697 A1 9/2003 Suzuki et al.
2003/0172028 A1 9/2003 Abell et al.
2003/0172037 A1 9/2003 Jung et al.
2003/0174690 A1 9/2003 Benveniste
2003/0174839 A1 9/2003 Yamagata et al.
2003/0176218 A1 9/2003 Lemay et al.
2003/0177102 A1 9/2003 Robinson
2003/0186739 A1 10/2003 Paulsen et al.
2003/0187787 A1 10/2003 Freund
2003/0189092 A1 10/2003 Takano
2003/0195842 A1 10/2003 Reece
2003/0196084 A1 10/2003 Okereke et al.
2003/0199267 A1 10/2003 Iwasa et al.
2003/0200152 A1 10/2003 Divekar
2003/0204526 A1 10/2003 Salehi-Had
2003/0204721 A1 10/2003 Barrus et al.
2003/0213840 A1 11/2003 Livingston et al.
2003/0218533 A1 11/2003 Flick
2003/0223394 A1 12/2003 Parantainen et al.
2003/0225703 A1 12/2003 Angel
2003/0226031 A1 12/2003 Proudler et al.
2003/0227382 A1* 12/2003 Breed ................ G08B 13/2462
340/568.1
2003/0233458 A1 12/2003 Kwon et al.
2004/0002347 A1 1/2004 Hoctor et al.
2004/0015403 A1 1/2004 Moskowitz et al.
2004/0021552 A1 2/2004 Koo
2004/0022384 A1 2/2004 Flores et al.
2004/0025179 A1 2/2004 Russ et al.
2004/0029620 A1 2/2004 Karaoguz
2004/0029635 A1 2/2004 Giobbi
2004/0030764 A1 2/2004 Birk et al.
2004/0030894 A1 2/2004 Labrou et al.
2004/0035644 A1 2/2004 Ford et al.
2004/0039909 A1 2/2004 Cheng
2004/0043753 A1 3/2004 Wake et al.
2004/0044627 A1 3/2004 Russell et al.
2004/0048570 A1 3/2004 Oba et al.
2004/0048609 A1 3/2004 Kosaka
2004/0049687 A1 3/2004 Orsini et al.
2004/0059682 A1 3/2004 Hasumi et al.
2004/0059912 A1 3/2004 Zizzi
2004/0064728 A1 4/2004 Scheurich
2004/0068656 A1 4/2004 Lu
2004/0073792 A1 4/2004 Noble et al.
2004/0077313 A1 4/2004 Oba et al.
2004/0081127 A1 4/2004 Gardner et al.
2004/0082385 A1 4/2004 Silva et al.
2004/0088558 A1 5/2004 Candelore
2004/0090345 A1 5/2004 Hitt
2004/0092231 A1 5/2004 Ayatsuka et al.
2004/0095911 A1 5/2004 Benveniste
2004/0098597 A1 5/2004 Giobbi
2004/0103061 A1 5/2004 Wood et al.
2004/0103062 A1 5/2004 Wood et al.

(56) References Cited

U.S. PATENT DOCUMENTS

2004/0103064 A1 5/2004 Howard et al.
2004/0107169 A1 6/2004 Lowe
2004/0114563 A1 6/2004 Shvodian
2004/0117644 A1 6/2004 Colvin
2004/0123106 A1 6/2004 D'Angelo et al.
2004/0123107 A1 6/2004 Miyazaki et al.
2004/0123127 A1 6/2004 Teicher et al.
2004/0124966 A1 7/2004 Forrest
2004/0127277 A1 7/2004 Walker et al.
2004/0128162 A1 7/2004 Schlotterbeck et al.
2004/0128389 A1 7/2004 Kopchik
2004/0128500 A1 7/2004 Cihula et al.
2004/0128508 A1 7/2004 Wheeler et al.
2004/0128519 A1 7/2004 Klinger et al.
2004/0129787 A1 7/2004 Saito et al.
2004/0132432 A1 7/2004 Moores et al.
2004/0137912 A1 7/2004 Lin
2004/0153344 A1 8/2004 Bui et al.
2004/0153649 A1 8/2004 Rhoads et al.
2004/0158746 A1 8/2004 Hu et al.
2004/0166875 A1 8/2004 Jenkins et al.
2004/0167465 A1 8/2004 Mihai et al.
2004/0176032 A1 9/2004 Kotola et al.
2004/0181695 A1 9/2004 Walker
2004/0186768 A1 9/2004 Wakim et al.
2004/0193925 A1 9/2004 Safriel
2004/0194133 A1 9/2004 Ikeda et al.
2004/0201755 A1 10/2004 Norskog
2004/0203566 A1 10/2004 Leung
2004/0203885 A1 10/2004 Quaid
2004/0203923 A1 10/2004 Mullen
2004/0208139 A1 10/2004 Iwamura
2004/0209690 A1 10/2004 Bruzzese et al.
2004/0209692 A1 10/2004 Schober et al.
2004/0214582 A1 10/2004 Lan et al.
2004/0215615 A1 10/2004 Larsson et al.
2004/0217859 A1 11/2004 Pucci et al.
2004/0218581 A1 11/2004 Cattaneo
2004/0222877 A1 11/2004 Teramura et al.
2004/0230488 A1 11/2004 Beenau et al.
2004/0230809 A1 11/2004 Lowensohn et al.
2004/0234117 A1 11/2004 Tibor
2004/0238621 A1 12/2004 Beenau et al.
2004/0243519 A1 12/2004 Perttila et al.
2004/0246103 A1 12/2004 Zukowski
2004/0246934 A1 12/2004 Kim
2004/0246950 A1 12/2004 Parker et al.
2004/0250037 A1 12/2004 Takemura et al.
2004/0250074 A1 12/2004 Kilian-Kehr
2004/0252012 A1 12/2004 Beenau et al.
2004/0252659 A1 12/2004 Yun et al.
2004/0253996 A1 12/2004 Chen et al.
2004/0254837 A1 12/2004 Roshkoff
2004/0255139 A1 12/2004 Giobbi
2004/0255145 A1 12/2004 Chow
2004/0262384 A1 12/2004 Nishida et al.
2005/0001028 A1 1/2005 Zuili
2005/0001720 A1 1/2005 Mason et al.
2005/0002028 A1 1/2005 Kasapi et al.
2005/0005136 A1 1/2005 Chen et al.
2005/0006452 A1 1/2005 Aupperle et al.
2005/0009517 A1 1/2005 Maes
2005/0020322 A1 1/2005 Ruuska et al.
2005/0021369 A1 1/2005 Cohen et al.
2005/0021561 A1 1/2005 Noonan
2005/0023345 A1 2/2005 Furuyama et al.
2005/0025093 A1 2/2005 Yun et al.
2005/0028168 A1 2/2005 Marcjan
2005/0033689 A1 2/2005 Bonalle et al.
2005/0033703 A1 2/2005 Holdsworth
2005/0035897 A1 2/2005 Perl et al.
2005/0039027 A1 2/2005 Shapiro
2005/0040961 A1 2/2005 Tuttle
2005/0040968 A1 2/2005 Damarla et al.
2005/0044372 A1 2/2005 Aull et al.
2005/0044387 A1 2/2005 Ozolins
2005/0047386 A1 3/2005 Yi
2005/0049013 A1 3/2005 Chang et al.
2005/0050208 A1 3/2005 Chatani
2005/0050324 A1 3/2005 Corbett et al.
2005/0050367 A1 3/2005 Burger et al.
2005/0054431 A1 3/2005 Walker et al.
2005/0055242 A1 3/2005 Bello et al.
2005/0055244 A1 3/2005 Mullan et al.
2005/0058292 A1 3/2005 Diorio et al.
2005/0074126 A1 4/2005 Stanko
2005/0076242 A1 4/2005 Breuer
2005/0080973 A1 4/2005 Lee
2005/0081040 A1 4/2005 Johnson et al.
2005/0084137 A1 4/2005 Kim et al.
2005/0085259 A1 4/2005 Conner et al.
2005/0086115 A1 4/2005 Pearson
2005/0086497 A1 4/2005 Nakayama
2005/0086501 A1 4/2005 Woo et al.
2005/0086515 A1 4/2005 Paris
2005/0089000 A1 4/2005 Bae et al.
2005/0090200 A1 4/2005 Karaoguz et al.
2005/0091338 A1 4/2005 De La Huerga
2005/0091553 A1 4/2005 Chien et al.
2005/0094657 A1 5/2005 Sung et al.
2005/0096053 A1 5/2005 Liu et al.
2005/0097037 A1 5/2005 Tibor
2005/0099824 A1 5/2005 Dowling et al.
2005/0105600 A1 5/2005 Culum et al.
2005/0105734 A1 5/2005 Buer et al.
2005/0107965 A1 5/2005 Kerr et al.
2005/0108164 A1 5/2005 Salafia et al.
2005/0109836 A1 5/2005 Ben-Aissa
2005/0109841 A1 5/2005 Ryan et al.
2005/0113070 A1 5/2005 Okabe
2005/0113102 A1 5/2005 Kwon et al.
2005/0114149 A1 5/2005 Rodriguez et al.
2005/0114150 A1 5/2005 Franklin
2005/0114654 A1 5/2005 Brackett et al.
2005/0116020 A1 6/2005 Smolucha et al.
2005/0116050 A1 6/2005 Jei et al.
2005/0117530 A1 6/2005 Abraham et al.
2005/0119979 A1 6/2005 Murashita et al.
2005/0124294 A1 6/2005 Wentink
2005/0125258 A1 6/2005 Yellin et al.
2005/0128083 A1 * 6/2005 Puzio ................ G08B 13/2462
340/5.2
2005/0136947 A1 6/2005 Llombart-Juan et al.
2005/0137827 A1 6/2005 Takamiya
2005/0137977 A1 6/2005 Wankmueller
2005/0138390 A1 6/2005 Adams et al.
2005/0138576 A1 6/2005 Baumert et al.
2005/0139656 A1 6/2005 Arnouse
2005/0141451 A1 6/2005 Yoon et al.
2005/0149358 A1 7/2005 Sacco et al.
2005/0151623 A1 7/2005 von Hoffmann
2005/0152394 A1 7/2005 Cho
2005/0154897 A1 7/2005 Holloway et al.
2005/0161503 A1 7/2005 Remery et al.
2005/0165684 A1 7/2005 Jensen et al.
2005/0166063 A1 7/2005 Huang
2005/0167482 A1 8/2005 Ramachandran et al.
2005/0169292 A1 8/2005 Young
2005/0177716 A1 8/2005 Ginter et al.
2005/0180385 A1 8/2005 Jeong et al.
2005/0181875 A1 8/2005 Hoehne et al.
2005/0182661 A1 8/2005 Allard et al.
2005/0182975 A1 8/2005 Guo et al.
2005/0187368 A1 8/2005 Ebling et al.
2005/0187792 A1 8/2005 Harper
2005/0192748 A1 9/2005 Andric et al.
2005/0195975 A1 9/2005 Kawakita
2005/0198208 A1 9/2005 Nystrom
2005/0200453 A1 9/2005 Turner et al.
2005/0201345 A1 9/2005 Williamson
2005/0201389 A1 9/2005 Shimanuki et al.
2005/0203682 A1 9/2005 Omino et al.
2005/0203844 A1 9/2005 Ferguson et al.
2005/0210270 A1 9/2005 Rohatgi et al.

(56) References Cited

U.S. PATENT DOCUMENTS

2005/0212657 A1 9/2005 Simon
2005/0215233 A1 9/2005 Perera et al.
2005/0216313 A1 9/2005 Claud et al.
2005/0216639 A1 9/2005 Sparer et al.
2005/0218215 A1 10/2005 Lauden
2005/0220046 A1 10/2005 Falck et al.
2005/0221869 A1 10/2005 Liu et al.
2005/0224573 A1 10/2005 Yoshizane et al.
2005/0229007 A1 10/2005 Bolle et al.
2005/0229240 A1 10/2005 Nanba
2005/0231328 A1 10/2005 Castle et al.
2005/0235364 A1 10/2005 Wilson
2005/0242921 A1 11/2005 Zimmerman et al.
2005/0243787 A1 11/2005 Hong et al.
2005/0246416 A1 11/2005 Blomquist
2005/0249385 A1 11/2005 Kondo et al.
2005/0251688 A1 11/2005 Nanavati et al.
2005/0253683 A1 11/2005 Lowe
2005/0256878 A1 11/2005 Brown et al.
2005/0257072 A1 11/2005 Cross et al.
2005/0257102 A1 11/2005 Moyer et al.
2005/0258229 A1 11/2005 Minemura
2005/0264416 A1 12/2005 Maurer
2005/0265371 A1 12/2005 Sharma et al.
2005/0268111 A1 12/2005 Markham
2005/0269401 A1 12/2005 Spitzer et al.
2005/0272403 A1 12/2005 Ryu et al.
2005/0277385 A1 12/2005 Daum
2005/0278547 A1 12/2005 Hyndman et al.
2005/0281215 A1 12/2005 Budampati et al.
2005/0281320 A1 12/2005 Neugebauer
2005/0282558 A1 12/2005 Choi et al.
2005/0284932 A1 12/2005 Sukeda et al.
2005/0287985 A1 12/2005 Balfanz et al.
2005/0288015 A1 12/2005 Azizi et al.
2005/0288069 A1 12/2005 Arunan et al.
2005/0289473 A1 12/2005 Gustafson et al.
2006/0001525 A1 1/2006 Nitzan et al.
2006/0002349 A1 1/2006 Demirhan
2006/0005035 A1 1/2006 Coughlin
2006/0009216 A1 1/2006 Welnick et al.
2006/0014430 A1 1/2006 Liang et al.
2006/0022042 A1 2/2006 Smets et al.
2006/0022046 A1 2/2006 Iwamura
2006/0022800 A1 2/2006 Krishna et al.
2006/0025180 A1 2/2006 Rajkotia et al.
2006/0026338 A1 2/2006 Ebara et al.
2006/0026673 A1 2/2006 Tsuchida
2006/0030279 A1 2/2006 Leabman
2006/0030353 A1 2/2006 Jun
2006/0034250 A1 2/2006 Kim et al.
2006/0034492 A1 2/2006 Siegel et al.
2006/0041746 A1 2/2006 Kirkup et al.
2006/0046664 A1 3/2006 Paradiso et al.
2006/0050742 A1 3/2006 Grandhi et al.
2006/0053234 A1 3/2006 Kumar et al.
2006/0058102 A1 3/2006 Nguyen et al.
2006/0063575 A1 3/2006 Gatto et al.
2006/0064320 A1 3/2006 Postrel
2006/0064605 A1 3/2006 Giobbi
2006/0065730 A1 3/2006 Quan et al.
2006/0066441 A1 3/2006 Knadle et al.
2006/0069814 A1 3/2006 Abraham et al.
2006/0072586 A1 4/2006 Callaway et al.
2006/0074713 A1 4/2006 Conry et al.
2006/0075230 A1 4/2006 Baird et al.
2006/0075255 A1 4/2006 Duffy et al.
2006/0076401 A1 4/2006 Frerking
2006/0078176 A1 4/2006 Abiko et al.
2006/0080549 A1 4/2006 Okamura et al.
2006/0087407 A1 4/2006 Stewart et al.
2006/0089138 A1 4/2006 Smith et al.
2006/0095369 A1 5/2006 Hofi
2006/0095792 A1 5/2006 Hurtado et al.
2006/0097882 A1 5/2006 Brinkerhoff et al.
2006/0097949 A1 5/2006 Luebke et al.
2006/0101506 A1 5/2006 Gallo et al.
2006/0106645 A1 5/2006 Bergelson et al.
2006/0110012 A1 5/2006 Ritter
2006/0111941 A1 5/2006 Blom
2006/0111955 A1 5/2006 Winter et al.
2006/0112423 A1 5/2006 Villadiego et al.
2006/0113381 A1 6/2006 Hochstein et al.
2006/0116935 A1 6/2006 Evans
2006/0117013 A1 6/2006 Wada
2006/0120287 A1 6/2006 Foti et al.
2006/0129838 A1 6/2006 Chen et al.
2006/0136728 A1 6/2006 Gentry et al.
2006/0136742 A1 6/2006 Giobbi
2006/0136997 A1 6/2006 Telek et al.
2006/0143441 A1 6/2006 Giobbi
2006/0144943 A1 7/2006 Kim
2006/0156027 A1 7/2006 Blake
2006/0158308 A1 7/2006 Mcmullen et al.
2006/0163349 A1 7/2006 Neugebauer
2006/0163350 A1 7/2006 Melton et al.
2006/0165060 A1 7/2006 Dua
2006/0169771 A1 8/2006 Brookner
2006/0170530 A1 8/2006 Nwosu et al.
2006/0170565 A1 8/2006 Husak et al.
2006/0172700 A1 8/2006 Wu
2006/0173846 A1 8/2006 Omae et al.
2006/0173991 A1 8/2006 Piikivi
2006/0174349 A1 8/2006 Cronce et al.
2006/0183426 A1 8/2006 Graves et al.
2006/0183462 A1 8/2006 Kolehmainen
2006/0184531 A1 8/2006 Russlies
2006/0184795 A1 8/2006 Doradla et al.
2006/0185005 A1 8/2006 Graves et al.
2006/0187029 A1 8/2006 Thomas
2006/0190348 A1 8/2006 Ofer et al.
2006/0190413 A1 8/2006 Harper
2006/0194598 A1 8/2006 Kim et al.
2006/0195576 A1 8/2006 Rinne et al.
2006/0198337 A1 9/2006 Hoang et al.
2006/0200467 A1 9/2006 Ohmori et al.
2006/0205408 A1 9/2006 Nakagawa et al.
2006/0208066 A1 9/2006 Finn et al.
2006/0208853 A1 9/2006 Kung et al.
2006/0218196 A1 9/2006 Kurita
2006/0222042 A1 10/2006 Teramura et al.
2006/0226950 A1 10/2006 Kanou et al.
2006/0229909 A1 10/2006 Kaila et al.
2006/0236373 A1 10/2006 Graves et al.
2006/0237528 A1 10/2006 Bishop et al.
2006/0238305 A1 10/2006 Loving et al.
2006/0245620 A1 11/2006 Roques et al.
2006/0255935 A1 11/2006 Scalisi et al.
2006/0258289 A1 11/2006 Dua
2006/0268891 A1 11/2006 Heidari-Bateni et al.
2006/0273176 A1 12/2006 Audebert et al.
2006/0274711 A1 12/2006 Nelson et al.
2006/0279412 A1 12/2006 Holland et al.
2006/0286969 A1 12/2006 Talmor et al.
2006/0287763 A1 12/2006 Ochi et al.
2006/0288095 A1 12/2006 Torok et al.
2006/0288233 A1 12/2006 Kozlay
2006/0290473 A1 12/2006 Mahasenan et al.
2006/0290519 A1 12/2006 Boate et al.
2006/0290580 A1 12/2006 Noro et al.
2006/0292986 A1 12/2006 Bitran et al.
2006/0293925 A1 12/2006 Flom
2006/0294388 A1 12/2006 Abraham et al.
2007/0003111 A1 1/2007 Awatsu et al.
2007/0004393 A1 1/2007 Forsberg et al.
2007/0005403 A1 1/2007 Kennedy et al.
2007/0006298 A1 1/2007 Malone et al.
2007/0007331 A1 1/2007 Jasper et al.
2007/0008070 A1 1/2007 Friedrich
2007/0008916 A1 1/2007 Haugli et al.
2007/0011724 A1 1/2007 Gonzalez et al.
2007/0016637 A1 1/2007 Brawn et al.
2007/0016800 A1 1/2007 Spottswood et al.
2007/0019845 A1 1/2007 Kato

(56) References Cited

U.S. PATENT DOCUMENTS

| | | | | |
|---|---|---|---|---|
| 2007/0029381 | A1 | 2/2007 | Braiman | |
| 2007/0032225 | A1 | 2/2007 | Konicek et al. | |
| 2007/0032288 | A1 | 2/2007 | Nelson et al. | |
| 2007/0033072 | A1 | 2/2007 | Bildirici | |
| 2007/0033150 | A1 | 2/2007 | Nwosu | |
| 2007/0035381 | A1 | 2/2007 | Davis | |
| 2007/0035397 | A1* | 2/2007 | Patenaude | B60R 25/102 340/572.1 |
| 2007/0036396 | A1 | 2/2007 | Sugita et al. | |
| 2007/0038751 | A1 | 2/2007 | Jorgensen | |
| 2007/0039041 | A1 | 2/2007 | Davis | |
| 2007/0043594 | A1 | 2/2007 | Lavergne | |
| 2007/0050259 | A1 | 3/2007 | Wesley | |
| 2007/0050398 | A1 | 3/2007 | Mochizuki | |
| 2007/0050845 | A1 | 3/2007 | Das et al. | |
| 2007/0051794 | A1 | 3/2007 | Glanz et al. | |
| 2007/0051798 | A1 | 3/2007 | Kawai et al. | |
| 2007/0055630 | A1 | 3/2007 | Gauthier et al. | |
| 2007/0060095 | A1 | 3/2007 | Subrahmanya et al. | |
| 2007/0060319 | A1 | 3/2007 | Block et al. | |
| 2007/0061041 | A1 | 3/2007 | Zweig | |
| 2007/0064742 | A1 | 3/2007 | Shvodian | |
| 2007/0069852 | A1 | 3/2007 | Mo et al. | |
| 2007/0070040 | A1 | 3/2007 | Chen et al. | |
| 2007/0072636 | A1 | 3/2007 | Worfolk et al. | |
| 2007/0073553 | A1 | 3/2007 | Flinn et al. | |
| 2007/0075135 | A1 | 4/2007 | Dettinger et al. | |
| 2007/0078761 | A1 | 4/2007 | Kagan et al. | |
| 2007/0084523 | A1 | 4/2007 | Mclean et al. | |
| 2007/0084913 | A1 | 4/2007 | Weston | |
| 2007/0087682 | A1 | 4/2007 | Dacosta | |
| 2007/0087834 | A1 | 4/2007 | Moser et al. | |
| 2007/0090195 | A1 | 4/2007 | Kawamura et al. | |
| 2007/0094088 | A1 | 4/2007 | Mastie et al. | |
| 2007/0100507 | A1 | 5/2007 | Simon | |
| 2007/0100939 | A1 | 5/2007 | Bagley et al. | |
| 2007/0109117 | A1 | 5/2007 | Heitzmann et al. | |
| 2007/0112676 | A1 | 5/2007 | Kontio et al. | |
| 2007/0118891 | A1 | 5/2007 | Buer | |
| 2007/0119923 | A1 | 5/2007 | Garrison et al. | |
| 2007/0120643 | A1 | 5/2007 | Lee | |
| 2007/0120651 | A1 | 5/2007 | Kobayashi et al. | |
| 2007/0120698 | A1* | 5/2007 | Turk | G08B 21/0227 340/539.21 |
| 2007/0130025 | A1 | 6/2007 | Nakajima | |
| 2007/0132586 | A1 | 6/2007 | Plocher et al. | |
| 2007/0133478 | A1 | 6/2007 | Armbruster et al. | |
| 2007/0136103 | A1 | 6/2007 | Kim et al. | |
| 2007/0136407 | A1 | 6/2007 | Rudelic | |
| 2007/0142032 | A1 | 6/2007 | Balsillie | |
| 2007/0143626 | A1 | 6/2007 | Okuda | |
| 2007/0147332 | A1 | 6/2007 | Lappetelainen et al. | |
| 2007/0152826 | A1 | 7/2007 | August et al. | |
| 2007/0156850 | A1 | 7/2007 | Corrion | |
| 2007/0157249 | A1 | 7/2007 | Cordray et al. | |
| 2007/0158411 | A1 | 7/2007 | Krieg, Jr. | |
| 2007/0159301 | A1 | 7/2007 | Hirt et al. | |
| 2007/0159994 | A1 | 7/2007 | Brown et al. | |
| 2007/0164847 | A1 | 7/2007 | Crawford et al. | |
| 2007/0169121 | A1 | 7/2007 | Hunt et al. | |
| 2007/0174809 | A1 | 7/2007 | Brown et al. | |
| 2007/0174868 | A1 | 7/2007 | Hitaka | |
| 2007/0176756 | A1 | 8/2007 | Friedrich | |
| 2007/0176778 | A1 | 8/2007 | Ando et al. | |
| 2007/0180047 | A1 | 8/2007 | Dong et al. | |
| 2007/0180207 | A1 | 8/2007 | Garfinkle | |
| 2007/0187266 | A1 | 8/2007 | Porter et al. | |
| 2007/0192601 | A1 | 8/2007 | Spain et al. | |
| 2007/0194882 | A1 | 8/2007 | Yokota et al. | |
| 2007/0197261 | A1 | 8/2007 | Humbel | |
| 2007/0198436 | A1 | 8/2007 | Weiss | |
| 2007/0198848 | A1 | 8/2007 | Bjorn | |
| 2007/0204078 | A1 | 8/2007 | Boccon-Gibod et al. | |
| 2007/0205860 | A1 | 9/2007 | Jones et al. | |
| 2007/0205861 | A1 | 9/2007 | Nair et al. | |
| 2007/0207750 | A1 | 9/2007 | Brown et al. | |
| 2007/0213048 | A1 | 9/2007 | Trauberg | |
| 2007/0213090 | A1 | 9/2007 | Holmberg | |
| 2007/0214492 | A1 | 9/2007 | Gopi et al. | |
| 2007/0218921 | A1 | 9/2007 | Lee et al. | |
| 2007/0219926 | A1 | 9/2007 | Korn | |
| 2007/0220272 | A1 | 9/2007 | Campisi et al. | |
| 2007/0223403 | A1 | 9/2007 | Furuskar et al. | |
| 2007/0229260 | A1 | 10/2007 | Braun et al. | |
| 2007/0229268 | A1 | 10/2007 | Swan et al. | |
| 2007/0236332 | A1 | 10/2007 | Quan et al. | |
| 2007/0245157 | A1 | 10/2007 | Giobbi et al. | |
| 2007/0245158 | A1 | 10/2007 | Giobbi et al. | |
| 2007/0247366 | A1 | 10/2007 | Smith et al. | |
| 2007/0250718 | A1 | 10/2007 | Lee et al. | |
| 2007/0250920 | A1 | 10/2007 | Lindsay | |
| 2007/0258626 | A1 | 11/2007 | Reiner | |
| 2007/0260883 | A1 | 11/2007 | Giobbi et al. | |
| 2007/0260888 | A1 | 11/2007 | Giobbi et al. | |
| 2007/0262134 | A1 | 11/2007 | Humphrey et al. | |
| 2007/0266257 | A1 | 11/2007 | Camaisa et al. | |
| 2007/0268130 | A1 | 11/2007 | Yee et al. | |
| 2007/0268862 | A1 | 11/2007 | Singh et al. | |
| 2007/0271194 | A1 | 11/2007 | Walker et al. | |
| 2007/0271433 | A1 | 11/2007 | Takemura | |
| 2007/0273517 | A1 | 11/2007 | Govind | |
| 2007/0277044 | A1 | 11/2007 | Graf et al. | |
| 2007/0279190 | A1 | 12/2007 | Lugt et al. | |
| 2007/0280509 | A1 | 12/2007 | Owen et al. | |
| 2007/0285212 | A1 | 12/2007 | Rotzoll | |
| 2007/0285238 | A1 | 12/2007 | Batra | |
| 2007/0287386 | A1 | 12/2007 | Agrawal et al. | |
| 2007/0288263 | A1 | 12/2007 | Rodgers | |
| 2007/0288752 | A1 | 12/2007 | Chan | |
| 2007/0293155 | A1 | 12/2007 | Liao et al. | |
| 2007/0294755 | A1 | 12/2007 | Dadhia et al. | |
| 2007/0296544 | A1 | 12/2007 | Beenau et al. | |
| 2007/0299782 | A1 | 12/2007 | Beenau et al. | |
| 2007/0300052 | A1 | 12/2007 | Jevans | |
| 2008/0001724 | A1 | 1/2008 | Soleimani et al. | |
| 2008/0001783 | A1 | 1/2008 | Cargonja et al. | |
| 2008/0005432 | A1 | 1/2008 | Kagawa | |
| 2008/0008359 | A1 | 1/2008 | Beenau et al. | |
| 2008/0011842 | A1 | 1/2008 | Curry et al. | |
| 2008/0012685 | A1 | 1/2008 | Friedrich et al. | |
| 2008/0012767 | A1 | 1/2008 | Caliri et al. | |
| 2008/0016004 | A1 | 1/2008 | Kurasaki et al. | |
| 2008/0019578 | A1 | 1/2008 | Saito et al. | |
| 2008/0028227 | A1 | 1/2008 | Sakurai | |
| 2008/0028453 | A1 | 1/2008 | Nguyen et al. | |
| 2008/0040609 | A1 | 2/2008 | Giobbi | |
| 2008/0046366 | A1 | 2/2008 | Bemmel et al. | |
| 2008/0046715 | A1 | 2/2008 | Balazs et al. | |
| 2008/0049700 | A1 | 2/2008 | Shah et al. | |
| 2008/0056544 | A1 | 3/2008 | Aikawa et al. | |
| 2008/0061941 | A1 | 3/2008 | Fischer et al. | |
| 2008/0065181 | A1 | 3/2008 | Stevenson | |
| 2008/0071577 | A1 | 3/2008 | Highley | |
| 2008/0072063 | A1 | 3/2008 | Takahashi et al. | |
| 2008/0077359 | A1 | 3/2008 | Ito | |
| 2008/0080022 | A1 | 4/2008 | Gogulapati | |
| 2008/0088475 | A1 | 4/2008 | Martin | |
| 2008/0090548 | A1 | 4/2008 | Ramalingam | |
| 2008/0094228 | A1 | 4/2008 | Welch et al. | |
| 2008/0095359 | A1 | 4/2008 | Schreyer et al. | |
| 2008/0107089 | A1 | 5/2008 | Larsson et al. | |
| 2008/0109895 | A1 | 5/2008 | Janevski | |
| 2008/0111752 | A1 | 5/2008 | Lindackers et al. | |
| 2008/0114694 | A1 | 5/2008 | Hamdane et al. | |
| 2008/0114847 | A1 | 5/2008 | Ma et al. | |
| 2008/0125965 | A1* | 5/2008 | Carani | G08G 1/13 340/539.13 |
| 2008/0127176 | A1 | 5/2008 | Lee et al. | |
| 2008/0127225 | A1 | 5/2008 | Mullis, et al. | |
| 2008/0129450 | A1 | 6/2008 | Riegebauer | |
| 2008/0129463 | A1 | 6/2008 | Tuttle | |
| 2008/0141361 | A1 | 6/2008 | Balfanz | |
| 2008/0142588 | A1 | 6/2008 | Blum | |
| 2008/0148351 | A1 | 6/2008 | Bhatia et al. | |

(56) References Cited

U.S. PATENT DOCUMENTS

2008/0149705 A1 6/2008 Giobbi et al.
2008/0150678 A1 6/2008 Giobbi et al.
2008/0154727 A1 6/2008 Carlson
2008/0156866 A1 7/2008 Mcneal
2008/0159599 A1 7/2008 Kajihara et al.
2008/0164997 A1 7/2008 Aritsuka et al.
2008/0169909 A1 7/2008 Park et al.
2008/0176713 A1 7/2008 Olivera et al.
2008/0180213 A1 7/2008 Flax
2008/0186166 A1 8/2008 Zhou et al.
2008/0188308 A1 8/2008 Shepherd et al.
2008/0195735 A1 8/2008 Hodges et al.
2008/0195863 A1 8/2008 Kennedy
2008/0201733 A1 8/2008 Ertugrul et al.
2008/0201768 A1 8/2008 Koo et al.
2008/0203107 A1 8/2008 Conley et al.
2008/0208016 A1 8/2008 Hughes et al.
2008/0209571 A1 8/2008 Bhaskar et al.
2008/0211627 A1 9/2008 Shinzaki
2008/0214300 A1 9/2008 Williams et al.
2008/0218416 A1 9/2008 Handy et al.
2008/0222701 A1 9/2008 Saaranen et al.
2008/0223918 A1 9/2008 Williams et al.
2008/0228524 A1 9/2008 Brown
2008/0235144 A1 9/2008 Phillips
2008/0238625 A1 10/2008 Rofougaran et al.
2008/0246613 A1 10/2008 Linstrom et al.
2008/0250388 A1 10/2008 Meyer et al.
2008/0251579 A1 10/2008 Larsen
2008/0252419 A1 10/2008 Batchelor et al.
2008/0278325 A1 11/2008 Zimman et al.
2008/0278327 A1 11/2008 Nierenberg et al.
2008/0284597 A1 11/2008 Shah
2008/0289018 A1 11/2008 Kawaguchi
2008/0289030 A1 11/2008 Poplett
2008/0289032 A1 11/2008 Aoki et al.
2008/0303637 A1 12/2008 Gelbman et al.
2008/0303638 A1 12/2008 Nguyen et al.
2008/0306759 A1 12/2008 Ilkin et al.
2008/0313728 A1 12/2008 Pandrangi et al.
2008/0314971 A1 12/2008 Faith et al.
2008/0316002 A1 12/2008 Brunet et al.
2008/0316045 A1 12/2008 Sriharto et al.
2009/0002134 A1 1/2009 Mcallister
2009/0006846 A1 1/2009 Rosenblatt
2009/0013191 A1 1/2009 Popowski
2009/0016573 A1 1/2009 Mcafee et al.
2009/0024584 A1 1/2009 Dharap et al.
2009/0033464 A1 2/2009 Friedrich
2009/0033485 A1 2/2009 Naeve et al.
2009/0036164 A1 2/2009 Rowley
2009/0037326 A1 2/2009 Chitti et al.
2009/0040041 A1 2/2009 Janetis et al.
2009/0041309 A1 2/2009 Kim et al.
2009/0043253 A1 2/2009 Podaima
2009/0045916 A1 2/2009 Nitzan et al.
2009/0050686 A1 2/2009 Kon et al.
2009/0050688 A1 2/2009 Kon et al.
2009/0052389 A1 2/2009 Qin et al.
2009/0070146 A1 3/2009 Haider et al.
2009/0070219 A1 3/2009 D'Angelo et al.
2009/0075592 A1 3/2009 Nystrom et al.
2009/0076849 A1 3/2009 Diller
2009/0081996 A1 3/2009 Duggal et al.
2009/0085724 A1 4/2009 Naressi et al.
2009/0085748 A1 4/2009 Barnes et al.
2009/0094681 A1 4/2009 Sadler et al.
2009/0096580 A1 4/2009 Paananen
2009/0115609 A1* 5/2009 Weaver .................. G06Q 10/08 340/572.1
2009/0121890 A1 5/2009 Brown et al.
2009/0125401 A1 5/2009 Beenau et al.
2009/0138953 A1 5/2009 Lyon
2009/0140045 A1 6/2009 Evans
2009/0150762 A1 6/2009 Febonio et al.
2009/0157512 A1 6/2009 King
2009/0160646 A1* 6/2009 Mackenzie ........ G08B 13/2462 340/602
2009/0165123 A1 6/2009 Giobbi
2009/0176566 A1 7/2009 Kelly
2009/0177495 A1 7/2009 Abousy et al.
2009/0182582 A1 7/2009 Hammon
2009/0195461 A1 8/2009 Hirt
2009/0199206 A1 8/2009 Finkenzeller et al.
2009/0200378 A1 8/2009 Doherty et al.
2009/0206992 A1 8/2009 Giobbi et al.
2009/0221301 A1* 9/2009 Riley .................... G01S 5/0231 455/456.5
2009/0222908 A1 9/2009 Warren
2009/0232362 A1 9/2009 Otsubo et al.
2009/0237245 A1 9/2009 Brinton et al.
2009/0237253 A1 9/2009 Neuwirth
2009/0239667 A1 9/2009 Rowe et al.
2009/0253516 A1 10/2009 Hartmann et al.
2009/0254448 A1 10/2009 Giobbi
2009/0254971 A1 10/2009 Herz et al.
2009/0264712 A1 10/2009 Baldus et al.
2009/0307764 A1 12/2009 Isobe et al.
2009/0310514 A1 12/2009 Jeon et al.
2009/0313689 A1 12/2009 Nystroem et al.
2009/0319788 A1 12/2009 Zick et al.
2009/0320118 A1 12/2009 Mueller et al.
2009/0322510 A1 12/2009 Berger et al.
2009/0322566 A1 12/2009 Shirakawa
2009/0325603 A1 12/2009 Van et al.
2009/0327102 A1* 12/2009 Maniar .................. G06Q 10/08 705/28
2009/0328182 A1 12/2009 Malakapalli et al.
2010/0005526 A1 1/2010 Tsuji et al.
2010/0007498 A1 1/2010 Jackson
2010/0008545 A1 1/2010 Ueki et al.
2010/0022239 A1 1/2010 Anzai
2010/0022308 A1 1/2010 Hartmann et al.
2010/0023074 A1 1/2010 Powers et al.
2010/0037255 A1 2/2010 Sheehan et al.
2010/0039280 A1* 2/2010 Holm ................. G06K 19/0717 340/669
2010/0062743 A1 3/2010 Jonsson
2010/0077214 A1 3/2010 Jogand-Coulomb et al.
2010/0088116 A1 4/2010 Eisenberg et al.
2010/0091987 A1 4/2010 Takahashi et al.
2010/0117794 A1 5/2010 Adams et al.
2010/0127067 A1 5/2010 Eisenberg et al.
2010/0134257 A1 6/2010 Puleston et al.
2010/0169442 A1 7/2010 Liu et al.
2010/0169964 A1 7/2010 Liu et al.
2010/0172567 A1 7/2010 Prokoski
2010/0174911 A1 7/2010 Isshiki
2010/0188226 A1 7/2010 Seder et al.
2010/0214100 A1 8/2010 Page
2010/0277283 A1 11/2010 Burkart et al.
2010/0277286 A1 11/2010 Burkart et al.
2010/0289644 A1* 11/2010 Slavin .................... G08B 25/14 340/568.1
2010/0291896 A1 11/2010 Corda
2010/0305843 A1 12/2010 Yan et al.
2010/0328033 A1 12/2010 Kamei
2010/0330958 A1 12/2010 Corda et al.
2011/0034160 A1 2/2011 Corda et al.
2011/0053605 A1 3/2011 Carpio et al.
2011/0072034 A1 3/2011 Sly et al.
2011/0072132 A1 3/2011 Shafer et al.
2011/0080264 A1* 4/2011 Clare ................. G06K 7/10475 340/10.1
2011/0082735 A1 4/2011 Kannan et al.
2011/0085287 A1 4/2011 Ebrom et al.
2011/0091136 A1 4/2011 Danch et al.
2011/0105854 A1* 5/2011 Kiani ...................... G16Z 99/00 600/300
2011/0116358 A9 5/2011 Li et al.
2011/0121964 A1* 5/2011 Bannard ................ G08B 21/24 340/539.13
2011/0126188 A1 5/2011 Bernstein et al.

(56) References Cited

U.S. PATENT DOCUMENTS

2011/0145570 A1 6/2011 Gressel et al.
2011/0169668 A1 7/2011 Henriksson
2011/0181443 A1* 7/2011 Gutierrez ........... G01C 21/3697 340/990
2011/0221568 A1 9/2011 Giobbi
2011/0227740 A1 9/2011 Wohltjen
2011/0238517 A1 9/2011 Ramalingam et al.
2011/0246790 A1 10/2011 Koh et al.
2011/0266348 A1 11/2011 Denniston, Jr.
2011/0307599 A1 12/2011 Saretto et al.
2012/0016305 A1* 1/2012 Jollota .................. G16H 20/17 604/151
2012/0028609 A1 2/2012 Hruska
2012/0030006 A1 2/2012 Yoder et al.
2012/0069776 A1 3/2012 Caldwell et al.
2012/0086571 A1 4/2012 Scalisi et al.
2012/0161936 A1 6/2012 Yoon et al.
2012/0182123 A1 7/2012 Butler et al.
2012/0212322 A1 8/2012 Idsoee
2012/0226451 A1 9/2012 Bacot et al.
2012/0226565 A1 9/2012 Drozd
2012/0226907 A1 9/2012 Hohberger et al.
2012/0238287 A1 9/2012 Scherzer
2012/0278188 A1 11/2012 Attar et al.
2012/0300753 A1 11/2012 Brown et al.
2012/0310720 A1 12/2012 Balsan et al.
2013/0019295 A1 1/2013 Park et al.
2013/0019323 A1 1/2013 Arvidsson et al.
2013/0044111 A1 2/2013 Vangilder et al.
2013/0095762 A1 4/2013 Inagaki et al.
2013/0111543 A1 5/2013 Brown et al.
2013/0135082 A1 5/2013 Xian et al.
2013/0179201 A1 7/2013 Fuerstenberg et al.
2013/0219186 A1 8/2013 Giobbi et al.
2013/0276140 A1 10/2013 Coffing et al.
2013/0277425 A1 10/2013 Sharma et al.
2013/0297514 A1 11/2013 Giobbi
2013/0312082 A1 11/2013 Izu et al.
2013/0315210 A1 11/2013 Brown et al.
2013/0331063 A1 12/2013 Cormier et al.
2014/0074696 A1 3/2014 Glaser
2014/0085479 A1* 3/2014 Haas ...................... G06Q 10/08 348/E7.085
2014/0147018 A1 5/2014 Argue et al.
2014/0207686 A1 7/2014 Experton
2014/0256511 A1 9/2014 Smith
2014/0266604 A1 9/2014 Masood et al.
2014/0266713 A1 9/2014 Sehgal et al.
2014/0297438 A1 10/2014 Dua
2014/0337920 A1 11/2014 Giobbi
2015/0026480 A1 1/2015 Giobbi et al.
2015/0039451 A1 2/2015 Bonfiglio
2015/0138330 A1 5/2015 Krishnamoorthi
2015/0294293 A1 10/2015 Signarsson
2015/0301155 A1* 10/2015 Roisen .................. G01S 5/0289 340/8.1
2015/0310385 A1 10/2015 King et al.
2015/0310440 A1 10/2015 Hynes et al.
2016/0005020 A1 1/2016 Fernando et al.
2016/0027138 A1 1/2016 Larsen
2016/0093081 A1 3/2016 Kim et al.
2016/0133123 A1 5/2016 Giobbi et al.
2016/0171200 A1 6/2016 Giobbi
2016/0203349 A1 7/2016 Giobbi
2016/0205682 A1 7/2016 Brown et al.
2016/0210614 A1 7/2016 Hall
2016/0300236 A1 10/2016 Wiley et al.
2016/0306956 A1 10/2016 Giobbi
2017/0041315 A1 2/2017 Giobbi
2017/0085564 A1 3/2017 Giobbi et al.
2017/0091548 A1 3/2017 Agrawal et al.
2017/0221327 A1* 8/2017 Wu ........................ G08B 25/10
2017/0270738 A1 9/2017 Giobbi
2017/0309165 A1 10/2017 Brown et al.
2017/0353500 A1 12/2017 Jacobsen et al.
2018/0019998 A1 1/2018 Giobbi
2018/0129799 A1 5/2018 Giobbi
2018/0322718 A1 11/2018 Qian et al.
2018/0357475 A1 12/2018 Honda et al.
2019/0065721 A1 2/2019 Giobbi
2019/0087612 A1* 3/2019 Sengstaken, Jr. ....... A61J 1/035
2019/0172281 A1 6/2019 Einberg et al.
2019/0260724 A1 8/2019 Hefetz et al.
2019/0289562 A1 9/2019 Brown
2020/0020216 A1* 1/2020 Slavin ................ G08B 13/2402
2020/0351873 A1 11/2020 Brown et al.
2021/0099952 A1* 4/2021 Sengupta .......... H04W 52/0212
2021/0219869 A1 7/2021 Ryu et al.
2021/0241592 A1 8/2021 Allen et al.
2022/0091420 A1* 3/2022 Woods ............... G02B 27/0172
2022/0210643 A1 6/2022 Hynds et al.
2022/0240050 A1* 7/2022 Christensen ........ G01S 5/02213
2025/0093521 A1* 3/2025 Czarnecky ............ G01S 5/0027

FOREIGN PATENT DOCUMENTS

EP 1600885 A1 11/2005
EP 2937805 A1 10/2015
JP 10-049604 A 2/1998
KR 10-2007-0060937 A 6/2007
WO 90/06633 A1 6/1990
WO 99/56429 A1 11/1999
WO 00/62505 A1 10/2000
WO 01/22724 A1 3/2001
WO 01/35334 A1 5/2001
WO 01/48714 A1 7/2001
WO 01/75876 A1 10/2001
WO 01/77790 A1 10/2001
WO WO/2002/067009 8/2002
WO 2004/010774 A1 2/2004
WO 2004/038563 A2 5/2004
WO 2004/042563 A2 5/2004
WO 2005/031663 A2 4/2005
WO 2005/050450 A1 6/2005
WO 2005/086802 A2 9/2005
WO 2005/104584 A1 11/2005
WO 2007/008540 A2 1/2007
WO 2007/081947 A2 7/2007
WO 2007/087558 A2 8/2007

OTHER PUBLICATIONS

Mciver et al., "Identification and Verification Working Together," Bioscrypl, While Paper: Identification and Verification Working Together, Aug. 27, 2004, retrieved from www.ibia.org/membersadmin/whilepapers/pdf/15/Identification%20and%20Verification%20Working%20Together.pdf on Jan. 7, 2007, 5 pgs.

Micronas, "Micronas and Thomson Multimedia Showcase a New Copy Protection System that Will Drive the Future of Digital Television," www.micronas.com: Jan. 8, 2002, 3 pgs.

MIT Computer Science and Artificial Intelligence Laboratory, "Cricket v2 User Manual," Cricket Project, MIT Computer Science and Artificial Intelligence Lab, Cambridge, MA, Jan. 2005, 57 pgs., available online at https://web.archive.org/web/20041206144922/http:/cricket.csail.mit.edu/v2man.html.

Motorola, Inc., "Motorola First to Demonstrate ZigBee 2.4 GHz Wireless Networking Technology," press release, Mar. 27, 2003, 2 pgs., archived at https://web.archive.org/web/20050205053308/http:/www.motorola.com/mediacenter/news/detail/0,1958,2743_2228 23,00.html.

Muller, "Desktop Encyclopedia of the Internet," 1999, Artech House Inc., Norwood, MA, all pages.

National Criminal Justice Reference Service, "Antenna Types," Dec. 11, 2006, online at http://ncjrs.gov/pdfffiles1/nij/185030b.pdf, retrieved from http://web.archive.erg/web/*/http://www.ncjrs.gov/pdffiles1/nij/185030b.pdf on Jan. 12, 2011, 1 pg.

Nel et al., "Generation of Keys for use with the Digital Signature Standard (DSS)," Communications and Signal Processing, Proceedings of the 1993 IEEE South African Symposium, Aug. 6, 1993, pp. 6-11.

(56) References Cited

OTHER PUBLICATIONS

Nerd Vitiles, "magicJack: Could It Be the Asterisk Killer?" Aug. 1, 2007, retrieved from http://nerdviLlles.com/index.php7p=187 on or before Oct. 11, 2011, 2 pgs.
Nilsson et al., "Match-on-Card for Java Cards," Precise Biometrics, white paper, Apr. 2004, retrieved from www.ibiaorg/membersadmin/whitepapers/pdf/17/Precise%20Match-on-Card%20for%20Java%20Cards.pdf on Jan. 7, 2007, 5 pgs.
Noore, "Highly Robust Biometric Smart Card Design." IEEE Transactions on Consumer Electronics, vol. 46, No. 4, Nov. 2000, pp. 1059-1063.
Nordin, "Match-on-Card Technology," Precise Biometrics, white paper, Apr. 2004, retrieved from www.ibia.org/membersadmin/whitepapers/pdf/17/Precise%20Match-on-Card%20technology.pdf on Jan. 7, 2007, 7 pgs.
Nordin, "Match-on-Card Technology," Precise Biometrics, white paper, Apr. 2004, retrieved from www.ibia.org/membersadmin/whitepapers/pdf/17/Precise%20Match-on-Card%2otechnology.pdf on Jan. 7, 2007, 7 pgs.
NPL Search Terms (Year: 2023).
Paget, "The Security Behind Secure Extranels," Enterprise Systems Journal, vol. 14, No. 12, Dec. 1999, 4 pgs.
Pash, "Automate proximity and location-based computer actions," Jun. 5, 2007, retrieved from http://lifehacker.com/265822/automate-proximity-and-location+based-computer-actionson or before Oct. 11, 2011, 3 pgs.
PCT International Preliminary Report and Written Opinion of the International Searching Authority, Application No. PCT/US2008/087835, mailing date Jul. 1, 2010, 8 pages.
Petition for Inter Partes Review of U.S. Pat. No. 10,698,989, Aug. 26, 2021, 3356 pgs.
Petition for Inter Partes Review of U.S. Pat. No. 8,352,730, Aug. 26, 2021, 2450 pgs.
Petition for Inter Partes Review of U.S. Pat. No. 9,049,188, Aug. 26, 2021, 800 pgs.
Petition for Inter Partes Review of U.S. Pat. No. 9,235,700, Aug. 26, 2021, 466 pgs.
Petition for Inter Partes Review of U.S. Pat. No. 9,298,905, Aug. 26, 2021, 1941 pgs.
Pope et al., "Oasis Digital Signature Services: Digital Signing without the Headaches," IEEE Internet Computing, vol. 10, Sep./Oct. 2006, pp. 81-84.
Priyantha, "The Cricket Indoor Location System," Ph.D. thesis submitted to Department of Electrical Engineering and Computer Science, Massachusetts Institute of Technology, Jun. 2005, 199 pgs.
Request for Ex Parte Reexamination of U.S. Pat. No. 10,698,989, Jun. 8, 2022, 1505 pgs.
Request for Ex Parte Reexamination of U.S. Pat. No. 8,352,730, Jun. 8, 2022, 1401 pgs.
Request for Ex Parte Reexamination of U.S. Pat. No. 9,298,905, Jun. 8, 2022, 1123 pgs.
Rodriguez et al., "In-building location using Bluetooth," Proceedings of the International Workshop on Wireless Ad-Hoc Networks (IWWAN 2005), May 23-26, 2005, London, England, 7 pgs.
Saflink Corporation, "SAFModule (Trademark): A Look Into Strong Authentication," white paper, retrieved from www.ibia.org/membersadmin/whilepapers/pdf/6/SAFmod_WP.pdf on Jan. 7, 2007, 8 pgs.
Sapsford, "E-Business: Sound Waves Could Help Ease Web-Fraud Woes," Wall Street Journal, Aug. 14, 2000, p. B1.
Schneier, Applied Cryptography, Second Edition: Protocols, Algorithms, and Source Doe in C, Jan. 1, 1996, John Wley & Sons, Inc., 1027 pgs.
Serrao et al., "Protecting Digital Music Delivery and Consumption using the OCCAMM Project Framework," Proceedings of the Second International Conference on Web Delivering of Music, 2002, pp. 38-45, doi: 10.1109/WDM.2002.1176192.
Singh et al. "A Constraint-Based Biometric Scheme on ATM and Swiping Machine." 2016 International Conference on Computational Techniques in Information and Communication Technologies (ICCTICT), Mar. 11, 2016, pp. 74-79.
Smart Card Alliance, "Alliance Activities: Publications: Identity: Identity Management Systems, Smart Cards anc Privacy," 1997-2007, retrieved from www.smartcardalliance.org/pages/publications-identity on Jan. 7, 2007, 3 pgs.
Smart Card Alliance, "Contactless Technology for Secure Physical Access: Technology and Standards Choices," Smart Card Alliance, Oct. 2002, pp. 1-48.
Smart Card Alliance, "Smart Cards and Biometrics White Paper: Smart Card Alliance," May 2002, retrieved from http://www.securitymanagement.com/library/smartcard faqtech0802.pdf on Jan. 7, 2007, 7 pgs.
Smart Card Alliance, Contactless Payment and the Retail Point of Sale: Applications, Technologies and Transaction Models, Mar. 1, 2003, a Smart Card Alliance Report, 50 pgs.
Smart Card Alliance, Smart Card Alliance—The Alliance, Jan. 22, 2001, http://www.smartcardalliance.org, 1 pg.
SPLASHID, "SplashID—Secure Password Manager for PDA's and Smartphones," Mar. 8, 2007, retrieved from http://www.splashdata/com/splashid/ via http://www.archive.org/ on or before Oct. 11, 2011, 2 pgs.
Srivastava, "Is internet security a major issue with respect to the slow acceptance rate of digital signatures," Jan. 2, 2005, Computer Law & Security Report, pp. 392-404.
Tadlys Ltd., "'Hotspot' Gaming Arcade," at least as early as Dec. 9, 2004, 2 pgs., archived at https://web.archive.org/web/20041209234518/http://www.tadlys.com/media/downloads/Tadlys_gaming_arcade.pdf.
Tadlys Ltd., "About Tadlys," at least as early as Apr. 5, 2001, 1 pg., archived at https://web.archive.org/web/20010405044249/http:/www.tadlys.com/about.html.
Tadlys Ltd., "An Advertisers' Dream—From direct marketing to sales," Nov. 2004, 2 pgs., archived at https://web.archive.org/web/20041101092944/http://www.tadlys.com/media/downloads/m-commerce_app.pdf.
Tadlys Ltd., "Bluetooth Glossary," at least as early as Jun. 2004, 12 pgs., archived at https://web.archive.org/web/20040531082349/http://www.tadlys.com/pages/Downloads_content.asp?intGlobalId=1.
Tadlys Ltd., "First Demo of Distribution and Redemption of e-Coupons over Bluetooth," Tadlys Company News anc Events, Jun. 5, 2001, 1 pg., archived at https://web.archive.org/web/20040601051516/http://tadlys.com/Pages/news_content.asp?iGlobalID=17.
Tadlys Ltd., "Indoor Location Networks," at least as early as Apr. 3, 2004, 1 pg., archived at https://web. archive.org/web/20040403200221/http:/www.tadlys.com/Pages/Product_content.asp?iGlobalId=2.
Tadlys Ltd., "Operator Systems," at least as early as Nov. 1, 2004, 2 pgs., archived at https://web.archive.org/web/20041101101402/http://www.tadlys.com/media/downloads/operator_network.pdf.
Tadlys Ltd., "Tadlys Announces Range of Bluetooth Access Network Solutions," Tadlys Company News and Events, Jan. 22, 2001, 1 pg., archived at https://web.archive.org/web/20040624122319/http://www.tadlys.com/Pages/news_content.asp?iGlobalID=16.
Tadlys Ltd., "Tadlys' Wire free networking solutions," Feb. 2001, 2 pgs., archived at https://web.archive.org/web/20010204012700/http:/www.tadlys.com/solutions.html.
Tadlys Ltd., "Wireless hospital network," at least as early as Jul. 1, 2004, 2 pgs., archived at https://web.archive.org/web/20040701105046/http://www.tadlys.com/media/downloads/tadlys_hospital_wireless_network.pdf.
Machine generated English translation of JPH10049604 Shimadzu Corp.published Feb. 20, 1998. 33 pages, downloaded from Espacenet on Nov. 13, 2017.
"IEEE." IEEE Standards: Get IEEE 801 (TM) Wireless Lans IEEE 802, 2004, web.archive.org/web/200404141121 001standards. ieee.org:80/getieee802.
"802.15.3b Part 15.3: Wireless Medium Access Control (MAC) and Physical Layer (PHY) Specifications for High Rate Wireless Personal Area Networks (WPANs)." IEEE-SA Standards Board, May 5, 2006.
"Get IEEE 802 Update." Nov. 9, 2018. 8 pgs.

(56) References Cited

OTHER PUBLICATIONS

"IEEE Standards Association." Terms of Use for IEEE Standards Publications Delivered in Electronic Form, IEEE, 2005, https://web.archive.org/web/20050529084555/standards.ieee.org:80/getieee802/download/.

"IEEE." "get IEEE 802"(Tm) Home Page, 2003, web.archive.org/web/20031008112815/standards.ieee.org:80/getieee802/.

"IEEE." Welcome to Standards Information Network, Jun. 3, 2004, web.archive.org/web/20040603154924/standards.ieee.org:80/standardspress/.

Cai, et al. "A Novel Design of IEEE 802.15.3 Mac over UWB." IEEE 60th Vehicular Technology Conference, 2004. VTC2004-Fall. 2004, vol. 7, pp. 5297-5301, doi:10.1109/vetecf.2004.1405113.

Cooklev, Todor. "A Study of IEEE 802.11, 802.15, and 802.16." Wireless Communication Standards, Standards Information Network, IEEE Press, New York, NY, 2004, pp. 1-200.

Gilb, James P. K. "Draft Running Comment Resolution." IEEE P802.15 Working Group for Wireless Personal Area Networks (WPANs), Oct. 10, 2004, pp. 1-27.

Gilb, James P. K. Wireless Multimedia: A Guide to the IEEE 802.15.3 Standard. Standards Information Network, IEEE Press, 2004.

Guo, et al. "Intra-Superframe Power Management for IEEE 802.15.3 WPAN." IEEE Communications Letters, vol. 9, No. 3, Mar. 2005, pp. 228-230, doi:10.1109/lcomm.2005.03023.

IEEE Computer Society, "IEEE Std 802.15.3—Part 15.3: Wireless Medium Access Control (MAC) and Physical Layer (PHY) Specifications for High Rate Wireless Personal Area Networks (WPANs)," The Institute of electrical and Electronics Engineers, Inc., New York, NY, Oct. 1, 2003, 324 pgs.

Petition for Inter Partes Review of U.S. Pat. No. 10,698,989, Mar. 18, 2025, 99 pgs.

Petition for Inter Partes Review of U.S. Pat. No. 8,219,129, Dec. 23, 2024, 102 pgs.

Petition for Inter Partes Review of U.S. Pat. No. 8,457,672, Dec. 23, 2024, 94 pgs.

Petition for Inter Partes Review of U.S. Pat. No. 9,049,188, Feb. 7, 2025, 84 pgs.

Petition for Inter Partes Review of U.S. Pat. No. 9,265,043, Dec. 23, 2024, 94 pgs.

Wang et al. "Comparison of IEEE 802.11e and IEEE 802.15.3 MAC," 2004, pp. 675-680.

ZENG RanRan and Kuo, Geng-Sheng. "A Novel Scheduling Scheme and Mac Enhancements for IEEE 802.15.3 High-Rate WPAN." IEEE Wireless Communications and Networking Conference, 2005, vol. 4, pp. 2478-2483, doi:10.1109/wcnc.2005.1424903.

Farouk et al., "Authentication Mechanisms in Grid Computing Environment: Comparative Study," IEEE, Oct. 2012, p. 1-6.

Fasca, "S3, Via Formalize Agreement," Electronic News, The Circuit, 45(45, Nov. 8, 1999), p. 20.

Fasca, Chad, "The Circuit," Electronic News, 45(45) (Nov. 8, 1999), 20.

Feng Bao, et al., "Design of portable mobile devices based e-payment system and e-ticketing system with digital signature," 2001 International Conferences on Info-Tech and Info-Net. Proceedings (Cat. No. 01 EX479), Beijing, China, 2001, pp. 7-12 vol. 6, doi:10.1109/ICII.2001.982996. (Year: 2001).

Freescale Semicondutor, Inc., "Freescale Events," see ZigBee Open House Event, Aug. 18, 2004, 6 pgs., archived at https://web.archive.org/web/20040909082726/https://www.freescale.com/webapp/sps/site/overview.jsp?nodeId=02XPgQ7JgbBqJQ#zigbee_openhouse_04.

Freescale Semiconductor, Inc., "Overview," ZigBee General Information, at least as early as Aug. 17, 2004, 1 pg., archived at https://web.archive.org/web/20040817210006/http:/www.freescale.com/webapp/sps/site/overview.jsp? nodeId=02XPgQhHPRjdyB37087725.

Freescale Semiconductor, Inc., "ZigBeeTM," Freescale Semiconductor Wireless Standards, at least as early as Aug. 18, 2004, 2 pgs., archived at https://web.archive.org/web/20040818075046/http:/www.freescale.com/webapp/sps/site/overview.jsp? nodeId=02XPgQhHPRjdyB.

Freescale Semiconductor, Inc., "ZigBeeTM," Freescale Semiconductor Wireless Standards, at least as early as Jun. 11, 2004, 2 pgs., archived at https://web.archive.org/web/20040611051834/http:/e-www.motorola.com/webapp/sps/site/overview.jsp? nodeId=02XPgQhHPRjdyB.

Freescale Semiconductor, Inc., "Freescale's ZigBeeTM-ready Platform Wins Sensors Magazine Best of Sensors Expo Award," Freescale Semiconductor Wireless, at least as early as Aug. 17, 2004, 1 pg., archived at https://web.archive.org/web/20040817203409mp_/http:/www.freescale.com/webapp/sps/site/overview.jsp?nodeId=02XPgQ6988.

Freescale Semiconductor, Inc., "ZigBee Alliance Successfully Concludes First Multi-node Network Test," press release, Jul. 6, 2004, 2 pgs., archived at https://web.archive.org/web/20040717113733/http:/www.zigbee.org/documents/First-Multi-Node_Testing_FINAL_000.pdf.

Freescale Semiconductor, Inc., "ZigBeeTM Technology from Freescale," Freescale Semiconductor, Inc. white paper, 2004, 4 pgs., archived at https://web.archive.org/web/20050513024652/http:/www.freescale.com/files/wireless comm/doc/brochure/BRZIGBEETECH.pdf.

Freescale Semiconductor, Inc., "ZRP-1 : ZigBee-ready Platform," at least as early as Oct. 19, 2005, 6 pgs., archived at https://web.archive.org/web/20051019122919/http://www.freescale.com/webapp/sps/site/prod_summary.jsp?code=ZRP-1 &nodeId=02XPgQhCQ6m6cy7103.

Freescale Semiconductor, Inc., M68HC08 microcontroller ordering web page, at least as early as Aug. 17, 2004, 5 pgs., archived at https://web.archive.org/web/20040817014804/http:/www.freescale.com/webapp/sps/site/taxonomy.jsp? NodeId=01 624684498634.

Giobbi, Specification of U.S. Appl. No. 60/824,758, filed Sep. 6, 2006, all pages.

Govindan et al. "Real Time Security Management Using RFID, Biometric and Smart Messages." 2009 3rd International Conference on Anti-Counterfeiting, Security, and Identification in Communication, Aug. 20, 2009, pp. 282-285.

Gralla, "How the Internet works," Millennium Edition, 1999, Que Corporation, Indianapolis, IN, all pages.

Hendron, "File Security, Keychains, Encryptioin, and More with Mac OS X (10.3+)" Apr. 4, 2005, downloaded from http://www.johnhendron.net/documents/OSX_Security.pdf on or before May 3, 2012, 30 pgs.

Hester et al., "neuRFon(TM) Netform: A Self-Organizing Wireless Sensor Network", Oct. 14, 2002, Proceedings of the Eleventh International Conference on Computer Communications and Networks, pp. 364-369.

Honkanen et al, "Low End Extension for Bluetooth", Sep. 19, 2004, Proceedings of the 2004 IEEE Radio and Wireless Conference, Atlanta, GA, pp. 199-202.

IBM Corporation, "Tadlys' Bluetooth Wireless Local Network for Hotspots," Wireless e-business, at least as early as May 6, 2004, 2 pgs., archived at https://web.archive.org/web/20040508123915/http://www.tadlys.com/media/downloads/Hotspots%20PVDEE01006-3.pdf.

IEEE Computer Society, "IEEE Std 802.15.4 (Trade Mark)—Part 15.4: Wireless Medium Access Control (MAC) and Physical Layer (PHY) Specifications for Low-Rate Wireless Personal Area Networks (LR-WPANs)," The Institute of electrical and Electronics Engineers, Inc., New York, NY, Oct. 1, 2003, 679 pgs.

IEEE, "IEEE 802.15 WPANTM Task Group 4 (TG4)" exemplary web page, Aug. 24, 2004, 2 pgs., archived at https://web.archive.org/web/20040824085452/http:/www.ieee802.org/15/pub/TG4.html.

International Search Report and Written Opinion for International Application No. PCT/US04/38124, mailed Apr. 7, 2005, 10 pgs.

International Search Report and Written Opinion for International Application No. PCT/US05/00349, mailed Mar. 19, 2008, 10 pgs.

International Search Report and Written Opinion for International Application No. PCT/US05/07535, mailed Dec. 6, 2005, 6 pgs.

International Search Report and Written Opinion for International Application No. PCT/US05/43447, mailed Feb. 22, 2007, 7 pgs.

(56) References Cited

OTHER PUBLICATIONS

International Search Report and Written Opinion for International Application No. PCT/US05/46843, mailed Mar. 1, 2007, 10 pgs.
International Search Report and Written Opinion for International Application No. PCT/US07/11102, mailed Oct. 3, 2008, 11 pgs.
International Search Report and Written Opinion for International Application No. PCT/US07/11103, mailed Apr. 23, 2008, 9 pgs.
International Search Report and Written Opinion for International Application No. PCT/US07/11104, mailed Jun. 26, 2008, 9 pgs.
International Search Report and Written Opinion for International Application No. PCT/US07/11105, mailed Oct. 20, 2008, 10 pgs.
International Search Report and Written Opinion for International Application No. PCT/US08/83060, mailed Dec. 29, 2008, 9 pgs.
International Search Report and Written Opinion for International Application No. PCT/US08/87835, mailed Feb. 11, 2009, 8 pgs.
International Search Report and Written Opinion for International Application No. PCT/US09/34095, mailed Mar. 25, 2009, 11 pgs.
International Search Report and Written Opinion for International Application No. PCT/US2009/039943, mailed Jun. 1, 2009, 9 pgs.
International Search Report and Written Opinion for International Application No. PCT/US2014/037609, mailed Dec. 9, 2014, 13 pgs.
International Search Report received for PCT Patent Application No. PCT/US2001/049916, mailed on Apr. 25, 2002, 1 page.
Jeyaprakash et al., "Secured Smart Card Using Palm Vein Biometric On-Card-Process," 2008 International Conference on Convergence and Hybrid Information Technology, 2008, pp. 548-551.
Jonker et al., "Digital rights management in consumer electronics products," IEEE Signal Processing Magazine, vol. 21, No. 2, pp. 82-91, Mar. 2004, doi: 10.1109/MSP.2004.1276116.
Katz et al., "Smart Cards and Biometrics in Privacy-Sensitive Secure Personal Identification System," May 2002, Smart Card Alliance, p. 1-29.
Kontzer, "Thomson Bets on Smart Cards for Video Encryption," www.informationweek.com, Jun. 7, 2001, 1 pg.
Korzeniowski, "First Intelligent, Wireless Consumer Devices About to Hit Market," TechNewsWorid, Jul. 28, 2004, 3 pgs., archived at https://web.archive.org/web/20040821061130/http:/www.technewsworid.com/story/35376.html%20com/.
Kuhn et al., Introduction to Public Key Technology and the Federal PKI Infrastructure, Feb. 26, 2001, National Institute of Standards and Technology, 54 pgs.
Labrou et al., "Wireless Wallet," Proceedings of the First Annual International Conference on Mobile and Ubiquitous Systems: Networking and Services (MobiQuitos '04), IEEE, Aug. 22-26, 2004, 10 pgs.
Lake, "Downloading for Dollars: Who said buying music off the Net would be easy?" Sound & Vision, Nov. 2000, pp. 137-138.
Lee et al., "Effects of dielectric superstrates on a two-layer electromagnetically coupled patch antenna," Digest on Antennas and Propagation Society International Symposium, 1989, pp. 620-623 vol. 2, doi: 10.1109/APS.1989.134763.
Lewis, "Sony and Visa in On-Line Entertainment Venture," New York Times, vol. 145, Thurs. Ed., Nov. 16, 1995, 1 pg-.
Liu et al., "A Practical Guide to Biometric Security Technology," IT Pro, vol. 3, No. 1, Jan./Feb. 2001, pp. 27-32.
Lockton et al., RFID: The next serious threat to privacy, Ethics and Information Technology (2005) 7:221-231 (Year: 2006).
Machine translation of JPH10049604, 27 pages.
Tadlys Ltd., "Wireless Museum Information," at least as early as Dec. 12, 2005, 2 pgs., archived at https://web.archive.org/web/20051212162456/http://www.tadlys.com/media/downloads/Tadlys_wireless_museum_network.pdf.
Tadlys Ltd., "Corporate Systems," at least as early as Nov. 1, 2004, 2 pgs., archived at https://web.archive.org/web/20041101095441/http://www.tadlys.com/media/downloads/Corporate_network.pdf.
Thomson Multimedia, "Thomson multimedia unveils copy protection proposal designed to provide additional laye of digital content security," retrieved from www.thompson-multimedia.com/gb/06/c01/010530.htm on Mar. 4, 2002, May 30, 2001, 2 pgs.
Thongthammachart et al., "Bluetooth Enables In-door Mobile Location Services," Proceedings of the 57th IEEE Semiannual Vehicular Technology Conference, Apr. 22-25, 2003, 5 pgs.
University of Birmingham, "PRISM: Probabilistic Symbolic Model Checker," at least as early as Aug. 3, 2004, 3 pgs., archived at https://web.archive.org/web/20040803193058/http://www.cs.bham.ac.uk/~dxp/prism/casestudies/index.html.
Unixhelp, "Whal is a file?" Apr. 30, 1998, retrieved from unixhelp.ed.ac.uk/editors/whatisafile.html accessed Mar. 11, 2010 via http://waybackmachine.org/19980615000000*/http://unixhelp.ed.ac.uk/editors/whatisafile.html on Mar. 11, 2011, 1 pg.
Vainio, "Bluetoolh Security," Helsinki University of Technology, May 25, 2000, 17 pgs.
Van Winkle, "Bluetooth: The King of Connectivity," Laptop Buyer's Guide and Handbook, Jan. 2000, pp. 148-153.
Wade, "Using Fingerprints to Make Payments at POS Slowly Gaining Popularity," Credit Union Journal, International Biometric Group, Apr. 21, 2003, retrieved from http://www.biometricgroup.com/in_the_news/04.21.03.html on Jan. 7, 2007, 3 pgs.
Wallace, "The Internet Unplugged," InformationWeek, vol. 765, No. 22, Dec. 13, 1999, pp. 22-24.
Weber, "In the Age of Napster, Protecting Copyright is a Digital Arms Race," Wall Street Journal, Eastern ed., Jul. 24, 2000, p. B1.
Weissman, "Indoor Location," Tadlys Ltd. white paper, at least as early as Oct. 31, 2004, 15 pgs., archived at https://web.archive.org/web/20041031125859/http:/www.tadlys.com/media/downloads/Indoors_Location_Systems.pdf.
White, "How computers Work," Millennium Edition, 1999, Que Corporation, Indianapolis, IN, all pages.
Yoshida, "Content Protection Plan Targets Wireless Home Networks," EE Times, Jan. 11, 2002, retrieved from www.eetimes.com/story/OEG20020111S0060 on Mar. 4, 2002, 2 pgs.
Zhang et al., "A User-Centric M-Payment Solution," The ISG-Smart Card Centre and the Information Security Group, Royal Holloway, University of London, Egham, Surrey, TW20 0EX, UK, 2005, 8 pgs.
Zigbee Alliance, "The ZigBeeTM Buzz Is Growing: New Low-Power Wireless Standard Opens Powerful Possibilities," Electronic Design, Jan. 12, 2004, 12 pgs., archived at https://web.archive.org/web/20040411172015/http:/www.elecdesign.com/Files/29/7186/7186_01.pdf.
Zigbee Alliance, "Welcome to the ZigBeeTM Alliance," exemplary web page, at least as early as Sep. 24, 2004, 2 pgs., archived at https://web.archive.org/web/20040924045517/http://zigbee.org/.
Zigbee Alliance, "ZigBee Specification," ZigBee Document 053474r06, Version 1.0, Dec. 14, 2004, 378 pgs.
Zigbee Alliance, "ZigBeeTM Positioned to Drive Wireless Networking in Building Automation, Industrial and Residential Control and Sensors Markets in 2004," press release, Feb. 17, 2004, 3 pgs., archived at https://web.archive.org/web/20040423220244/http:/www.zigbee.org/documents/04036r5ZB_MWG-Momentum-Release_FINAL.pdf.
"How to find the serial number on TP-Link devices," https://www.tp-link.com/us/support/faq/503/ (last visited Apr. 15, 2024), 3 pgs.
Google Pixel Serial Number Guide, HomeServe webpage, https://www.homeserve.com/en-us/customers/find-serial-numberdevice-type/google/, 3 pgs.
NPL Search Terms (Year: 2024).
Product Identification Codes, https://www.uc.edu/content/dam/uc/ce/docs/OLLI/Page%20Content/PRODUCT%20IDENTIFICATION%20CODES%20BAR%20QR.pdf, last visited Apr. 19, 2024, 88 pgs.
Specification of the Bluetooth System, Wireless Connections Made Easy, v 1.0 B, Dec. 1, 1999, 440 pgs., Dec. 1, 1999.
UK IT Security Evaluation and Certification Scheme, UK IT Security Evaluation and Certification Scheme, Certification Report No. P165, Sony FeliCa Contactless Smart Card, Issue 1.0, Mar. 2002, 27 pgs., Mar. 1, 2002.
Adams, "Designing with 802.15.4 and Zigbee," presented at Industrial Wireless Applications Summit, San Diego, California, Mar. 9, 2004, 22 pgs.
Adams, "Meet the ZigBee Standard," Sensors Online, Jun. 2003, 7 pgs., archived at https://web.archive.org/web/20031008191032/http:/sensorsmag.com/articles/0603/14/pf_main.shtml.

(56) References Cited

OTHER PUBLICATIONS

Adams, "Zigbee vital in industrial applications," EE Times, Jul. 29, 2003, 3 pgs., archived at https://web.archive.org/web/20031013062940/http:/www.eetimes.com/story/OEG20030727S0002.

Agourare et al., "Authentication and location control via RFID analysis," 2009 IEEE Conference on Emerging Technologies & Factory Automation, Sep. 1, 2009, 8 pgs.

Anonymous, "Applying Biometrics to Door Access," Security Magazine, Sep. 26, 2002, retrieved from http://www.securitymagazine.com/CDA/Articles/Technologies/3ae610eaa34d8010VgnVCM100000f932a8cO on Jan. 7, 2007, 5 pgs.

Anonymous, "BluePayz: A Seamless Payment Method Using Bluetooth-Enabled Mobile Phones," IP.com Publication Date 2003—Jun. 20, 2003, https://priorart.ip.com/1 PCOM/000015495 (Year: 2003).

Anonymous, "Firecrest Shows Flow Truly Commercially-Minded Companies Will Exploit the Internet," Computergram International, Jan. 18, 1996, 2 pgs.

Anonymous, "IEEE 802.15.4-2006—Wikipedia, the free encyclopedia," Wikipedia, last modified Mar. 21, 2009, retrieved from http://en.wikipedia.org/wiki/IEEE_802.15.4-2006 on Apr. 30, 2009, 5 pgs.

Antonoff, "Visiting Video Valley," Sound & Vision, Nov. 2001, pp. 116, 118-119.

Apple et aL, "Smart Card Setup Guide," 2006, downloaded from http://manuals.info.apple.com/en_US/Smart_Card_Setup_Guide.pdf on or before May 3, 2012, 16 pgs.

Balanis, "Antenna Theory: A Review," Jan. 1992, Proceedings of the IEEE, vol. 80, No. 1, p. 13.

Beaufour, "Personal Servers as Digital Keys," Proceedings of the Second IEEE Annual Conference on Pervasive Computing and Communications (PERCOM'04), Mar. 14-17, 2004, pp. 319-328.

Biopay, LLC, "Frequently Asked Questions (FAQs) About BioPay," retrieved from http://www.biopay.com/faqs-lowes.asp on Jan. 7, 2007, 5 pgs.

Blip Systems, "Mar. 8, 2004—Bluetooth at the office?" at least as early as Oct. 11, 2004, archived at https://web.archive.org/web/20041011094320/http:/www.blipsystems.com/Default.asp? ID=16&M=News&PID=25&NewsID=9.

Blip Systems, "BlipManager," at least as early as May 17, 2004, 1 pg., archived at https://web.archive.org/web/20040517050728/http:/www.blipsystems.com/Default.asp?ID=11.

Blip Systems, "BlipMobility," at least as early as Apr. 7, 2004, archived at https://web. archive. org/web/20040407212934/http:/www. blipsystems. com/Default.asp?ID=1 18.

Blip Systems, "BlipNet API," at least as early as May 18, 2004, 1 pg., archived at https://web.archive.org/web/20040518060132/http:/www.blipsystems.com/Default.asp?ID=92.

Blip Systems, "BlipNet Explore a wireless world . . . of great opportunities," brochure available Sep. 2002, 6 pgs., availabe online at https://web.archive.org/web/20031012184406/http:/www.blipsystems.com/products_blipnet.shtml.

Blip Systems, "BlipNet Technical Overview," Mar. 2003, 30 pgs., archived at https://web.archive.org/web/20031012184406/http:/www.blipsystems.com/products_blipnet.shtml.

Blip Systems, "BlipNode," at least as early as May 16, 2004, 1 pg., archived at https://web.archive.org/web/20040516001554/http:/www.blipsystems.com/Default.asp?ID=10.

Blip Systems, "BlipServer," at least as early as May 17, 2004, 1 pg., archived at https://web.archive.org/web/20040517044955/http:/www.blipsystems.com/Default.asp?ID=9.

Blip Systems, "Bluetooth Networks: Products: Bluetooth infracture," product description, at least as early as Oct. 2003, archived at https://web.archive.org/web/20031012184406/http:/www.blipsystems.com/products_blipnet.shtml.

Blip Systems, "Product Information—BlipNet—Presentation of BlipNet 1.0—A Bluetooth Access System," Aug. 2002, 2 pgs., archived at https://web.archive.org/web/20031012184406/http:/www.blipsystems.com/products_blipnet.shtml.

Blip Systems, BlipMobihty, at least as early as Apr. 7, 2004, archived at https://web. archive. org/web/20040407212934/http:/www. blipsystems.com/Default.asp?ID=1 18.

Blueproximity, "BlueProximity—Leave it—it's locked, come back, it's back too . . . " Aug. 26, 2007, retrieved from http://blueproximity.sourceforge.net/viahttp://www.archive.org/ on or before Oct. 11, 2011, 1 pg.

Bluetooth SIG, Inc. "Specification of the Bluetooth System," Version 1.2, Nov. 5, 2003, 82 pgs., archived at https://web.archive.org/web/20031119092849/http:/www.bluetooth.com/dev/spec.v12.asp.

Bluetooth SIG, Inc., "Bluetooth," www.bluetooth.com, Jun. 1, 2000, 8 pgs.

Bluetooth SIG, Inc., "Say Hello to Bluetooth," retrieved from www.bluetooth.com, at least as early as Jan. 14, 2005, 4 pgs.

Blum, "Digital Rights Management May Solve the Napster 'Problem,'" Technology Investor, Oct. 2000, pp. 24-27.

Bohrsatom et al., "Automatically unlock PC when entering proximity," Dec. 7, 2005, retrieved from http://salling.com/forums/viewtopic.php?t=3190 on or before Oct. 11, 2011, 3 pgs.

Brown, "Techniques for Privacy and Authentication in Personal Communication Systems," Personal Communications, IEEE, Aug. 1995, vol. 2, No. 4, pp. 6-10.

Callaway, "Wireless Sensor Networks: Architectures and Protocols," book description, Motorola Labs, Auerbach Publications, Aug. 26, 2003, 3 pgs., archived at https://web.archive.org/web/20031023101953/http:/www.crcpress.com/shopping cart/products/product detail.asp? sku=AU1823.

Callaway, Wireless Sensor Networks: Architectures and Protocols, Jan. 1, 2004, Auerbach Publications, 366 pgs.

Chen et al."On Enhancing Biometric Authentication with Data Protection." KES2000. Fourth International Conference on Knowledge-Based Intelligent Engineering Systems and Allied Technologies. Proceedings (Cat. No. 00TH8516), vol. 1, Aug. 1, 2000, pp. 249-252.

Chi et al., "Industrial Wireless Sensor Networking: A Market Dynamics Study," ON World, Jun. 28, 2004, 5 pgs., archived at https://web.archive.org/web/20040710182216/http:/onworld.com:80/html/industrialwirelesssensor.htm.

Cisco Systems, Inc., "Antenna Patterns and Their Meaning," 1992-2007, p. 10.

Costa, "Imation USB 2.0 Micro Hard Drive," Nov. 22, 2005, retrieved from http://www.pcmag.com/article2/0,2817,1892209,00.asp on or before Oct. 11, 2011, 2 pgs.

Dagan, "Power over Ethernet (PoE) Midspan—The Smart Path to Providign Power for IP Telephony," Product Manager, Systems, Aug. 2005, Power Dsine Inc., 28 pgs.

Dai et al., "Toward Blockchain-Based Accounting and Assurance," Journal of Information Systems, vol. 31, No. 3, Fal 2017, pp. 5-21.

Dai et al., Toward Blockchain-Based Accounting and Assurance, Journal of Information Systems, vol. 31, No. 3, Fai 2017, pp. 5-21.

David et al., Security Issues for Contactless Smart Cards, Sep. 1, 1997, conference paper, available online at https://link.springer.com/chapter/10.1007/BFb0054029, 6 pgs.

Debow, "Credit/Debit Debuts in Midwest Smart Card Test," Computers in Banking, vol. 6, No. 11, Nov. 1989, pp. 10-13.

Dennis, "Digital Passports Need Not Infringe Civil Liberties," Newsbytes, NA, Dec. 2, 1999, 2 pgs.

Derfler, "How Networks Work," Bestseller Edition, 1996, Ziff-Davis Press, Emeryville, CA, all pages.

Disclosed Anonymously (Method and Apparatus for Mobile Identity Authentication)., An IP.com Prior Art Database Technical IP.com No. IPCDM000194545D., IP.com Electronic Publication Date: Mar. 29, 2010 (Year: 2010).

Duflot et al., "A Formal Analysis of Bluetooth Device Discovery," presented at the 1st International Symposium on Leveraging Applications of Formal Methods (ISOLA'04), Oct. 30-Nov. 2, 2004, Paphos, Cyprus, and published in the International Journal on Software Tools for Technology Transfer 8, pp. 621-632,16 pgs., https://doi.org/10.1007/sl0009-006-0014-x.

Dvorak, IEEE 802.15.4 and Zigbee Overview, Sep. 27, 2005, Motorola, 26 pgs.

(56) References Cited

OTHER PUBLICATIONS

Emiconductor Wireless Standards, at least as early as Aug. 18, 2004, 2 pgs., archived at https://web.archive.org/web/20040818075046/http:/www.freescale.com/webapp/sps/site/overview.jsp?nodeId=02XPgQhHPRjdyB.
Eshed, "Bluetooth Wireless Technology Application for the Retail Market," published at www.tadlys.com on May 2001, 8 pgs.
KR-20070060937—machine translation (Year: 2007).
ADT. "Apps and Data to Go on USB Drives", Jul. 2005. Retrieved from <https://adtmag.com/articles/2005/07/27/apps-and-data-to-go-on-usb-drives.aspx?p=1>. (Year: 2005).
Nadel, Brian. "SanDisk Cruzer Profile review: SanDisk Cruzer Profile", Apr. 2005. Retrieved from <https://www.cnet.com/reviews/sandisk-cruzer-profile-review/>. (Year: 2005).
Sever, Gil. "Don't get out-smarted by smart devices", Aug. 2007. Retrieved from <https://www.scworld.com/perspective/dont-get-out-smarted-by-smart-devices>. (Year: 2007).

* cited by examiner

PROXIMITY-BASED SYSTEM FOR OBJECT TRACKING AND AUTOMATIC APPLICATION INITIALIZATION

CROSS REFERENCE TO RELATED APPLICATIONS

This application is a continuation of and claims priority to U.S. application Ser. No. 17/372,189, filed Jul. 9, 2021, titled "Proximity-Based System for Object Tracking and Automatic Application Initialization," which is a continuation of and claims priority to U.S. application Ser. No. 16/247,111, filed Jan. 14, 2019, titled "Proximity-Based System for Object Tracking and Automatic Application Initialization," which is a continuation of and claims priority to U.S. application Ser. No. 14/981,607, filed Dec. 28, 2015, titled "Proximity-Based System for Object Tracking and Automatic Application Initialization," which claims the benefit, under 35 U.S.C. § 120, of U.S. patent application Ser. No. 13/401,702, filed Feb. 21, 2012, titled "Proximity-Based System for Object Tracking and Automatic Application Initialization," which claims the benefit, under 35 U.S.C. § 119 (e), of U.S. Provisional Application No. 61/445,035, filed Feb. 21, 2011, titled "ProxAccess and ProxNet Design and Implementation," the entire contents of all of which are incorporated herein by reference.

Applicants hereby notify the USPTO that the claims of the present application are different from those of the aforementioned related applications. Therefore, Applicant rescinds any disclaimer of claim scope made in the parent application or any other predecessor application in relation to the present application. The Examiner is therefore advised that any such disclaimer and the cited reference that it was made to avoid may need to be revisited at this time. Furthermore, the Examiner is also reminded that any disclaimer made in the present application should not be read into or against the parent application, the grandparent application or any other related application.

BACKGROUND OF THE INVENTION

1. Field of Art

This disclosure generally relates to the field of radio frequency identification (RFID) and electronic authentication, and more specifically, to systems and methods for object tracking and automatic and secure authentication of users.

2. Description of the Related Art

Optimizing patient care is an ever-changing and challenging endeavor. Ensuring quality patient care that is safe, efficient and cost-effective is very important to patients, as well as healthcare providers. Conventional technologies used in the healthcare industry for aiding provider patient care, monitoring patient treatment, receiving and retrieving patient data and monitoring provider activity have not yet provided optimal features to meet these needs. Recently, software application systems have been developed in an attempt to improve patient care and provider performance.

Currently, many healthcare facilities utilize electronic software and applications to securely store and efficiently access private patient information. In many healthcare institutions, healthcare providers access patient electronic records with authorized entry into the healthcare software application system. In most conventional systems, providers are provided with a unique user name and password that they must enter into a system each time they need to access patient information. Further, when a healthcare provider is done accessing patient records, the healthcare provider must log out of the system to ensure that unauthorized use does not occur. The process of logging in and logging off each time may prove to be quite time-consuming given the number of patients a provider visits in a given day.

Another problem for many healthcare facilities is making sure that equipment is deployed in a manner that maximizes their usage and availability. For example, in many hospitals the location of equipment is not tracked and monitored other than during an annual equipment inventory. Thus, healthcare providers may not be aware of the precise location of equipment or know when equipment is currently in use. Thus, conventional methods provided limited ability to track the location of equipment.

BRIEF SUMMARY OF THE INVENTION

A system and method provides for one or more of tracking of an object and automatic access to applications or data while maintaining application or data security. A portable physical device, referred to herein as a Personal Digital Key or "PDK", stores one or more profiles uniquely associated with a user in a memory. In one embodiment, one of the profiles is a biometric profile that is acquired in a secure trusted process and is uniquely associated with a user authorized to use the PDK and associated with the PDK. A reader wirelessly communicates with the PDK and receives a profile from the PDK. A computing device is coupled to the reader and displays data on a display device responsive to receiving data associated with the profile from the reader. Additionally, an auto login sever is coupled to the computing device and to the reader and the auto login server receives the profile from the reader and automatically launches, on the computing device, one or more applications associated with a user name identified by the profile.

In one embodiment, the reader acquires a biometric input from the user associated. The biometric input can be acquired by, for example, a fingerprint scan, iris scan, retinal scan, palm scan, face scan, DNA analysis, signature analysis, voice analysis or any other input mechanism that provides physical or behavioral characteristics uniquely associated with the individual. The reader compares the biometric profile received from the PDK to the biometric input acquired from the user to determine if an application should be launched or if data access is authorized.

A tracking server is configured to communicate with the reader. The tracking server is configured to track and log information of the PDK associated with the object. The information is received from the reader. A computing device is configured to communicate with the reader and the tracking server, the computing device configured to display data on a display device responsive to receiving the information from the reader.

A method for tracking an object includes receiving a search query. The search query includes at least one identifier associated with the object. The object is carrying a personal digital key (PDK) and the PDK is associated with the object and wirelessly communicating with a receiver/decoder circuit (RDC). The method also includes retrieving information from a tracking server. The information includes information of the PDK associated with the object. The method also includes enabling the user to locate the object based at least in part on the information retrieved from the tracking server.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

Figure 1:
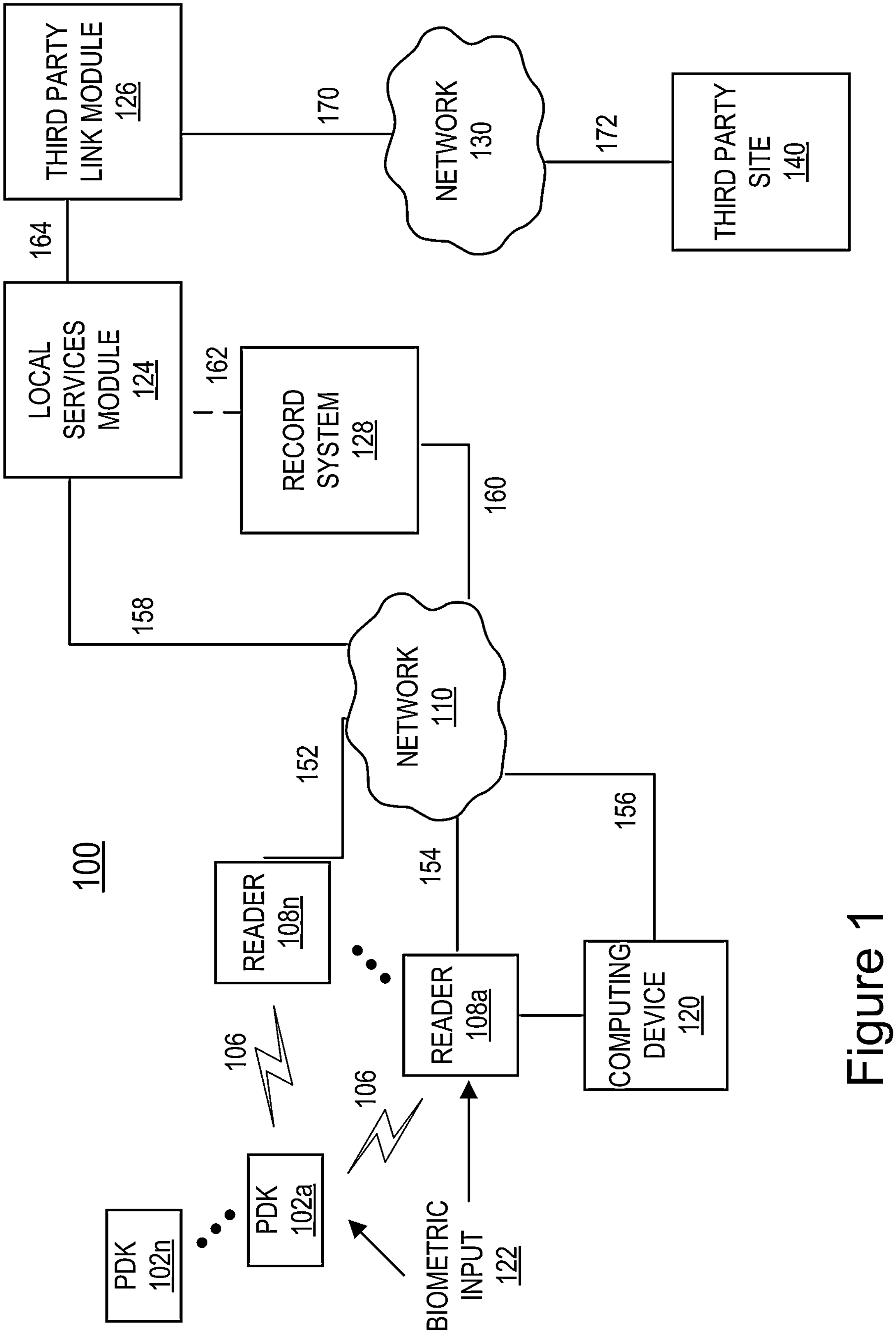
FIG. 1 is a block diagram illustrating a system for securely authenticating an individual for accessing data or one or more applications in accordance with the present invention.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

A system and method for providing automatic access to applications or data while maintaining application or data security are described. In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The specification also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present embodiment of invention is not described with reference to a particular programming language. It will be appreciated that a variety of programming languages may be used to implement the teachings of the invention as described herein.

FIG. 1 is a high level block diagram illustrating a system for securely authenticating an individual for accessing data or one or more applications. The system 100 comprises a Personal Digital Key (PDK) 102, a Reader 108, a network 110, a computing device 120, a local services module 124, a third party link module 126, a record system 128, a network 130 and a third party site 140. The Reader 108 is coupled to PDK 102 by a wireless link 106 and coupled to a network 110 by either a wired or wireless link represented by lines 152 and 154. The Reader 108 is also adapted to receive a biometric input 122 from a user and is capable of displaying status to a user. The PDK 102 is also adapted to receive biometric input 122 from a user. The network 110 couples the local services module 124 and third party link module 126 to the Reader 108. The network 110 also couples the local services module 124 and third party link module 126 to the record system 128 via signal lines 158 and 160. In alternative embodiments, different or additional external services, registries or databases (not shown) are coupled to the network 110. In another embodiment, the Reader 108 operates as a standalone device without a connection to the network 110. The network 130 couples the third party link module 126 to the third party site 140 and services provided by the third party site 140, such as pharmacy services, insurance services or lab services.

The system 100 addresses applications where it is important to ensure a specific individual is authorized to perform a given transaction. A transaction as used herein includes executing a purchase or financial dealing, enabling access to physical and/or digital items (e.g., logging into a computer system, launching applications or retrieving data), providing identification or personal information or executing other tasks where it is important to authenticate an individual for use. In one embodiment, the Reader 108 wirelessly receives information stored in the PDK 102 that uniquely identifies the PDK 102 and the individual carrying the PDK 102. In another embodiment, the Reader 108 also receives a biometric input 122 from the individual. For example, the Reader 108 receives a fingerprint, a retinal scan, an iris scan, a facial scan or any other suitable biometric input associated with the individual. In one embodiment, the PDK 102 receives the biometric input 122 from the individual. Based on the received information, the Reader 108 determines if the transaction should be authorized. Beneficially, the system 100 provides comprehensive authentication without the need for PINs or passwords. Moreover, personal biometric information need not be stored in any local or remote storage database and is only stored on the user's own PDK 102. Furthermore, in one embodiment, purchase transactions can be efficiently completed without requiring the use of physical credit cards, tokens or other user action beyond initiating the transaction.

The PDK 102 is a compact, portable uniquely identifiable wireless device typically carried by an individual or affixed to an object or device. The PDK 102 stores digital information in a tamper-proof format uniquely associating the PDK 102 with an individual. Example embodiments of PDKs are described in more detail in U.S. patent application Ser. No. 11/292,330, entitled "Personal Digital Key And Receiver/Decoder Circuit System And Method" filed on Nov. 30, 2005; U.S. patent application Ser. No. 11/620,581 entitled "Wireless Network Synchronization Of Cells And Client Devices On A Network" filed on Jan. 5, 2007; and U.S. patent application Ser. No. 11/620,577 entitled "Dynamic Real-Time Tiered Client Access" filed on Jan. 5, 2007, the entire contents of which are all incorporated herein by reference.

To establish the trust, credibility and confidence of the authentication system, information stored in the PDK 102 is acquired by a process that is trusted, audited and easily verified. The process is ensured by a trusted third-party system, referred to herein as a "Notary," that administers the acquisition and storage of information in the PDK 102 according to defined security protocols. In one embodiment, the Notary is a system and/or a trusted individual that witnesses the acquisition and storage either in person or remotely. In another embodiment, the Notary comprises trusted hardware that administers the initialization process by an automated system. Thus, once initialized by the trusted process, the PDK 102 can prove that the information it stores is that of the individual. Example embodiments of the initialization process are described in U.S. patent application Ser. No. 11/744,832 to John Giobbi, et al., entitled "Personal Digital Key Initialization and Registration For Secure Transaction" filed on May 5, 2007, the entire contents of which are incorporated herein by reference.

The Reader 108 wirelessly communicates with the PDK 102 when the PDK 102 is within a proximity zone of the Reader 108. The proximity zone can be, for example, several meters in radius and can be adjusted dynamically by the Reader 108. Thus, in contrast to many conventional radio frequency identification (RFID) devices, the Reader 108 is able to detect and communicate with the PDK 102 without requiring an individual using, or associated with the PDK 102, to remove the PDK 102 from his/her pocket, wallet, purse, etc. Generally, the Reader 108 receives uniquely identifying information from the PDK 102 and initiates an authentication process for the individual carrying the PDK 102. In one embodiment, the Reader 108 is adapted to receive a biometric input 122 from the individual. The biometric input 122 comprises a representation of physical or behavioral characteristics unique to the individual. For example, the biometric input 122 can include a fingerprint, a palm print, a retinal scan, an iris scan, a photograph, a signature, a voice sample or any other biometric information such as DNA, RNA or their derivatives that can uniquely identify the individual. The Reader 108 compares the biometric input 122 to information received from the PDK 102 to determine if a transaction should be authorized. In one embodiment, the biometric input 122 can be obtained by a biometric reader 470 (FIG. 4) on the PDK 102 and transmitted to the Reader 108 for authentication. In another embodiment, some or all of the authentication process can be performed by the PDK 102 instead of the Reader 108.

Figure 2:
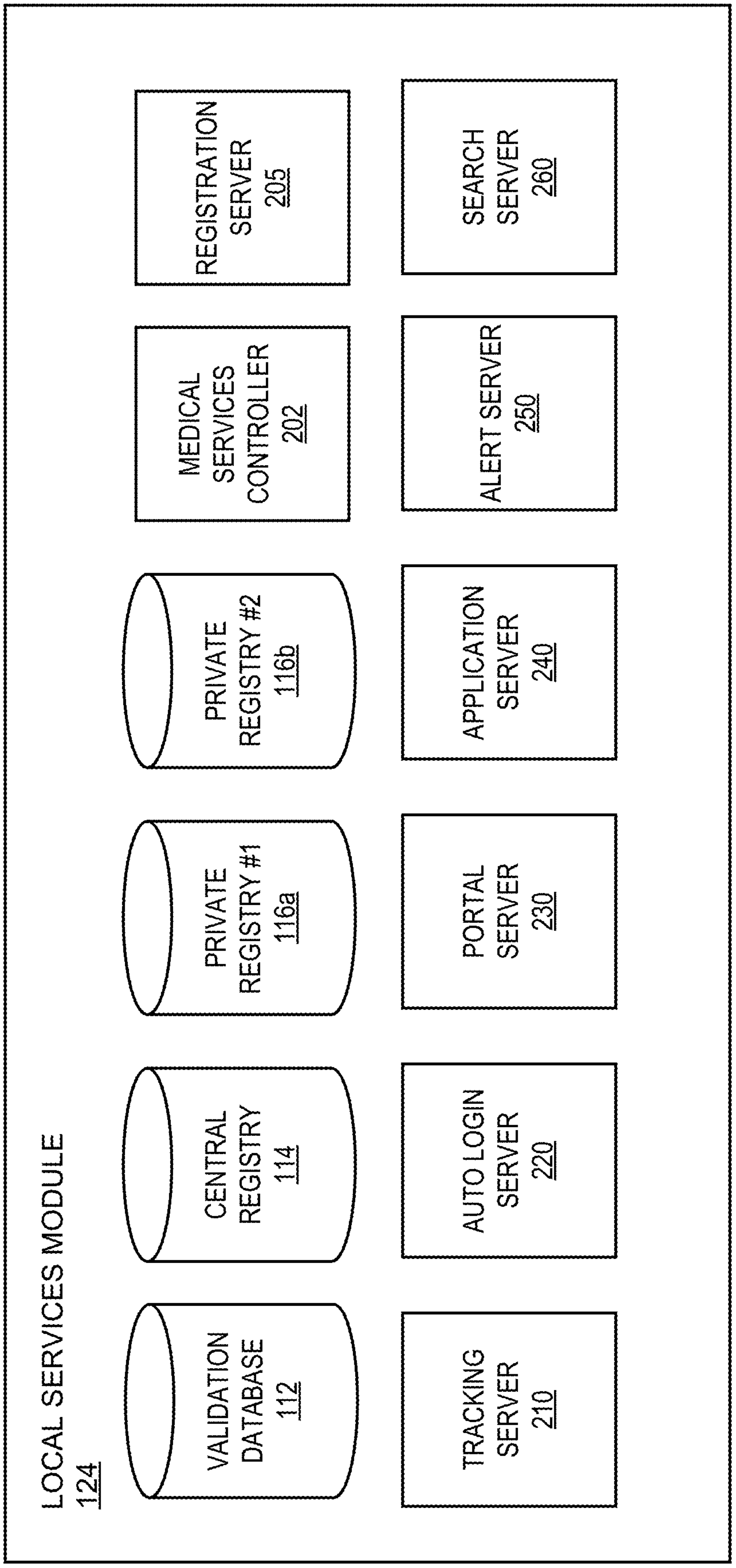
FIG. 2 is a block diagram illustrating one embodiment of a local services module in accordance with the present invention.

The Reader 108 is further communicatively coupled to the network 110 in order to receive and/or transmit information to remote databases for remote authentication. In an alternative embodiment, the Reader 108 includes a non-volatile data storage that can be synchronized with one or more remote databases 112 or registries 114, 116*a*, 116*b* (FIG. 2). Such an embodiment alleviates the need for a continuous connection to the network 110 and allows the Reader 108 to operate in a standalone mode and for the local data storage to be updated when a connection is available. For example, a standalone Reader 108 can periodically download updated registry entries and perform authentication locally without any remote lookup.

The network 110 provides communication between the Reader 108 and the computing device 120, local services module 124, and third party link module 126. For example, a communication channel 156 couples the computing device 120 to the network 110. For example, the communication channel 156 is a wired or wireless connection. In alternative embodiments, one or more of these connections may not be present or different or additional network connections may be present. In one embodiment, the network 110 uses standard communications technologies and/or protocols. Thus, the network 110 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

Similarly, the network 130 provides communication between the local services module 124 and third party site 140. In alternative embodiments, one or more of these connections may not be present or different or additional network connections may be present. In one embodiment, the network 130 uses standard communications technologies and/or protocols. Thus, the network 130 can include links using technologies such as Ethernet, 802.11, 802.16, integrated services digital network (ISDN), digital subscriber line (DSL), asynchronous transfer mode (ATM), etc. Similarly, the networking protocols used on the network 110 can include the transmission control protocol/Internet protocol (TCP/IP), the hypertext transport protocol (HTTP), the simple mail transfer protocol (SMTP), the file transfer protocol (FTP), etc. The data exchanged over the network 110 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

FIG. 2 is a block diagram illustrating a local services module 124, which includes one or more external databases including a validation database 112, a Central Registry 114 and one or more private registries 116*a*, 116*b*. The local services module 124 also includes a medical services controller 202, a registration server 205, a tracking server 210, an auto login server 220, a portal server 230, an application server 240, an alert server 250 and a search server 260.

The validation database 112 stores additional information that may be used for authorizing a transaction to be processed at the Reader 108. For example, in purchase transactions, the validation database 112 is a credit card validation database that is separate from the merchant providing the sale. Alternatively, a different database may be used to validate different types of purchasing means such as a debit card, ATM card, or bank account number. As another example in healthcare systems, the validation database 112 is a medical record number validation database that separate from the healthcare institution providing the patient care, which provides confirmation of the patient's identification.

The registries 114, 116*a*, 116*b* are securely-accessible databases coupled to the network 110 that store, among other items, PDK, Notary, and Reader information. In one embodiment, the registries 114, 116*a*, 116*b* do not store biometric information. In an alternative embodiment, the registries 114, 116*a*, 116*b* store biometric information in an encoded format that can only be recovered using an algorithm or encoding key stored in the PDK 102. Information stored in the registries 114, 116*a*, 116*b* can be accessed by the Reader 108 via the network 110 for use in the authentication process. There are two basic types of registries 114, 116*a*, 116*b* illustrated: private registries 116*a*, 116*b* and the Central Registry 114. Private registries 116*a*, 116*b* are generally established and administered by their controlling entities (e.g., a health care provider, business authority, or other entity administering authentication). Private registries 116*a*, 116*b* can be custom configured to meet the specialized and independent needs of each controlling entity. The Central Registry 114 is a single highly-secured, centrally-located database administered by a trusted third-party organization.

In one embodiment, all PDKs 102 are registered with the Central Registry 114 and may be optionally registered with one or more selected private registries 116*a*, 116*b*. In alternative embodiments, a different number or different types of registries 114, 116*a*, 116*b* may be coupled to the network 110.

In one embodiment, a registry 114, 116 or the database 112 includes one or more records. A record includes login information associated with one or more applications. For example, the record includes a PDK ID 312, an application identifier, an application username and an application password. When the PDK 102 is identified by a Reader, data from the registry profile is communicated to the local services module 124 and used to allow a user to login or access an application using the data stored in the registry profile. In one embodiment, different records in the registry 114, 116 or database 112 are encrypted using a registry key that is also stored in the PDK 102 to prevent access to a record without the PDK 102. One embodiment of launching, or accessing, an application using a registry profile is further described below in conjunction with FIGS. 18-20.

The medical services controller 202 enables communication between the servers and modules of the local services module 124 and third party link module 126 with the computing device 120. In one embodiment, the medical services controller 202 receives information and requests from the computing device 120 via the network 110. In another embodiment, the medical services controller 202 coordinates the operation of the various servers and modules of the local services module 124 and third party link module 126. For example, when a patient registration request is received from the Reader 108, the medical services controller 202 routes the request to the registration server 205 and forwards registration confirmation to the appropriate destination, such as the computing device 120.

The registration server 205 automates the process of registering new patients and ensures that a patient does not need to register more than once. In one embodiment, the registration server 205 resides in the local services module 124, which is coupled to the network via signal line 158. In one embodiment, the registration server 205 is coupled to the validation database 112, central registry 114 and private registries 116*a*, 116*b*. The registration server 205 receives patient registration requests from Readers 108 via the network 110 and sends information to the computing device 120 also via the network 110.

The tracking server 210 enables real-time tracking of individuals, equipment and supplies. In one embodiment, the tracking server 210 resides in the local services module 124, which is coupled to the network 110 via signal line 158. The tracking server 210 receives information from the Readers 108 and sends information back to the Readers 108 and PDK 102. One embodiment of the tracking server 210 is described in more detail below with reference to FIG. 15.

The auto login server 220 allows for automated logging in of a user into a computer system. In one embodiment, the user is a healthcare provider logging into a healthcare computer system. In one embodiment, the auto login server 220 resides in the local services module 124 and is coupled to the validation database 112, central registry 114 and private registries 116*a*, 116*b*. The auto login server receives login requests from the Readers 108 and sends login authorization to the computing device 120. One embodiment of the auto login server 220 is described in more detail below with reference to FIG. 17.

The portal server 230 exchanges data between the local services module 124 and one or more third party sites 140.

For example, the portal server 230 includes identifiers associated with one or more third party sites 140 to identify a third party site 140 and enable access to data maintained by the third party site 140. In one embodiment, the portal server 230 also modifies the format of data received from a third party site 140 to expedite use of the received data by another component, such as the application server 240 or a computing device 120 coupled to the local services module 124.

The application server 240 includes data that, when executed by a processor, implements one or more applications to provide one or more types of functionality. In one embodiment, the application server 240 is included in the local services module 124. Additionally, in one embodiment, the application server 240 communicates with one or more third party sites 140 via a signal line 164, which communicates with the third party link module 126, which connects to the network 130 via a communication channel 170, which communicates with the third party site 140 via a communication channel 172. This allows the application server 240 to communicate data from the third party site 140 to the computing device 120. One embodiment of the application server 240 is described in more detail below with reference to FIG. 24. Such third party services may include accessing a patient's virtual database records or insurance information or sending prescription requests to remote pharmacies. More detailed information describing the components and functions of these servers is described in more detail below.

The alert server 250 provides automatic updates and alerts for monitored patients or other entities. The alert server 250 receives information from Readers 108 and sends information to the computing device 120. In one embodiment, the alert server 250 resides in the local services module 124. In one embodiment, the alert server 250 receives data from the tracking server 210 to allow generation of updates or alerts based on the location of a PDK 102. In one embodiment, the alert server 250 is configured to receive data from an alert editor. In one embodiment, the data received from the alert editor includes alert identifiers and objects associated with the alert identifiers.

The search server 260 enables the user to search the tracking server 210 for one or more tracked items (e.g., users or assets) and request that the tracking server 210 generate or display one or more of a time and motion report, an audit report, a tracked items location, historic locations and an alert. In an alternative embodiment, the search server 260 and or its functionality are part of the tracking server 210.

Figure 3:
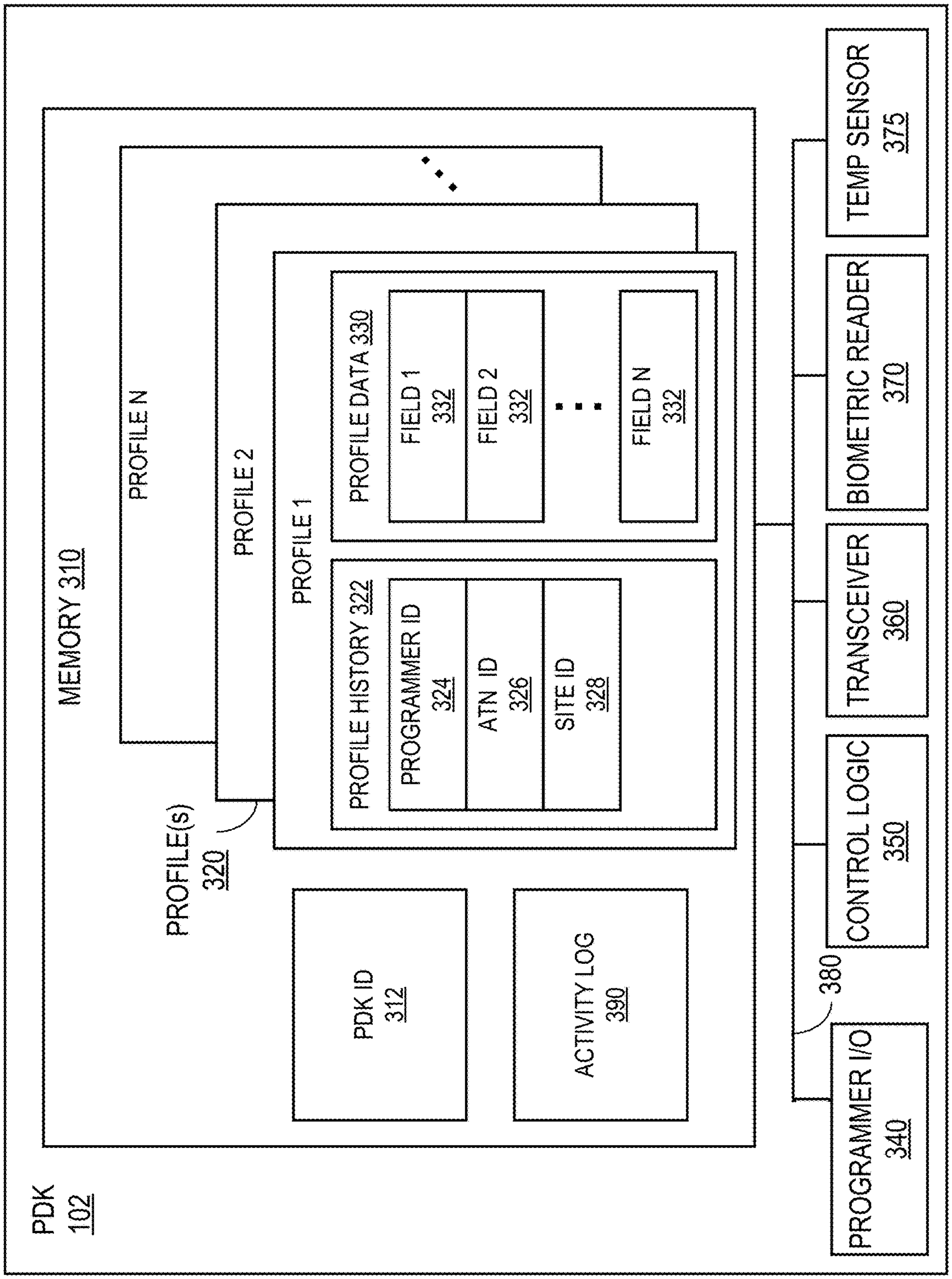
FIG. 3 is a block diagram illustrating one embodiment of a Personal Digital Key (PDK) in accordance with the present invention.

Turning now to FIG. 3, an example embodiment of a PDK 102 is illustrated. The PDK 102 comprises a memory 310, a programmer I/O 340, control logic 350, a transceiver 360, a biometric reader 370 and a temp sensor 375 coupled by a bus 380. The PDK 102 can be standalone as a portable, physical device or can be integrated into commonly carried items. For example, a PDK 102 can be integrated into a portable electronic device such as a cell phone, Personal Digital Assistant (PDA), or GPS unit, an employee identification tag or badge, clothing, or jewelry items such as watches, rings, necklaces or bracelets. In one embodiment, the PDK 102 can be, for example, about the size of a Subscriber Identity Module (SIM) card and be as small as a square inch in area or less. In another embodiment, the PDK 102 can be easily contained in a pocket, on a keychain, or in a wallet. In yet another embodiment, a PDK 102 can be integrated into a sticker, tag or other item attachable to various items or equipment. In other embodiments, the PDK 102 can be integrated into a clipboard, patient wristband or other patient identification tags or badges. In some embodiments, where the PDK 102 is attached to equipment for tracking purposes, the PDK 102 also includes a button or switch that can be activated or deactivated to indicate whether the equipment is in use.

The memory 310 can be a read-only memory, a once-programmable memory, a read/write memory or any combination of memory types including physical access secured and tamper-proof memories. The memory 310 typically stores a unique PDK ID 312, an activity log 390 and one or more profiles 320. The PDK ID 312 comprises a public section and a private section of information, each of which can be used for identification and authentication. In one embodiment, the PDK ID 312 is stored in a read-only format that cannot be changed subsequent to manufacture. The PDK ID 312 is used as an identifying feature of a PDK 102 and distinguishes between PDKs 102 in private 116 or Central 114 registry entries. In an alternative embodiment, the registries can identify a PDK 102 by a different ID than the PDK ID 412 stored in the PDK 102, or may use both the PDK ID 312 and the different ID in conjunction. The PDK ID 312 can also be used in basic PDK authentication to ensure that the PDK 102 is a valid device.

The activity log 390 stores information associated with various activities of the PDK. For example, if the PDK 102 is a patient's PDK, the activity log 390 stores information identifying the patient's location throughout various times. In one embodiment, the activity log 390 keeps track of each time a patient visits a healthcare facility or each time a doctor or nurse visits a department within the healthcare facility. In another embodiment, the activity log 390 stores the patient's location throughout various points as the patient is in the provider's facility. Similarly, the if PDK 102 is attached to a piece of equipment or a cart of supplies, the activity log 390 stores location information as well. In another embodiment, if the PDK 102 is that of a provider, the activity log 390 stores information associated with the provider's rounds, i.e. each time a provider visits a certain patient or uses a particular medical device. In some embodiments where the PDK is associated with a piece of equipment, the activity log 390 stores information regarding one or more of the equipment's usage, maintenance and calibration.

The profile fields 320 can be initially empty at the time of manufacture but can be written to by authorized individuals (e.g., a Notary) and/or hardware (e.g., a Programmer). In one embodiment, each profile 320 comprises a profile history 322 and profile data 330. Many different types of profiles 320 are possible. A biometric profile, for example, includes profile data 330 representing physical and/or behavioral information that can uniquely identify the PDK owner. A PDK 102 can store multiple biometric profiles, each comprising a different type of biometric information. In one embodiment, the biometric profile 320 comprises biometric information transformed by a mathematical operation, algorithm, or hash that represents the complete biometric information (e.g., a complete fingerprint scan). In one embodiment, a mathematical hash is a "one-way" operation such that there is no practical way to re-compute or recover the complete biometric information from the biometric profile. This both reduces the amount of data to be stored and adds an additional layer of protection to the user's personal biometric information. In one embodiment, the biometric profile is further encoded using an encoding key and/or algorithm that is stored with the biometric profile data. Then, for authentication, the biometric profile data and the encoding key and/or algorithm are passed to the Reader 108.

In one embodiment, the PDK 102 also stores one or more biometric profile "samples" associated with each biometric profile. The biometric profile sample is a subset of the complete profile that can be used for quick comparisons of biometric data. In one embodiment, the profile samples can be transmitted over a public communication channel or transmitted with reduced level of encryption while the full biometric profiles are only transmitted over secure channels. In the case of fingerprint authentication, for example, the biometric profile sample may represent only small portion area of the full fingerprint image. In another embodiment, the fingerprint profile sample is data that describes an arc of one or more lines of the fingerprint. In yet another embodiment, the fingerprint profile sample can be data representing color information of the fingerprint.

In another embodiment, the stored profiles 320 include a PIN profile that stores one or more PINs or passwords associated with the PDK owner. Here, the number or password stored in the PIN profile can be compared against an input provided by the user at the point of transaction to authenticate the user. In one embodiment, a PIN profile sample is also stored with the PIN profile that comprises a subset of the full PIN. For example, a PIN profile sample can be only the first two numbers of the PIN that can be used to quickly compare the stored PIN profile to a PIN obtained at the point of transaction.

In yet another embodiment, the PDK 102 stores a picture profile that includes one or more pictures of the PDK owner. In a picture profile authentication, the picture stored in the PDK 102 is transmitted to a display at the point of transaction to allow an administrator (e.g., a clerk or security guard) to confirm or reject the identity of the individual requesting the transaction. In another embodiment, an image is captured of the individual at the point of transaction and compared to the picture profile by an automated image analysis means. Furthermore, picture profiles could be used, for example, in place of conventional passports or drivers licenses to authenticate the identity of an individual and allow for remote identification of individuals. For example, a police officer following a vehicle could obtain an image and identity of the driver while still maintaining a safe distance from the vehicle. In the hospitality industry, a host could greet a guest at the door of a hotel, casino or restaurant and easily recognize the guest by obtaining the guest's picture profile as he/she enters. In healthcare, a doctor or nurse can ensure that he or she is administering the correct medication to the right patient by looking at the profile picture associated with that patient.

A registry or database profile typically stores information associating the user with a registry. The registry profile can be used to determine if the individual is associated with the controlling entity for that registry and if different types of transactions are authorized for the individual. A registry profile can further include additional user information for use with the registry. For example, a private registry profile associated with a particular merchant may include a credit card number that the user has selected as a default for that merchant. In one embodiment, a profile can further include spending limits that limits the amount of purchases a user can make with a particular vendor or using a particular profile.

A registry profile may include one or more service blocks identifying a registry 114, 116 or database 112 in the local services module 124 and identify a record within the identified registry 114, 116 or database 112. In one embodiment, the service block includes a registry identifier, a record identifier to specify a record within the identified registry and a registry key. In one embodiment, different records in the registry 114, 116 or database 112 are encrypted using registry key that is stored in the PDK 102 to prevent access to a record without the PDK 102. In one embodiment, one or more processes implemented by the control logic 350 are used to identify a service block within a registry profile, allowing access to specific service blocks. This also allows application of service block-specific security by making different service blocks independent of each other. One embodiment of launching, or accessing, an application using a registry profile is further described below in conjunction with FIGS. 18-21.

Additionally, a profile may include application specific information, allowing a registry profile to be used to launch or access an application and application specific information included in the registry profile or in another profile to be accessed by the application. This allows the PDK 102 to include data customizing operation of an application. For example, a patient of a healthcare facility may have a PDK 102 having a profile that stores the patient's medical records, allowing a computing device 120 to retrieve the patient's medical records when the PDK 102 communicates with a Reader 108 coupled to the computing device 120. As another example, a PDK 102 profile includes user preference data, allowing configuration of an application executed by a computing device 120 by communicating the user preference data from the PDK 102 to the computing device 120 via a Reader 108 coupled to the computing device 120. Hence, in addition to including data used for authentication or security, a PDK 102 may include profiles for customizing operation of applications or for storing data for subsequent access.

A profile can further include personal identification information such as name, address, phone number, etc., insurance information, credit/debit card information, or information regarding visited providers. This information can be useful for certain types of transactions. For example, patient office visits, a PDK 102 can automatically transmit address, insurance and billing information to the Reader 108 at the conclusion of the office visit.

Figure 25:
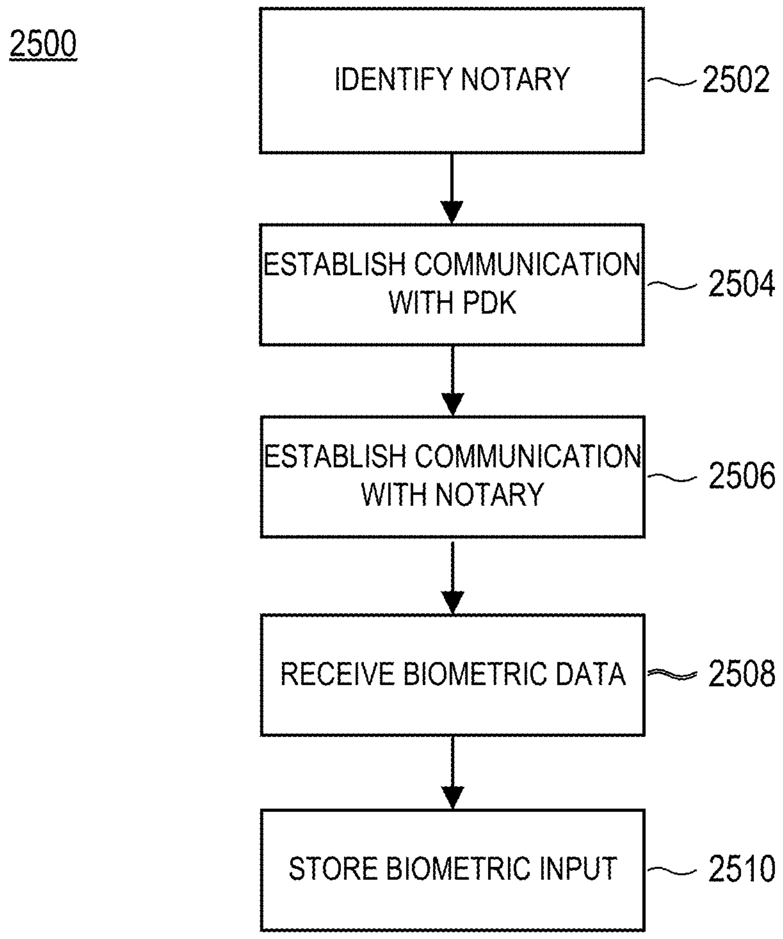
FIG. 25 is a flow chart of a method for initially storing data on a PDK in accordance with the present invention.

Generally, some types of profile information (e.g., a biometric profile) can only be acquired during a trusted initialization process that is administered by a trusted Notary. In one embodiment, other secure information such as medical conditions are also stored to the PDK 102 in the presence of a Notary. Alternatively, certain types of low-risk information can be added by the user without a Notary, such as, for example a change of address. In another embodiment, once an initial profile has been stored to the PDK 102, a user can add information to the PDK 102 using a Programmer without a Notary through self-authentication. For example, in one embodiment, a PDK 102 that has a stored biometric profile can be "unlocked" by providing a matching biometric input. Then, once unlocked, the user can add or remove additional profiles, insurance cards, personal information, etc. to the PDK 102 using a Programmer. For example, in one embodiment, a user that has unlocked his/her own PDK 102 can store additional biometric information (such as fingerprint information for other fingers) in his/her PDK 102. In another example, a user that cancels an insurance card, can unlock his/her PDK 102 to remove the insurance card information. In another embodiment, the user can make copies of the PDK 102 or move profiles from one PDK 102 to another once the PDK 102 is unlocked. FIG. 25 provides additional description of acquisition of an initialization process.

The profile history 322 includes a programmer ID field 324, a Notary ID 326, and a site ID field 328. The profile history 322 relates to the specific hardware, Notary, and site used at the time the profile data was created and stored to the PDK. Typically each profile 320 stores its specific profile history 322 along with the profile data 330. The profile history 322 can be recalled for auditing purposes at a later time to ensure the credibility of the stored data. In one embodiment, transaction history can also be stored to the PDK memory 310. Here, the PDK 102 stores information associated with any transactions made with the PDK 102 such as the healthcare provider, reason for office visit and insurance used, etc.

The PDK 102 also includes a programmer I/O 340 that provides an interface to a trusted Programmer (not shown). The Programmer comprises trusted hardware that is used to program the memory 310 of the PDK 102. An example embodiment of a Programmer is described in U.S. patent application Ser. No. 11/744,832 to John Giobbi, et al., entitled "Personal Digital Key Initialization and Registration For Secure Transaction" and filed on May 5, 2007, the entire contents of which are incorporated herein by reference. The programmer I/O 340 can be, for example, a USB interface, serial interface, parallel interface, or any other direct or wireless link for transferring information between the PDK 102 and the Programmer. When coupled to the Programmer, the programmer I/O 340 receives initialization data, registration data or other information to be stored in the memory 310.

In one embodiment, the programmer I/O 340 is attached to an asset (e.g., equipment) in order to monitor the asset and trigger alerts. For example, in one embodiment, the programmer I/O may be connected to the equipment and monitor the calibration of the equipment and/or its usage. In one such embodiment, one or more of the tracking server 210 and the alert server 250 utilize that information to generate an alert when the equipment is out of calibration and schedule maintenance on the equipment at a time when the equipment is seldom used and/or an alternative piece of equipment is normally available. For another example, in one embodiment, the programmer I/O 340 may be connected to a piece of equipment, detect a low battery and generate an alert. In one embodiment, if the battery is low, the programmer I/O 340 may send an output to the equipment to turn on an LED or make a sound, for example, to make the equipment easier to identify in a crowded supply closet especially if the closet contains similar equipment. As described below, in some embodiments, such an output is sent responsive to the satisfaction of one or more alert criteria and/or the selection of the PDK 102 or the item (i.e., user or asset) associated with the PDK 102 using a software interface on a computing device 120.

In some embodiments, the PDK 102 includes (not shown) or is communicatively connected (e.g. via the programmer I/O 340) to an input device such as a button. In one such embodiment, use of the input device signals the system 100 to display information related to that item. For example, assume a PDK 102 associated with includes a button, in one embodiment, when that button is pressed information regarding the equipment including its usage and/or calibration information is sent for display on the equipment itself and/or a computing device 120.

The control logic 350 coordinates between functions of the PDK 102. In one embodiment, the control logic 350 facilitates the flow of information between the programmer I/O 340, transceiver 360 and memory 310. The control logic 350 can further process data received from the memories 310, programmer I/O 340 and transceiver 360. Note that the control logic 350 is merely a grouping of control functions in a central architecture, and in other embodiments, the control functions can be distributed between the different modules of the PDK 102. The operation of the control logic will be understood to those skilled in the art based on the description below corresponding to FIGS. 8-11D.

Optionally, the PDK 102 can also include a built in biometric reader 370 to acquire a biometric input from the user. The biometric reader 370 is configured to obtain a representation of physical or behavioral characteristics derived from the individual. The biometric input can be used to unlock the PDK 102 for profile updates, or for various types of authentication. For example, in one embodiment, a biometric input is received by the PDK 102 and compared to stored biometric information. Then, if the user is authenticated, the PDK 102 can indicate to the Reader 108 that the user is authenticated and transmit additional information (e.g., a credit card number) needed to complete a transaction.

Optionally, the PDK 102 can also include a temp sensor 375 to acquire temperature readings, which may be used in tracking and reporting an asset's temperature or generating a temperature alert as described further below. The temp sensor 375 can be communicatively coupled to the PDK 102 or integrated into the PDK as illustrated depending upon the embodiment. In another embodiment, the temp sensor 375 is separate from the PDK and communicatively coupled to the PDK through the PDK's I/O port or is communicatively coupled to a Reader 108.

The transceiver 360 is a wireless transmitter and receiver for wirelessly communicating with a Reader 108 or other wireless device. The transceiver 360 sends and receives data as modulated electromagnetic signals. Moreover, the data can be encrypted by the transceiver 360 and transmitted over a secure link. Further, the transceiver 360 can actively send connection requests, or can passively detect connection requests from another wireless source. In one embodiment, the transceiver 360 is used in place of a separate programmer I/O 340 and is used to wirelessly communicate with the Programmer for programming. In one embodiment, the transceiver 360 is adapted to communicate over a range of up to around 5 meters.

Figure 4:
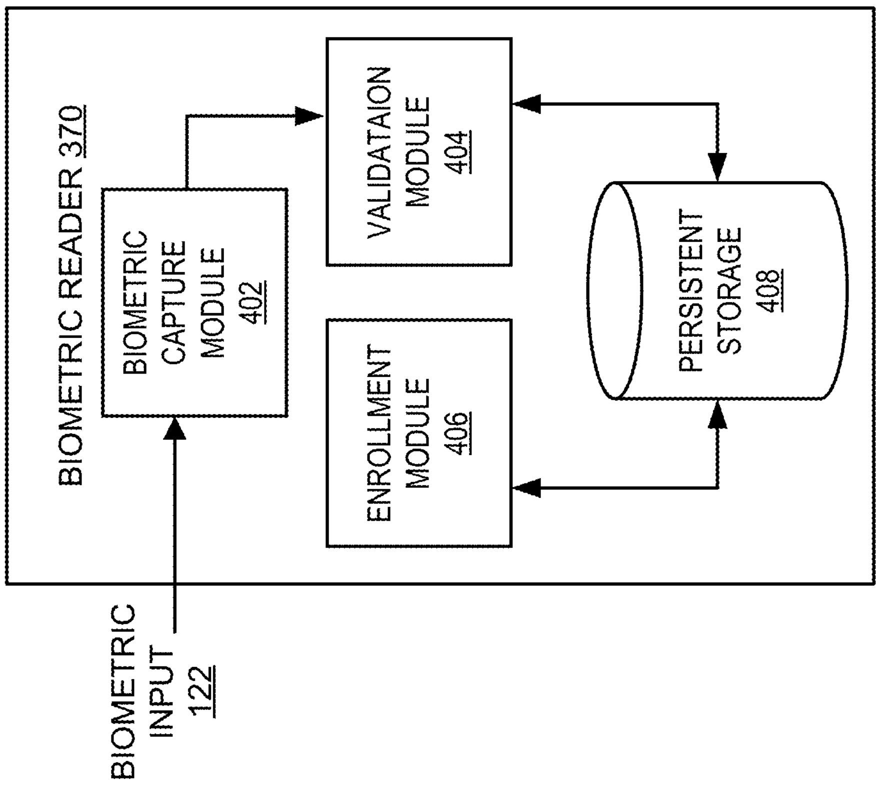
FIG. 4 is a block diagram illustrating one embodiment of a biometric reader of a PDK in accordance with the present invention.

FIG. 4 is a block diagram illustrating one embodiment of a biometric reader 370 of a PDK 102. The biometric reader 370 includes a biometric capture module 402, a validation module 404, an enrollment module 406 and persistent storage 408. In one embodiment, the enrollment module 406 registers a user with a PDK 102 by persistently storing biometric data associated with the user. Further, enrollment module 406 registers PDK 102 with a trusted authority by providing the code (e.g., device ID or PDK ID 312) to the trusted authority. Or conversely, the trusted authority can provide the code to PDK 102 to be stored therein.

The biometric capture module 402 comprises a scan pad to capture scan data from a user's fingerprint (e.g., a digital or analog representation of the fingerprint). Other embodiments of the biometric capture module 402 includes retinal scanners, iris scanners, facial scanner, palm scanners, DNA/RNA analyzers, signature analyzers, cameras, microphones, and voice analyzers to capture other identifying biometric data. Using the biometric data, validation module 404 determines whether the user's fingerprint, or other biometric data, matches the stored biometric data from enrollment. Conventional techniques for comparing fingerprints can be used. For example, the unique pattern of ridges and valleys of the fingerprints can be compared. A statistical model can be used to determine comparison results. Validation module 404 can send comparison results to control logic 350 of the PDK 102.

In other embodiments, validation module 404 can be configured to capture biometric data for other human characteristics. For example, a digital image of a retina, iris, and/or handwriting sample can be captured. In another example, a microphone can capture a voice sample.

Persistent storage 408 persistently stores biometric data from one or more users which can be provided according to specific implementations. In one embodiment, at least some of persistent storage 408 is a memory element that can be written to once but cannot subsequently be altered. Persistent storage 408 can include, for example, a ROM element, a flash memory element, or any other type of non-volatile storage element. Persistent storage 508 is itself, and stores data in, a tamper-proof format to prevent any changes to the stored data. Tamper-proofing increases reliability of authentication because it does not allow any changes to biometric data (i.e., allows reads of stored data, but not writes to store new data or modify existing data). Furthermore, data can be stored in an encrypted form.

In one embodiment, persistent storage 408 also stores the code that is provided by the PDK 102 responsive to successful verification of the user. Further, in some embodiments persistent storage 408 stores other data utilized during the operation of PDK 102. For example, persistent storage 408 can store encryption/decryption keys utilized to establish secure communications links.

An example embodiment of PDK 102 including a biometric reader is described in U.S. patent application Ser. No. 11/314,199 to John Giobbi, et al., entitled "Biometric Personal Data Key (PDK) Authentication", the entire contents of which are incorporated herein by reference.

Figure 5:
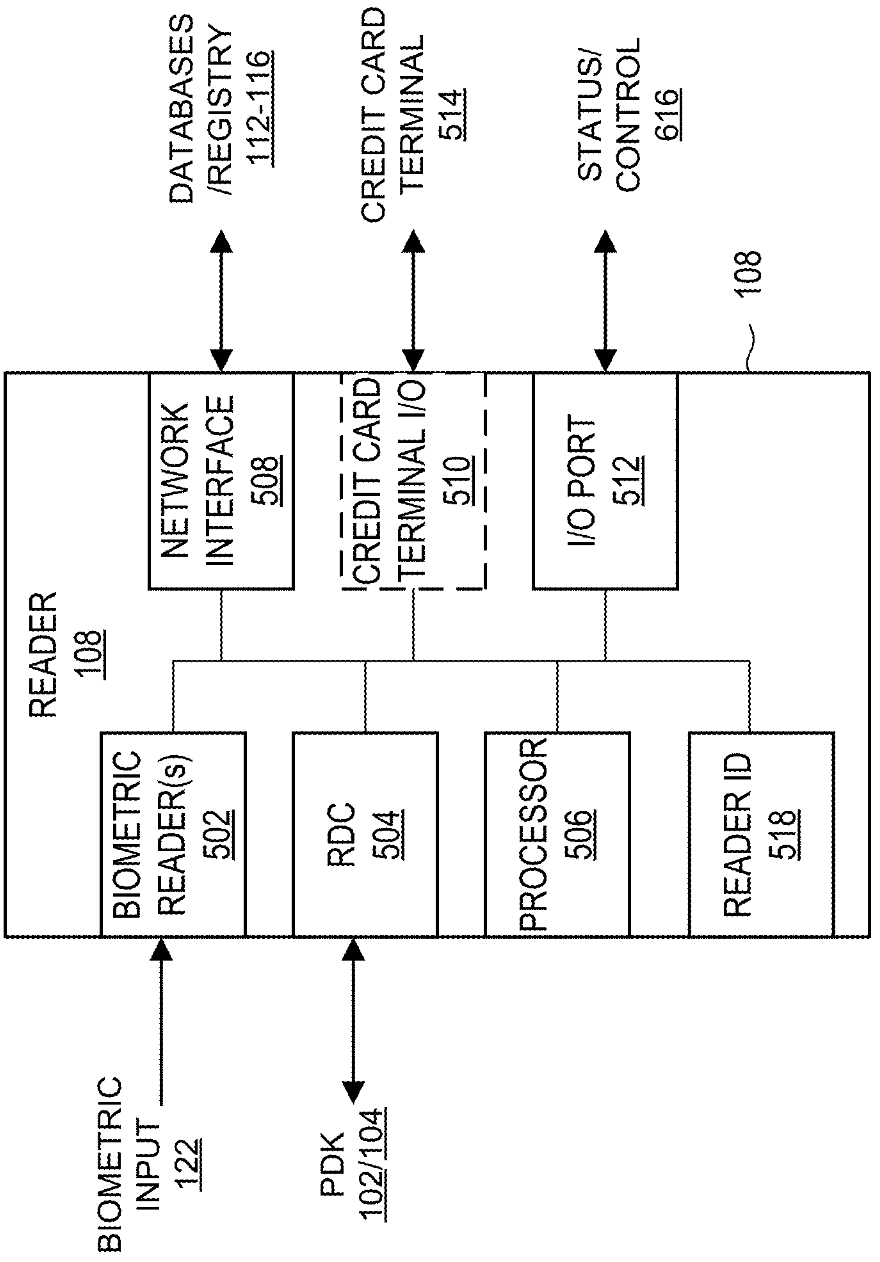
FIG. 5 is a block diagram illustrating one embodiment of a reader in accordance with the present invention.

Turning now to FIG. 5, an example embodiment of a Reader 108 is illustrated. The embodiment includes one or more biometric readers 502, a receiver-decoder circuit (RDC) 504, a processor 506, a network interface 508, an I/O port 612, optionally a credit card terminal I/O 510 and a reader ID 518. In alternative embodiments, different or additional modules can be included in the Reader 108.

The RDC 504 provides the wireless interface to the PDK 102. Generally, the RDC 504 wirelessly receives data from the PDKs 102 in an encrypted format and decodes the encrypted data for processing by the processor 506. An example embodiment of an RDC is described in U.S. patent application Ser. No. 11/292,330 entitled "Personal Digital Key And Receiver/Decoder Circuit System And Method", the entire contents of which are incorporated herein by reference. Encrypting data transmitted between the PDK 102 and Reader 108 minimizes the possibility of eavesdropping or other fraudulent activity. In one embodiment, the RDC 504 is also configured to transmit and receive certain types of information in an unencrypted or public format.

The biometric reader 502 receives and processes the biometric input 122 from an individual and is configured to obtain a representation of physical or behavioral characteristics derived from the individual. In one embodiment, the biometric reader 602 is a fingerprint scanner. Here, the biometric reader 502 includes an image capture device adapted to capture the unique pattern of ridges and valleys in a fingerprint also known as minutiae. Other embodiments of biometric readers 502 include retinal scanners, iris scanners, facial scanner, palm scanners, DNA/RNA analyzers, signature analyzers, cameras, microphones, and voice analyzers. Furthermore, the Reader 108 can include multiple biometric readers 502 of different types. In one embodiment, the biometric reader 502 automatically computes mathematical representations or hashes of the scanned data that can be compared to the mathematically processed biometric profile information stored in the PDK 102.

The processor 506 can be any general-purpose processor for implementing a number of processing tasks. Generally, the processor 506 processes data received by the Reader 108 or data to be transmitted by the Reader 108. For example, a biometric input 122 received by the biometric reader 502 can be processed and compared to the biometric profile 320 received from the PDK 102 in order to determine if a transaction should be authorized. In different embodiments, processing tasks can be performed within each individual module or can be distributed between local processors and a central processor. The processor 506 further includes a working memory for use in various processes.

The network interface 508 is a wired or wireless communication link between the Reader 108 and one or more external databases such as, for example, a validation database 112, the Central Registry 114 or a private registry 116*a*, 116*b*. For example, in one type of authentication, information is received from the PDK 102 at the RDC 504, processed by the processor 506, and transmitted to an external database 112-116 through the network interface 508. The network interface 508 can also receive data sent through the network 110 for local processing by the Reader 108. In one embodiment, the network interface 508 provides a connection to a remote system administrator to configure the Reader 108 according to various control settings.

The I/O port 512 provides a general input and output interface to the Reader 108. The I/O port 512 may be coupled to any variety of input devices to receive inputs such as a numerical or alphabetic input from a keypad, control settings, menu selections, confirmations, and so on. Outputs can include, for example, status LEDs, an LCD, or other display that provides instructions, menus or control options to a user.

The credit card terminal I/O 510 optionally provides an interface to an existing credit card terminal 514. In embodiments including the credit card terminal I/O 510, the Reader 108 supplements existing hardware and acts in conjunction with a conventional credit card terminal 514. In an alternative embodiment, the functions of an external credit card terminal 514 are instead built into the Reader 108. Here, a Reader 108 can completely replace an existing credit card terminal 514.

In one embodiment, a Reader 108 is adapted to detect and prevent fraudulent use of PDKs that are lost, stolen, revoked, expired or otherwise invalid. For example, the Reader 108 can download lists of invalid PDKs IDs 312 from a remote database and block these PDKs 102 from use with the Reader 108. Furthermore, in one embodiment, the Reader 108 can update the blocked list and/or send updates to remote registries 114,116*a*, 116*b* or remote Readers 108 upon detecting a fraudulently used PDK 102. For example, if a biometric input 122 is received by the Reader 108 that does not match the biometric profile received from the PDK 102, the Reader 108 can obtain the PDK ID 312 and add it to a list of blocked PDK IDs 312. In another embodiment, upon detecting fraudulent use, the Reader 108 can send a signal to the PDK 102 that instructs the PDK 102 to deactivate itself. The deactivation period can be, for example, a fixed period of time, or until the rightful owner requests re-activation of the PDK 102. In yet another embodiment, the Reader 108 can send a signal instructing the fraudulently obtained PDK 102 to send alarm signals indicating that the PDK 102 is a stolen device. Here, a stolen PDK 102 can be tracked, located and recovered by monitoring the alarm signals. In one embodiment, the Reader 108 stores biometric or other identifying information from an individual that attempts to fraudulently use a PDK 102 so that the individual's identity can be determined.

The reader ID 518 is memory that stores the reader's unique identification number. The memory can be a read-only memory, a once-programmable memory, a read/write memory or any combination of memory types including physical access secured and tamper-proof memories. The reader ID 518 plays an integral role in the process for tracking equipment, supplies and individuals as will be explained in more detail below.

Generally, the Reader 108 is configured to implement at least one type of authentication prior to enabling a transaction. In many cases, multiple layers of authentication are used. A first layer of authentication, referred to herein as "device authentication," begins any time a PDK 102 moves within range of a Reader 108. In device authentication, the Reader 108 and the PDK 102 each ensure that the other is valid based on the device characteristics, independent of any profiles stored in the PDK 102. In some configurations, when fast and simple authentication is desirable, only device authentication is required to initiate the transaction. For example, a Reader 108 may be configured to use only device authentication for office visit check-ins. The configuration is also useful in other types of low risk transactions where speed is preferred over additional layers of authentication.

Other configurations of the Reader 108 require one or more additional layers of authentication, referred to herein as "profile authentication" based on one or more profiles stored in the PDK 102. Profile authentication can include, for example, a biometric authentication, a PIN authentication, a photo authentication, a registry authentication, etc. or any combination of the above authentication types. Profile authentications are useful when a more exhaustive authentication process is desired, for example, for invasive patient treatments or drug administration. For example, profile authentication may be required for an invasive patient treatment such as a surgery in order to ensure that correct procedure is done on the correct patient and the correct body part. Beneficially minimizing the risk of removing the wrong person's leg, rebuilding the left knee when the right knee was supposed to be rebuilt, etc. For another example, profile authentication may be required prior to administering medication to ensure that the user is not given a medication the user is allergic to and/or that would be dangerous in combination with medications the user has already taken. Moreover, the profile authentication may be useful for a patient's administrative records such as but not limited to insurance information, information regarding the appointment of a medical power of attorney and whether the user has signed a do not resuscitate ("DNR").

Figure 6:
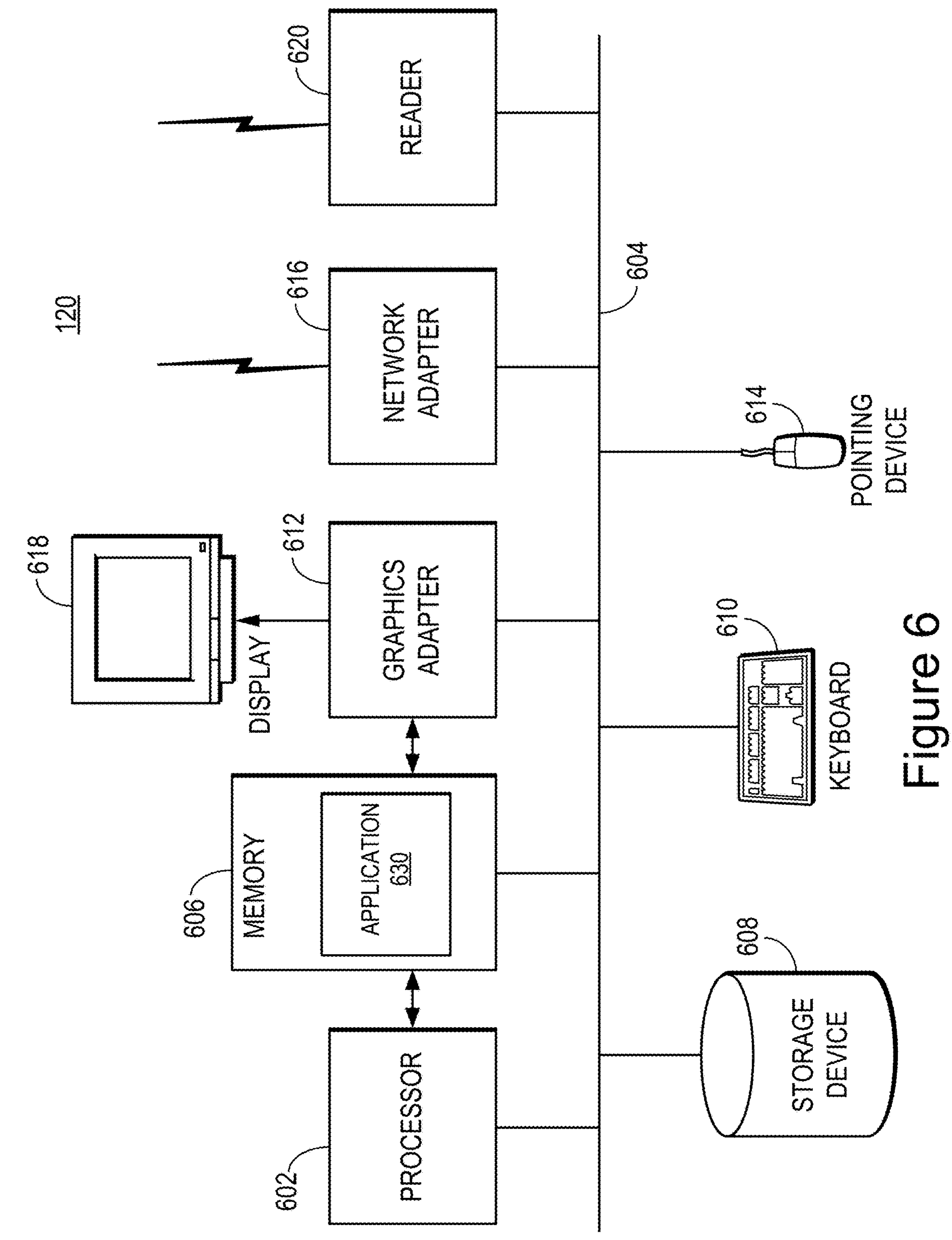
FIG. 6 is a block diagram illustrating one embodiment of a computing device in accordance with the present invention.

FIG. 6 is a high-level block diagram of one embodiment of a computing device 120. In one embodiment, the computing device 120 is a personal computer. In another embodiment, the computing device 120 is a smart phone or other mobile computing and communication device. Illustrated are at least one processor 602 coupled to a bus 604. Also coupled to the bus 604 are a memory 606, a storage device 608, a keyboard 610, a graphics adapter 612, a pointing device 614, a network adapter 616 and a reader 620. In one embodiment, the functionality of the bus 604 is provided by an interconnecting chipset. A display device 618 is coupled to the graphics adapter 612.

The memory 606 includes an application 630. In one embodiment, the application 630 enables the computing device 120 to communicate with the local services 124. In another embodiment, the application 630 processes information and data received from the readers 620 and various modules and servers of the local services 124 and third party link module 126.

The storage device 608 is any device capable of holding data, like a hard drive, compact disk read-only memory (CD-ROM), DVD, or a solid-state memory device. The memory 606 holds instructions and data used by the processor 602. The pointing device 614 may be a mouse, track ball, or other type of pointing device, and is used in combination with the keyboard 610 to input data into the computing device 120. The graphics adapter 612 displays images and other information on the display device 618. The network adapter 616 couples the computing device 120 to a local or wide area network.

As is known in the art, a computing device 120 can have different and/or other components than those shown in FIG. 6. In addition, the computing device 120 can lack certain illustrated components. In one embodiment, a computing device 120 lacks a keyboard 610, a pointing device 614, a graphics adapter 612, and/or a display device 618. Moreover, the storage device 608 can be local and/or remote from computing device 120 (such as embodied within a storage area network (SAN)). The reader 620 includes all or some of the components as the Reader 108 described above in conjunction with FIG. 5.

As is known in the art, the computing device 120 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 608, loaded into the memory 606, and executed by the processor 602.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Figure 7:
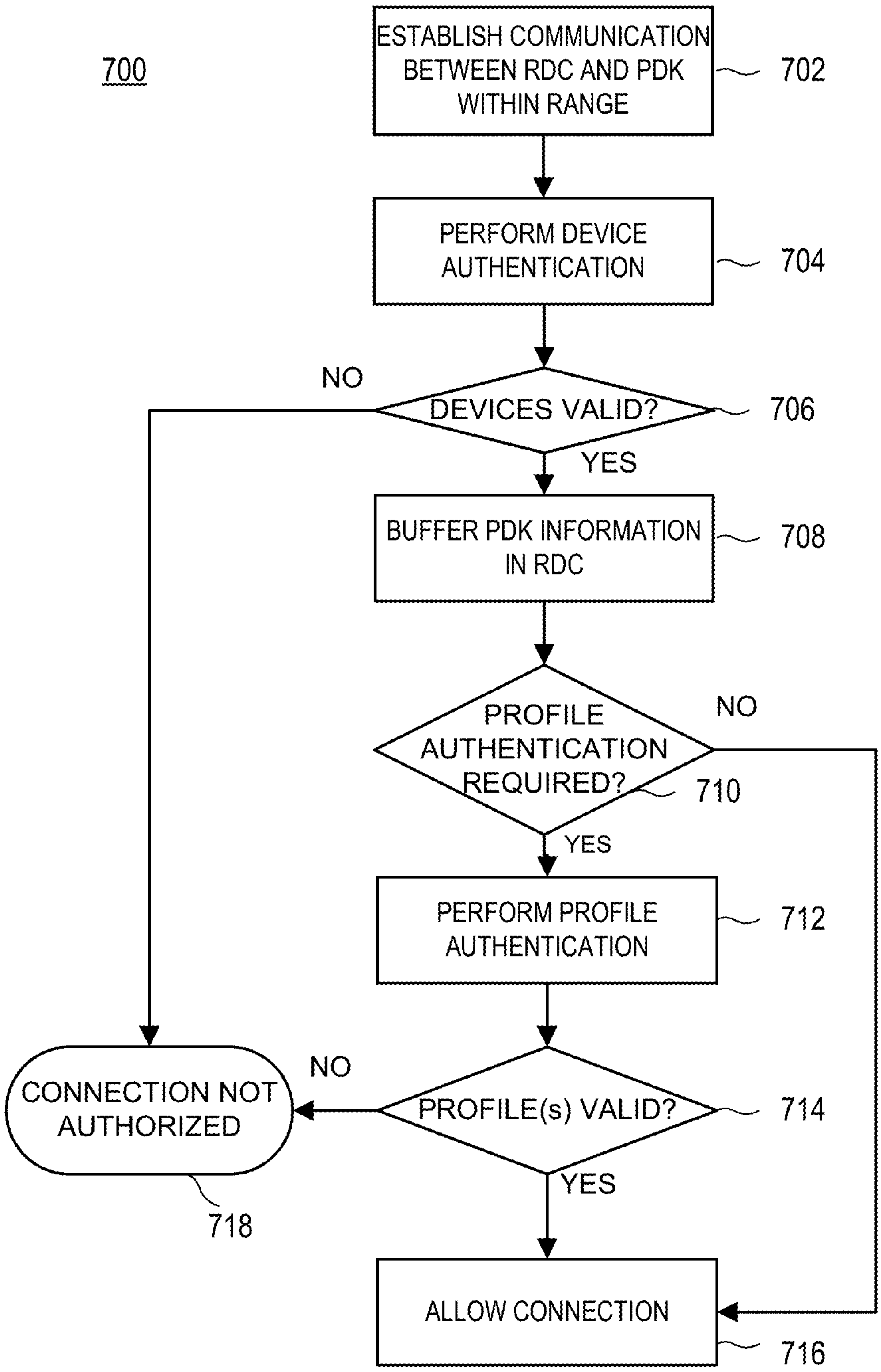
FIG. 7 is a flowchart of a method for authorizing a communication connection using secure authentication in accordance with the present invention.

FIG. 7 is a flowchart illustrating one embodiment of a process for authorizing a communication connection using secure authentication. When a PDK 102 comes within range of a Reader 108, communication is automatically established 702 between the RDC 504 of the Reader 108 and the PDK 102. It should be noted that the processes described herein with regards to Reader 108 may be also performed with reader 620 of the computing device 120.

In one embodiment, the RDC 504 continually transmits beacons that are detected by the PDK 102 when it enters a proximity zone of the Reader 108. In an alternative embodiment, the communication is instead initiated by the PDK 102 and acknowledged by the Reader 108. The initial communication between the Reader 108 and the PDK 102 may or may not be encrypted to provide increased security of communication between the Reader and the PDK 102.

In step 704, a device authentication is performed. Here, the Reader 108 establishes if the PDK 102 is a valid device and PDK 102 establishes if the Reader 108 is valid. Furthermore, device authentication determines if the PDK 102 is capable of providing the type of authentication required by the Reader 108.

Figure 8:
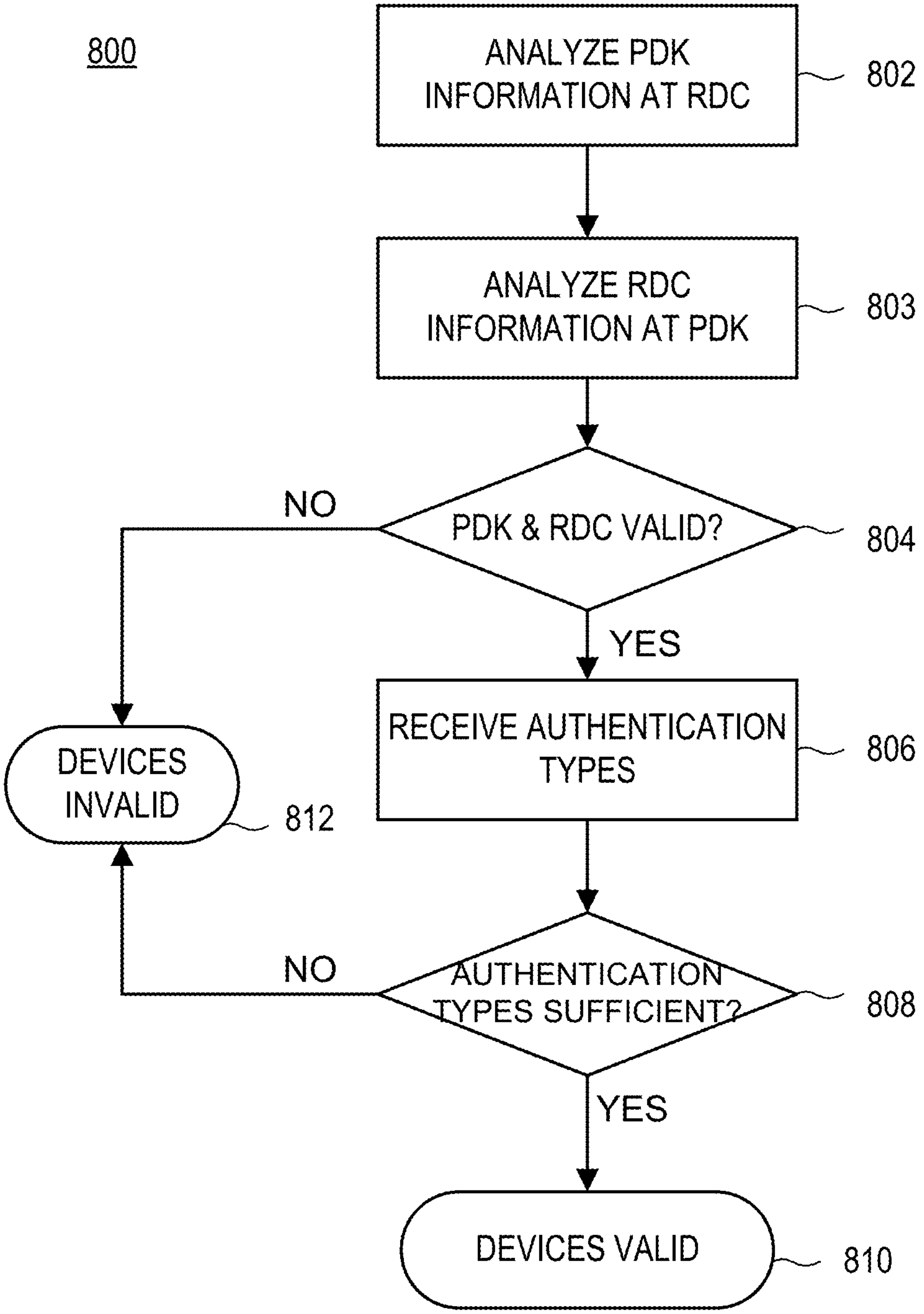
FIG. 8 is a flowchart of a method for device authentication by a reader in accordance with the present invention.

An example embodiment of a method 800 for performing 704 device authentication is illustrated in FIG. 8. The RDC 504 receives and analyzes 802 information from the PDK 102 and the PDK 102 receives and analyzes 802 information received from the RDC 504. Generally, this initial information is transmitted over a public communication channel in an unencrypted format. Based on the received information, each device 102, 504 determines 804 if the other is valid. As will be apparent to one of ordinary skill in the art, a number of different protocols can be used for this type of authentication such as, for example, a challenge-response authentication or a challenge handshake authentication protocol (CHAP). If either of the devices 102, 504 is invalid 812, the process ends. If both the PDK 102 and the RDC 604 are determined by the other to be valid, the Reader 108 requests and receives 806 authentication type information from the PDK 102 indicating the different types of authentication the PDK 102 is capable of satisfying based on the types of profiles stored by the PDK 102.

The available profile types in the PDK 102 are compared against the authentication types that can be used by the Reader 108. For example, a particular Reader 108 may be configured to perform only a fingerprint authentication and therefore any PDK without a fingerprint biometric profile cannot be used with the Reader 108. In one embodiment, the Reader 108 can allow more than one type of profile to be used. In another embodiment, the Reader 108 requires more than one type of profile for authentication, while in yet further embodiments no profile authentications are required. Next, the method determines 808 whether the PDK 102 has one or more profiles sufficient for authentication. If the PDK 102 does not have one or more profiles sufficient for authentication with the Reader 108, the devices 102, 504 are determined to be invalid 812 because they cannot be used with each other. If the PDK 102 does have one or more sufficient types of profiles, the devices are valid 810.

Turning back to FIG. 7, if either the PDK 102 or RDC 504 is not found valid (706—No) during device authentication 704, the connection is not authorized 718 and the process ends. If the devices are valid (706—Yes), the RDC 504 temporarily buffers 708 the received PDK information. It is noted that in one embodiment, steps 702-708 are automatically initiated each time a PDK 102 enters the proximity zone of the Reader 108. Thus, if multiple PDKs 102 enter the proximity zone, the Reader 108 automatically determines which PDKs 102 are valid and buffers the received information from each valid PDK 102.

The method next determines 710 whether profile authentication is required based on the configuration of the Reader 108, the type of transaction desired or by request of a merchant or other administrator. If the Reader 108 configuration does not require a profile authentication in addition to the PDK authentication, then the Reader 108 proceeds to complete the transaction for the PDK 102. If the Reader 108 does require profile authentication, the profile authentication is performed 712 as will be described below with references to FIGS. 9-10D. If a required profile is determined 714 to be valid, the Reader 108 allows 716 the connection. Otherwise, the Reader 108 indicates that the connection is not authorized 718. In one embodiment, allowing 716 the connection includes enabling access to secure patient records. In another embodiment, allowing 716 the connection includes enabling the automatic logging in and out of software and system applications. Patient or provider name or medical record number (typically stored in a profile memory field 332) can be transmitted by the PDK 102 for identification purposes. In one embodiment, the PDK 102 is configured with multiple purchasing means and a default is configured for different types of transactions. In another embodiment, each insurance card or medical billing information is displayed to the customer by the Reader 108 and the customer is allowed to select which to apply to the office visit.

Figure 9:
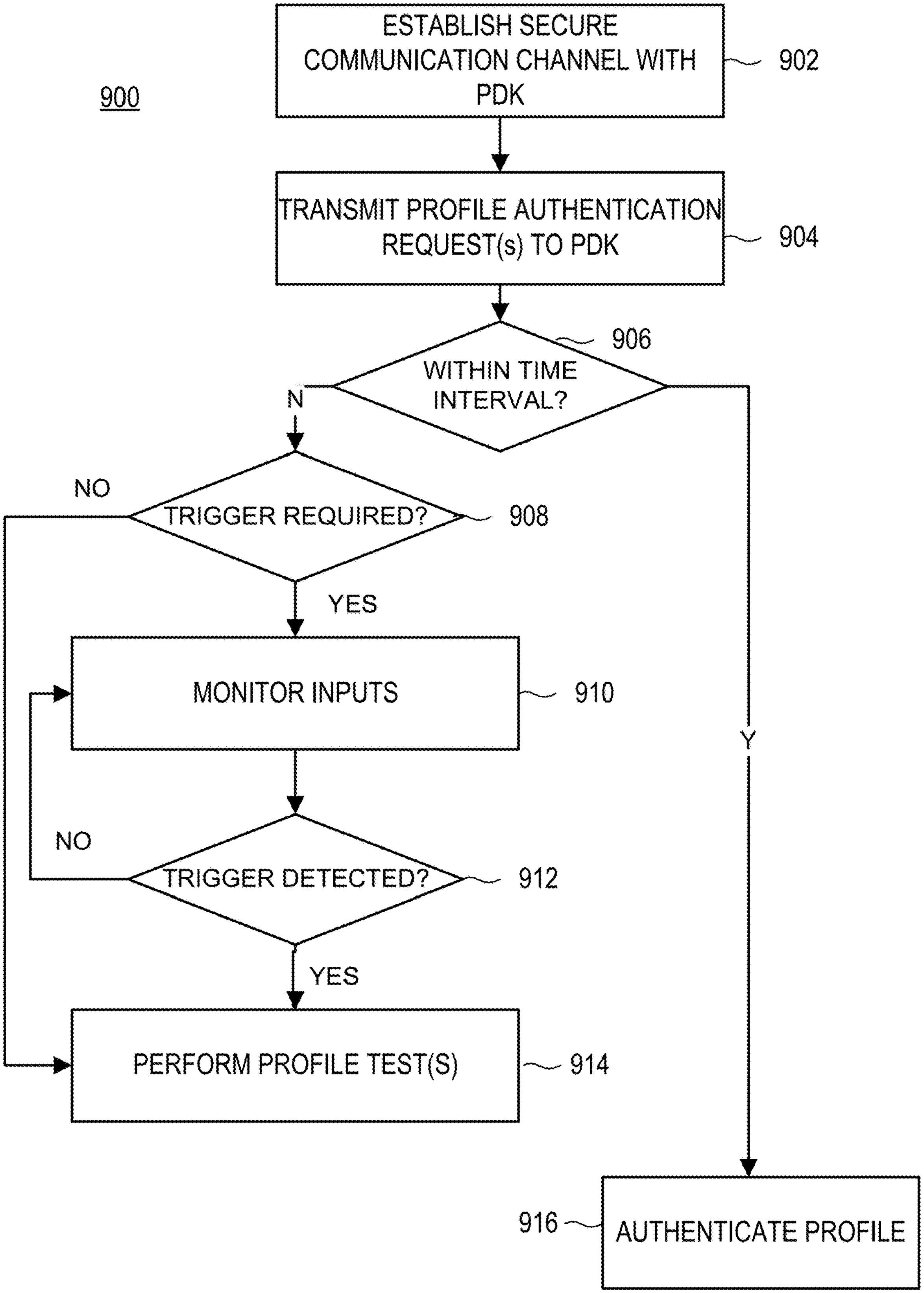
FIG. 9 is a flowchart of a method for profile authentication by a reader in accordance with the present invention.

Turning now to FIG. 9, an embodiment of a method 900 for profile authentication is illustrated. In step 902, a secure communication channel is established between the RDC 504 and the PDK 102. Information sent and received over the secure channel is in an encrypted format that cannot be practically decoded, retransmitted, reused, or replayed to achieve valid responses by an eavesdropping device. The Reader 108 transmits 904 profile authentication requests to the PDK 102 requesting transmission of one or more stored profiles over the secure channel.

In one embodiment, a trigger is required certain times, but not required within specified time intervals. This allows a trigger to initially be required to authenticate a profile, but not required after initial authentication of the profile. For example, a trigger may be required to authenticate a profile the first time the Reader 108 transmits 904 a profile authentication request to the PDK 102, prompting a biometric authentication, or other type of authentication, as further described below. If the profile is authenticated, the next time the Reader 108 transmits 904 a profile authentication request to the PDK 102 during a specified time interval, no trigger is required and the Reader 108 relies on the previous authentication to authenticate the profile. Thus, the time interval simplifies access to a computing device 120 associated with the Reader 108 by identifying a length of time during which the profile is considered to be authenticated without being tested or without requiring detection of a trigger, as described below.

For example, the first time a healthcare provider accesses a computing device 120, the healthcare provider is required to provide a biometric input, as further described below, to verify the identity of the healthcare provider. To simplify subsequent access to the computing device 120, a time interval of four hours is associated with the healthcare provider's profile, so that the healthcare provider's profile remains authenticated by the Reader 108 for four hours after initial authentication. This allows the healthcare provider to subsequently access the computing device 120 without again providing biometric input. However, after four hours have elapsed, when the healthcare provider again accesses the Reader 108, the Reader 108 again requires the healthcare provider to provide a biometric input to verify the healthcare provider's profile.

Accordingly, after the Reader 108 transmits 904 profile authentication requests to the PDK 102 requesting transmission of one or more stored profiles over the secure channel and received a stored profile for authentication, the Reader 108 determines 906 whether a requested profile is within an associated time interval. In one embodiment, the time interval data is transmitted by the PDK 102 along with the profile. Alternatively, the Reader 108 includes data describing time interval data associated with different profiles and uses the included data to determine 906 whether the profile is within its associated time interval. For example, the time interval data includes a profile ID, the time interval and the time when the profile was last authenticated. The Reader 108 determines whether the time when the profile is received responsive to an authentication request is within the duration specified by the time interval of the time when the profile was last authenticated.

If the profile is not within its associated time interval (906-No), the process determines 908 whether a "trigger" is required for authentication. The requirement for a trigger depends on the configuration of the Reader 108, the specific type of transaction to be executed and the type of authentication requested. For example, if it has been longer than the time interval from the time when the profile was previously authenticated to the time when the profile is received responsive to the authentication request, the process determines 908 whether a trigger is needed to authenticate the profile.

In a first configuration, a trigger is required to continue the process because of the type of authentication being used. For example, in biometric authentication, the authentication process cannot continue until the Reader 108 detects a biometric contact and receives biometric information. It is noted that biometric contact is not limited to physical contact and can be, for example, the touch of a finger to a fingerprint scanner, the positioning of a face in front of a facial or retinal scanner, the receipt of a signature, the detection of a voice, the receipt of a DNA sample, RNA sample, or derivatives or any other action that permits the Reader 108 to begin acquiring the biometric input 122. By supplying the biometric contact, the user indicates that the authentication and transaction process should proceed. For example, a PDK holder that wants log in to the healthcare software application system via the computing device 120 initiates the login process by touching a finger to the reader 720 of the computing device 120. The computing device 120 then displays confirmation of the user's login.

In a second configuration, some other user action is required as a trigger to proceed with the transaction even if the authentication process itself does not necessarily require any input. This can be used for many purchasing transactions to ensure that the purchase is not executed until intent to purchase is clear. For example, a Reader 108 at a gas station can be configured to trigger the transaction when a customer begins dispensing gas. At a supermarket, a Reader 108 can be configured to trigger the transaction when items are scanned at a checkout counter. Similarly, a user may login to a healthcare software application system via the computing device 120 by simply being in the proximity zone of the reader 620 of a computing device 120 and beginning to use the keyboard 610 or pointing device 614 of the computing device 120.

In a third configuration, no trigger is used and the Reader 108 automatically completes the remaining authentication/transaction with no explicit action by the user. This configuration is appropriate in situations where the mere presence of a PDK 102 within range of the Reader 108 is by itself a clear indication of the person associated with the PDK 102 desires to complete a transaction. For example, a Reader 108 can be positioned inside the entrance to a doctor's office or clinic. When a patient having an associated PDK 102 walks through the entrance, the Reader 108 detects the PDK 102 within range, authenticates the user, and notifies the receptionist that the patient has arrived for his or her appointment. Thus, if no trigger is required, the process next performs 914 the requested profile authentication tests.

If a trigger is required, the Reader 108 monitors 910 its inputs (e.g., a biometric reader, key pad, etc.) and checks for the detection 912 of a trigger. If the required trigger is detected, the process continues to perform 914 one or more profile authentication test. FIGS. 10A-10D illustrate various embodiments of profile authentication tests. According to different configurations of the Reader 108, one or more of the illustrated authentication processes may be used. Further, in some embodiments, one or more of the processes may be repeated (e.g., for different types of biometric inputs).

However, if the Reader 108 determines 906 that the requested profile is received within an associated time interval, the Reader authenticates 916 the profile. This beneficially simplifies access to a computing device 120 coupled to the Reader 108 by allowing an individual to bypass profile authentication when the Reader 108 is accessed within a time interval of the initial profile authentication.

Figure 10B:
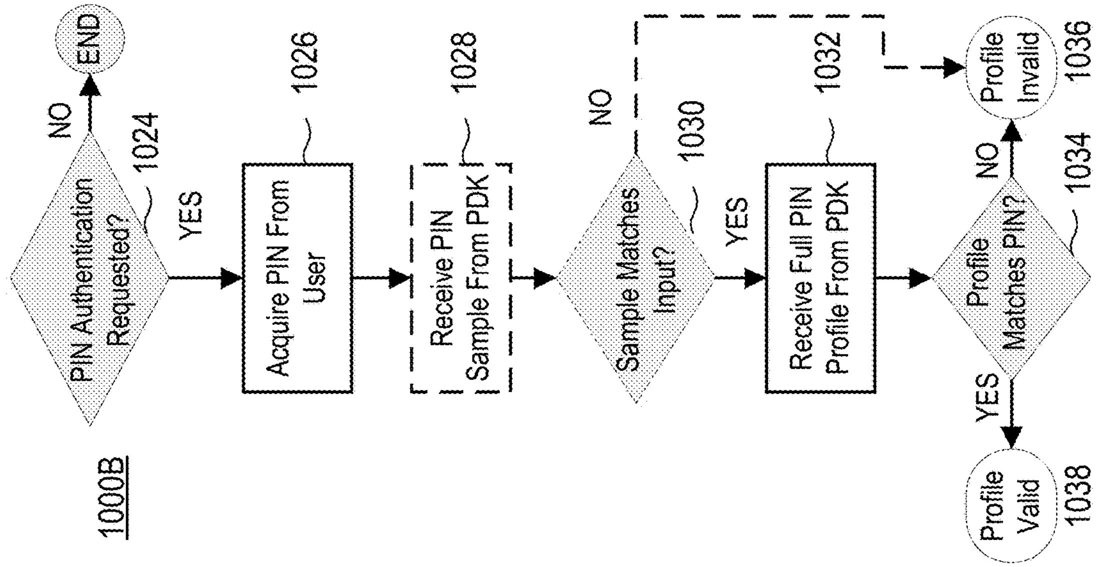
FIG. 10B is a flowchart of a method for profile testing using a personal identification number in accordance with the present invention.
Figure 10A:
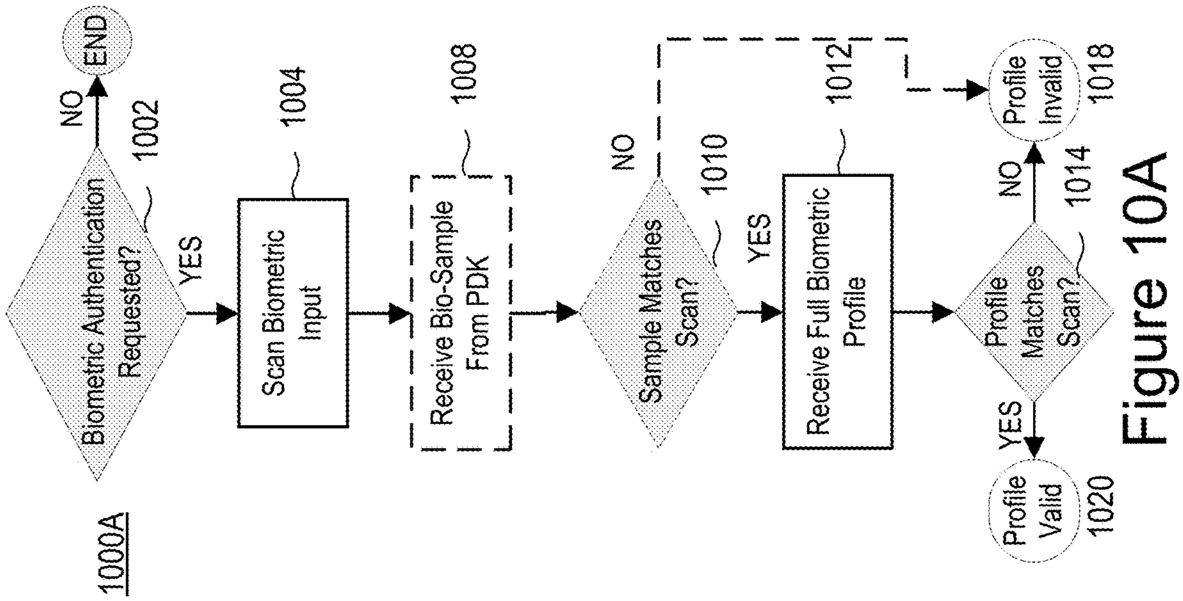
FIG. 10A is a flowchart of a method for biometric authentication in accordance with the present invention.

FIG. 10A illustrates a method 1000A for biometric authentication. In biometric authentication, a Reader 108 compares a biometric profile stored in the PDK 102 to the biometric input 122 acquired by the biometric reader 502. Advantageously, the biometric input 122 is not persistently stored by the Reader 108, reducing the risk of theft or fraudulent use. If the Reader 108 determine 1002 that biometric authentication is requested, the Reader 108 scans 1104 the biometric input 122 supplied by the user. In one embodiment, scanning 1004 includes computing a mathematical representation or hash of the biometric input 122 that can be directly compared to the biometric profile.

In one embodiment, scanning 1004 also includes obtaining a biometric input sample from the biometric input according to the same function used to compute the biometric profile sample stored in the PDK 102. Optionally, the Reader 108 receives 1008 a biometric profile sample from the PDK 102 and determines 1010 if the biometric profile sample matches the biometric input sample. If the biometric profile sample does not match the input sample computed from the scan, the profile is determined to be invalid 1018. If the biometric profile sample matches, the full biometric profile 1012 is received from the PDK 102 to determine 1014 if the full biometric profile 1012 matches the complete biometric input 122. If the profile 1012 matches the scan, the profile 1012 is determined to be valid 1120, otherwise the profile 1012 is invalid 1018. It is noted that in one embodiment, steps 1008 and 1010 are skipped and only a full comparison is performed. In one embodiment, the biometric profile and/or biometric profile sample is encoded and transmitted to the Reader 108 along with an encoding key and/or algorithm. Then, the Reader 108 uses the encoding key and/or algorithm to recover the biometric profile and/or biometric profile sample. In another alternative embodiment, only the encoding key and/or algorithm is transmitted by the PDK 102 and the biometric profile data is recovered from a remote database in an encoded form that can then be decoded using the key and/or algorithm.

It will be apparent to one of ordinary skill that in alternative embodiments, some of the steps in the biometric profile authentication process can be performed by the PDK 102 instead of the Reader 108 or by an external system coupled to the Reader 108. For example, in one embodiment, the biometric input 122 can be scanned 1004 using a biometric reader built into the PDK 102. Furthermore, in one embodiment, the steps of computing the mathematical representation or hash of the biometric input and/or the steps of comparing the biometric input to the biometric profile can be performed by the PDK 102, by the Reader 108, by an external system coupled to the Reader 108, or by any combination of the devices. In one embodiment, at least some of the information is transmitted back and forth between the PDK 102 and the Reader 108 throughout the authentication process. For example, the biometric input 122 can be acquired by the PDK 102, and transmitted to the Reader 108, altered by the Reader 108, and sent back to the PDK 102 for comparison. Other variations of information exchange and processing are possible without departing from the scope of the invention. The transfer of data between the PDK 102 and the Reader 108 and/or sharing of processing can provide can further contribute to ensuring the legitimacy of each device.

FIG. 10B illustrates a method 1000B for PIN authentication. If PIN authentication is requested 1024, a PIN is acquired 1026 from the user through a keypad, mouse, touch screen or other input mechanism. Optionally, the Reader 108 receives 1028 a PIN sample from the PDK 102 comprising a subset of data from the full PIN. For example, the PIN sample can comprise the first and last digits of the PIN. If the Reader 108 determines 1030 that the PIN sample does not match the input, the profile is immediately determined to be invalid 1036. If the PIN sample matches, the full PIN profile is received 1032 from the PDK 102 and compared to the input. If the Reader 108 determines 1034 that the profile matches the input, the profile is determined to be valid and is otherwise invalid 1036. It is noted that in one embodiment, steps 1028 and 1030 are skipped.

Figure 10D:
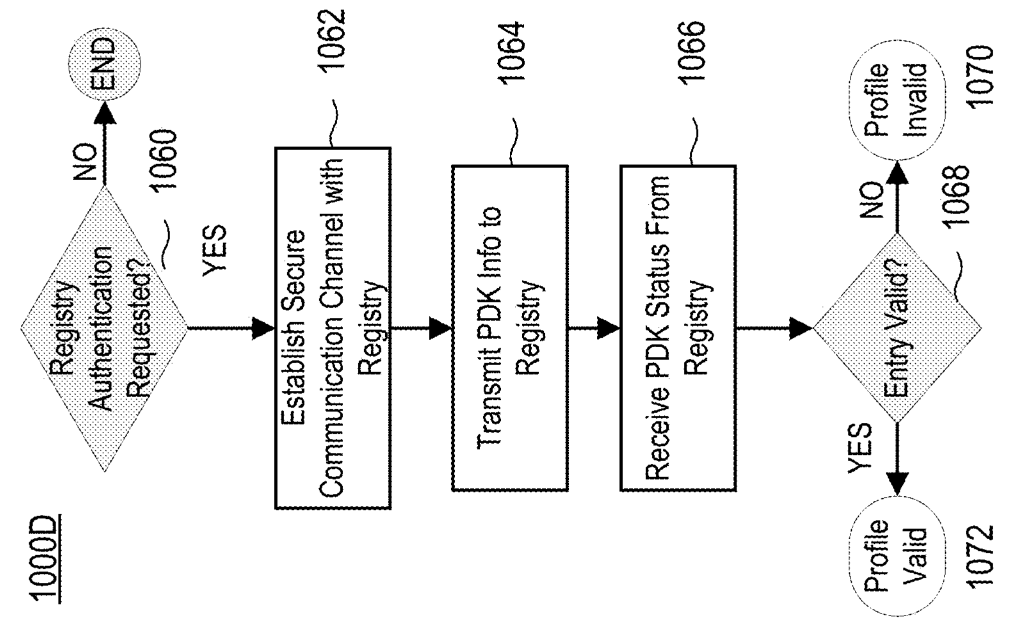
FIG. 10D is a flowchart of a method for profile testing using a private or central registry in accordance with the present invention.
Figure 10C:
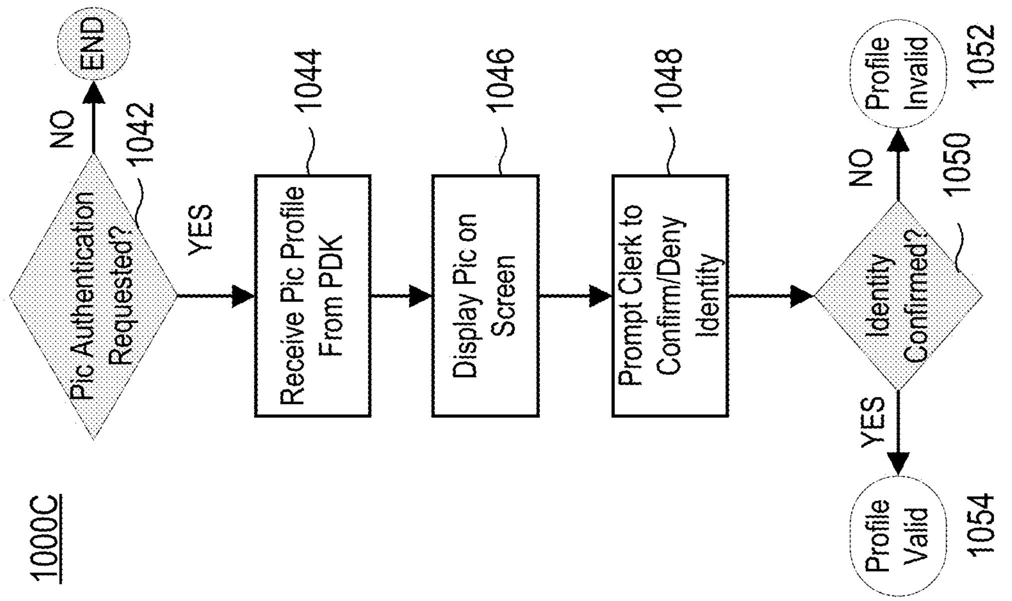
FIG. 10C is a flowchart of a method for profile testing using a picture profile in accordance with the present invention.

FIG. 10C illustrates a method 1000C for a picture authentication. If the Reader 108 determines 1042 that picture authentication is requested, a picture profile is received 1044 from the PDK 102 by the Reader 108 and displayed 1046 on a screen. An administrator (e.g., a clerk, security guard, etc.) is prompted 1048 to compare the displayed picture to the individual and confirms or denies if the identities match. If the administrator confirms that the identities match, the picture profile is determined to be valid 1054 and is otherwise invalid 1052. In an alternative embodiment, the process is automated and the administrator input is replaced with a process similar to that described above with reference to FIG. 10A. Here, an image of the user is captured and face recognition is performed by comparing picture profile information received from the PDK 102 to the captured image.

FIG. 10D illustrates a method 1000D for authentication with a private registry 116*a*, 116*b* or the Central Registry 114. If the Reader 108 determines that registry authentication is requested, a secure communication channel is established 1062 over the network 110 between the Reader 108 and one or more registries (e.g., the Central Registry 114, any private registry 116*a*, 116*b*, or other validation database 112). If any additional information is needed to process the registry authentication (e.g., an insurance policy number), the Reader 108 requests and receives the additional information from the PDK 102. Identification information is transmitted 1064 from the Reader 108 to the registry 114, 116*a*, 116*b* through the network interface 608. The PDK status is received 1066 from the registry to determine 1068 if the status is valid 1072 or invalid 1070. In one embodiment, the information is processed remotely at the registry 114, 116*a*, 116*b* and the registry 114, 116*a*, 116*b* returns a validation decision to the Reader 108. In another embodiment, the Reader 108 queries the private 116*a*, 116*b* or Central registry 114 for information that is returned to the Reader 108. The information is then analyzed by the Reader 108 and the authorization decision is made locally. In one embodiment, the process involves transmitting credit card (or other purchasing information) to a validation database 112 to authorize the purchase and receive the status of the card. Status information may include, for example, confirmation that the card is active and not reported lost or stolen and that sufficient funds are present to execute the purchase.

Figure 11A:
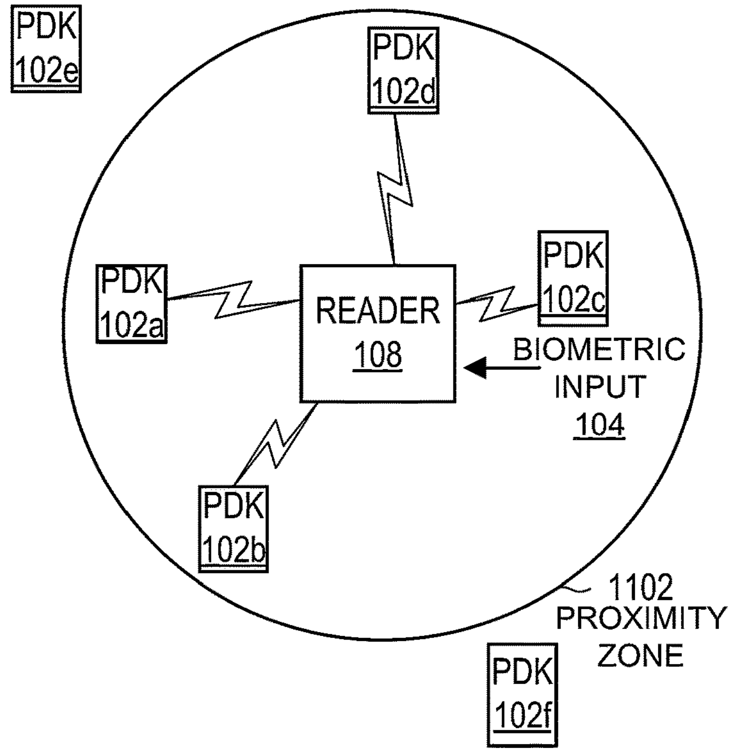
FIG. 11A illustrates an example scenario of a reader operating with multiple PDKs in its proximity zone in accordance with the present invention.
Figure 11B:
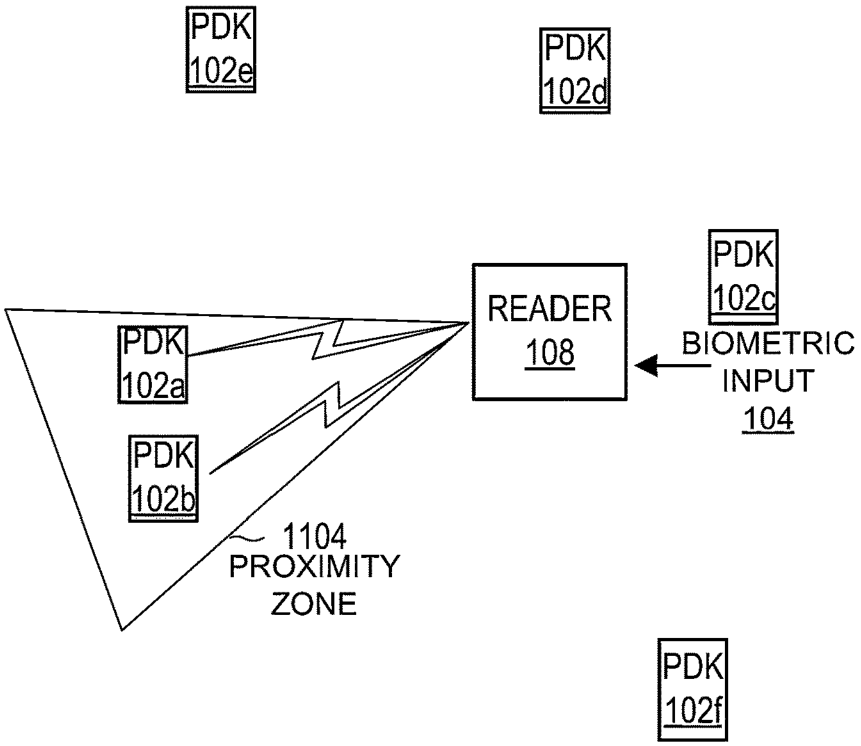
FIG. 11B illustrates an example scenario of operation of a reader with a directional proximity zone in an environment with multiple PDKs in accordance with the present invention.

FIGS. 11A and 11B illustrate scenarios where multiple PDKs 102*a-e* are present near a Reader 108. This scenario is common when a Reader 108 is located in a high occupancy area such as, for example, a hospital lobby or waiting area. In FIG. 11A, the Reader 108 communicates with PDKs 102*a-d* within the proximity zone 1102 and does not communicate with PDKs 102*e-f* outside the proximity zone 1102. In one embodiment, the Reader 108 receives the unique PDK ID from a PDK 102 when it enters the proximity zone 1102 and records its time of arrival. In one embodiment, the Reader 108 further initiates a device authentication of the PDK 102 after a predefined period of time (e.g., 5 seconds) that the PDK 102 is within the proximity zone 1102. For profile authentication, the Reader 108 automatically determines which PDK 102 should be associated with an authentication test and the transaction. For example, if the Reader 108 receives a biometric input 122 from an individual, the Reader 108 automatically determines which PDK 102*a-d* is associated with the individual supplying the biometric input 122. In another embodiment, a different trigger is detected (e.g., a PIN input) to initiate the differentiation decision. In yet another embodiment, the differentiation decision is initiated without any trigger. It is noted that in some embodiments, where no trigger is required (such as a registry authentication), no differentiation decision is made and authentications are instead performed for each PDK 102 within the proximity zone 1102.

In one embodiment, the proximity zone 1102 is scalable, allowing modification of the area in which the Reader 108 communicates with a PDK 102. For example, the proximity zone 1102 of a Reader 108 may be modified from 1 foot to 100 feet. In one embodiment, an administrator or other designated individual modifies the proximity zone 1102 of a Reader 108. This allows the sensitivity of a Reader 108 to be modified based on different operating environment. For example, in a healthcare provider setting, the proximity zone 1102 of a Reader 108 located in a doctor's office is smaller than the proximity zone 1102 of a Reader 108 located in an examination room to reduce the number of times that the Reader 108 in the doctor's office attempts to authenticate a PDK 102.

Additionally, while FIG. 11A shows a proximity zone 1102 that is symmetrical, in other implementations, the proximity zone is directional. FIG. 11B shows a directional proximity zone 1104 where the Reader 108 interacts with PDKs 102*a*, 102*b* in a specific location. Hence, in FIG. 11B the Reader 108 communicates with PDKs 102*a,b* within the directional proximity zone 1104 and does not communicate with PDKs 102*c-f* outside the directional proximity zone 1104. In one embodiment, a Reader 108 has an initial configuration of a proximity zone 1102 that extends 360 degrees around the Reader; however, the Reader 108 may be modified from the initial configuration to focus the proximity zone into a directional proximity zone 1104. For example, a directional antenna may be coupled to the Reader 108 to generate a directional proximity zone 1104.

Figure 12:
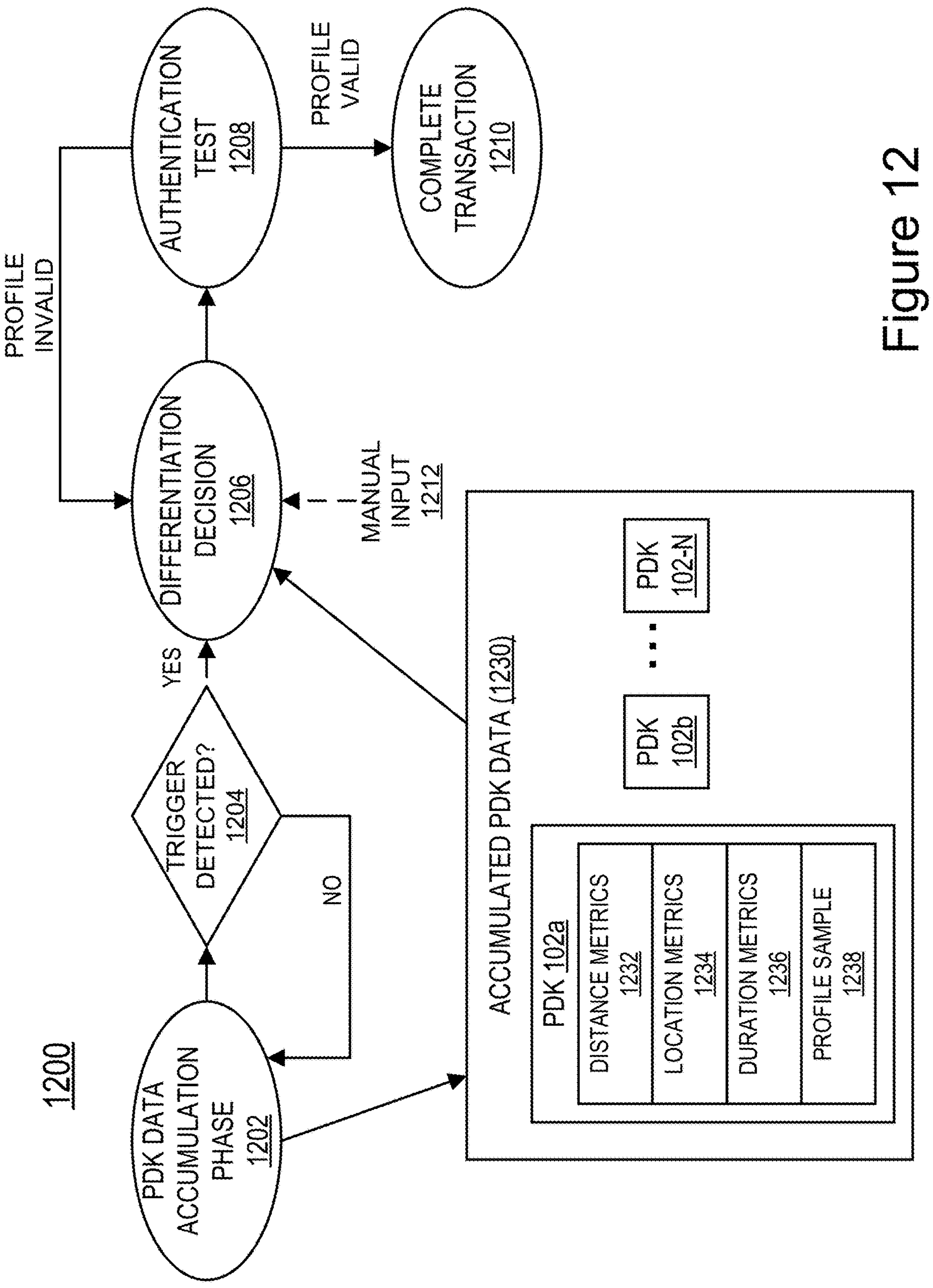
FIG. 12 is a flowchart of a method for differentiating between multiple PDKs within the proximity zone of a reader in accordance with the present invention.

FIG. 12 illustrates an embodiment of an authentication method 1200 for the scenario where multiple PDKs 102 are present within a proximity zone 1102 or directional proximity zone 1104 of a Reader 108. In a PDK data accumulation phase 1202, PDK data 1230 is accumulated and buffered in the Reader 108 for any valid PDKs 102 that enter the proximity zone 1102 or the directional proximity zone 1104. In one embodiment, the accumulation phase 1202 begins for a PDK 102 after it has been within the proximity zone 1102, or directional proximity zone 1104, for a predetermined period of time. In one embodiment, the PDK data accumulation phase 1202 is similar to the steps 702-708 described above in detail with reference to FIG. 7 for each PDK 102*a-d* in the proximity zone 1102 or the directional proximity zone 1104.

As illustrated, the accumulated PDK data 1230 includes one or more differentiation metrics from each valid PDK 102 within range of the Reader 108. The differentiation metrics can include any information that can be used by the Reader 108 to determine which PDK 102 should be associated with the authentication and/or transaction request. According to various embodiments, differentiation metrics can include one or more of distance metrics 1232, location metrics 1234 and duration metrics 1236.

In one embodiment, a distance metric 1232 indicates the relative distance of a PDK 102 to the Reader 108. This information is useful given that a PDK 102 having the shortest distance to the Reader 108 is generally more likely to be associated with a received authentication trigger (e.g., a biometric input, a PIN input or a transaction request). The distance metrics 1232 can include, for example, bit error rates, packet error rates and/or signal strength of the PDKs 102. These communication measurements can be obtained using a number of conventional techniques that will be apparent to those of ordinary skill in the art. Generally, lower error rates and high signal strength indicate the PDK 102 is closer to the Reader 108.

Location metrics 1234 can be used to determine a location of a PDK 102 and to track movement of a PDK 102 throughout an area or locate the PDK in an area. This information can be useful in determining the intent of the PDK holder to execute a transaction. For example, a PDK holder that moves in a direct path towards a cashier and then stops in the vicinity of the cashier is likely ready to make a purchase (or may be waiting in line to make a purchase). On the other hand, if the PDK 102 moves back and forth from the vicinity of a cashier, that PDK holder is likely to be browsing and not ready to make a purchase. Examples of systems for determining location metrics are described in more detail below with reference to FIGS. 13-14.

The differentiation metrics can also include duration metrics 1236 that tracks the relative duration a PDK 102 remains within the proximity zone 1102 or within the directional proximity zone 1104. Generally, the PDK 102 with the longest time duration within the proximity zone 1102, or the directional proximity zone 1104, is most likely to be associated with the authentication request. For example, if the Reader 108 is busy processing a purchasing transaction at a cashier and another PDK 102 has a long duration within the proximity zone 1102 or the directional proximity zone 1104, it is likely that the user is waiting in line to make a purchase. In one embodiment, the Reader 108 tracks duration 1236 by starting a timer associated with a PDK 102 when the PDK 102 enters the proximity zone 1102, or the directional proximity zone 1104, and resetting the time to zero when the PDK 102 exists. As another example, the Reader 108 tracks the duration when a PDK 102 of a doctor enters the proximity zone of a patient's room. A long duration of the doctor's PDK 102 within the proximity zone can provide evidence that the doctor is spending an adequate amount of time examining the patient. On the other hand, a short duration of the doctor's PDK 102 within the proximity zone can provide evidence that the doctor just merely stopped by and did not perform any thorough examination. This information is useful in monitoring patient treatment and provider performance to help ensure quality patient care.

In some embodiments, the PDK 102 sends responses at a system-defined rate. For example, in one embodiment, the RDC 504 and PDK 102 are configured such that the RDC 504 receives a response including one or more differentiation metrics from the PDK 102 every 100 milliseconds (i.e., the system-defined rate). In some embodiments, the PDK 102 sends responses at an independently-defined rate. For example, in one embodiment, the independently-defined rate is based at least in part on the detection of movement. In one such embodiment, a PDK 102 that is sitting idle (e.g., a piece of unused equipment in a supply closet) may reduce its response rate to the RDC 504 in order to conserve power, and when movement is detected (e.g., based on changing distance metrics 1232), the PDK 102 increases its response rate (e.g., to allow near real-time tracking).

In some embodiments, different types of PDK 102 have different response rates. For example, assume a PDK 102 for equipment is of a first type and a PDK 102 for individuals such as a patient or provider is a second type, in one embodiments, the PDK 102 for equipment has a different response rate than the PDK 102 for individuals. For another example, assume different manufacturers of PDK are configured to respond at different rates, in one embodiments, the PDK 102 from a first manufacturer may (i.e., a first type of PDK) respond at a different rate than the PDK 102 of a second manufacturer (i.e., a second type of PDK).

In one embodiment, the Reader 108 can also receive and buffer profile samples 1238 prior to the start of a profile authentication instead of during the authentication process as described in FIGS. 10A-10B. In one embodiment, the Reader 108 determines which types of biometric profile samples 1238 to request based on, for example, the configuration of the Reader 108, the type of transactions performed by the Reader 108, or manual requests from a clerk, security guard, etc. In one embodiment, the PDK 102 transmits one or more of the requested sample types based on profiles available in the PDK 102 and/or user preferences. In another embodiment, the PDK 102 transmits one or more samples 1238 it has available and only samples that match the authentication types configured for the Reader 108 are buffered. For example, if a Reader 108 is configured for fingerprint authentication, a PDK 102 may transmit samples 1238 for several different fingerprint profiles (each corresponding to a different finger, for example). It will be apparent to one of ordinary skill in the art that other variations are possible to provide flexibility in both the configuration of the Reader 108 for various types of authentication and flexibility for the PDK owner to determine which types of authentication to use.

Because profile samples 1238 only comprise a subset of the profile information, in one embodiment, the samples can be safely transmitted over a public channel without needing any encryption. In another embodiment, the profile samples 1238 are transmitted with at least some level of encryption. In yet another embodiment, some of the data is transmitted over a public communication channel and additional data is transmitted over a secure communication channel. In different configurations, other types of profile information can be accumulated in advance. For example, in one embodiment, a photograph from a picture profile can be obtained by the Reader 108 during the data accumulation phase 1202. By accumulating the profile sample 1238 or other additional information in advance, the Reader 108 can complete the authentication process more quickly because it does not wait to receive the information during authentication. This efficiency becomes increasingly important as the number of PDKs 102 within the proximity zone 1102, or within the directional proximity zone 1104, at the time of the transaction becomes larger. The efficiency also becomes increasingly important as the number of transactions increases. For example, in one embodiment, the transaction is a healthcare provider logging into a computer system with patient charts, which each healthcare provider (e.g., a doctor or nurse) may have to do dozens, scores or over a hundred times a day. In such an example, even a small increase in the efficiency/speed of login for each healthcare provider using the system adds up.

The PDK accumulation phase 1202 continues until a trigger (e.g., detection of a biometric input) is detected 1204 to initiate a profile authentication process. If a biometric input is received, for example, the Reader 108 computes a mathematical representation or hash of the input that can be compared to a biometric profile and computes one or more input samples from the biometric input. It is noted that in alternative embodiments, the process can continue without any trigger. For example, in one embodiment, the transaction can be initiated when a PDK 102 reaches a predefined distance from the Reader 108 or when the PDK 102 remains within the proximity zone 1102, or within the directional proximity zone 1104, for a predetermined length of time.

The process then computes a differentiation decision 1206 to determine which PDK 102*a-d* should be associated with the authentication. In one embodiment, the Reader 108 computes a differentiation result for each PDK 102 using one or more of the accumulated data fields 1230. For example, in one embodiment, the differentiation result is computed as a linear combination of weighted values representing one or more of the differentiation metrics. In another embodiment, a more complex function is used. The differentiation results of each PDK 102 are compared and a PDK 102 is selected that is most likely to be associated with the transaction.

In another embodiment, for example, in a photo authentication, the differentiation decision can be made manually by a clerk, security guard, or other administrator that provides a manual input 1212. In such an embodiment, a photograph from one or more PDKs 102 within the proximity zone 1102 or within the directional proximity zone 1104 can be presented to the clerk, security guard, or other administrator on a display and he/she can select which individual to associate with the transaction. In yet another configuration, the decision is made automatically by the Reader 108 but the clerk is given the option to override the decision.

An authentication test 1208 is initiated for the selected PDK 102. The authentication test 908 can include one or more of the methods illustrated in FIGS. 10A-10D. Note that if profile samples 1238 are acquired in advance, they need not be acquired again in the authentication steps of FIGS. 10A-10B. It is additionally noted that in one embodiment, the Reader 108 compares the profile samples 1238 of the PDKs 102 to the computed input sample until a match is found before performing a full profile comparison. In one embodiment, the Reader 108 first compares samples from the selected PDK 102 until a match is found. For example, a Reader 108 may have accumulated multiple fingerprint profiles samples 1238 (e.g., corresponding to different fingers) for the selected PDK 102. The Reader 108 receives a fingerprint input from, for example, the left index finger, computes the input sample, and does a quick comparison against the accumulated samples 1238 for the selected PDK 102 to efficiently determine a matching profile. The Reader 108 then performs the full comparison using the matching profile. In an alternative embodiment, the Reader 108 performs a comparison of a first sample from each PDK 102 and if no match is found, performs comparisons of second samples from each PDK 102. It will be apparent to one of ordinary skill in the art that samples can be compared in a variety of other orders without departing from the scope of the invention.

If the authentication test 1208 indicates a valid profile, the transaction is completed 1210 for the matching PDK 102. If the authentication test 1208 determines the profile is invalid, a new differentiation decision 1206 is made to determine the next mostly likely PDK 102 to be associated with the transaction. The process repeats until a valid profile is found or all the PDKs 102 are determined to be invalid.

Figure 13:
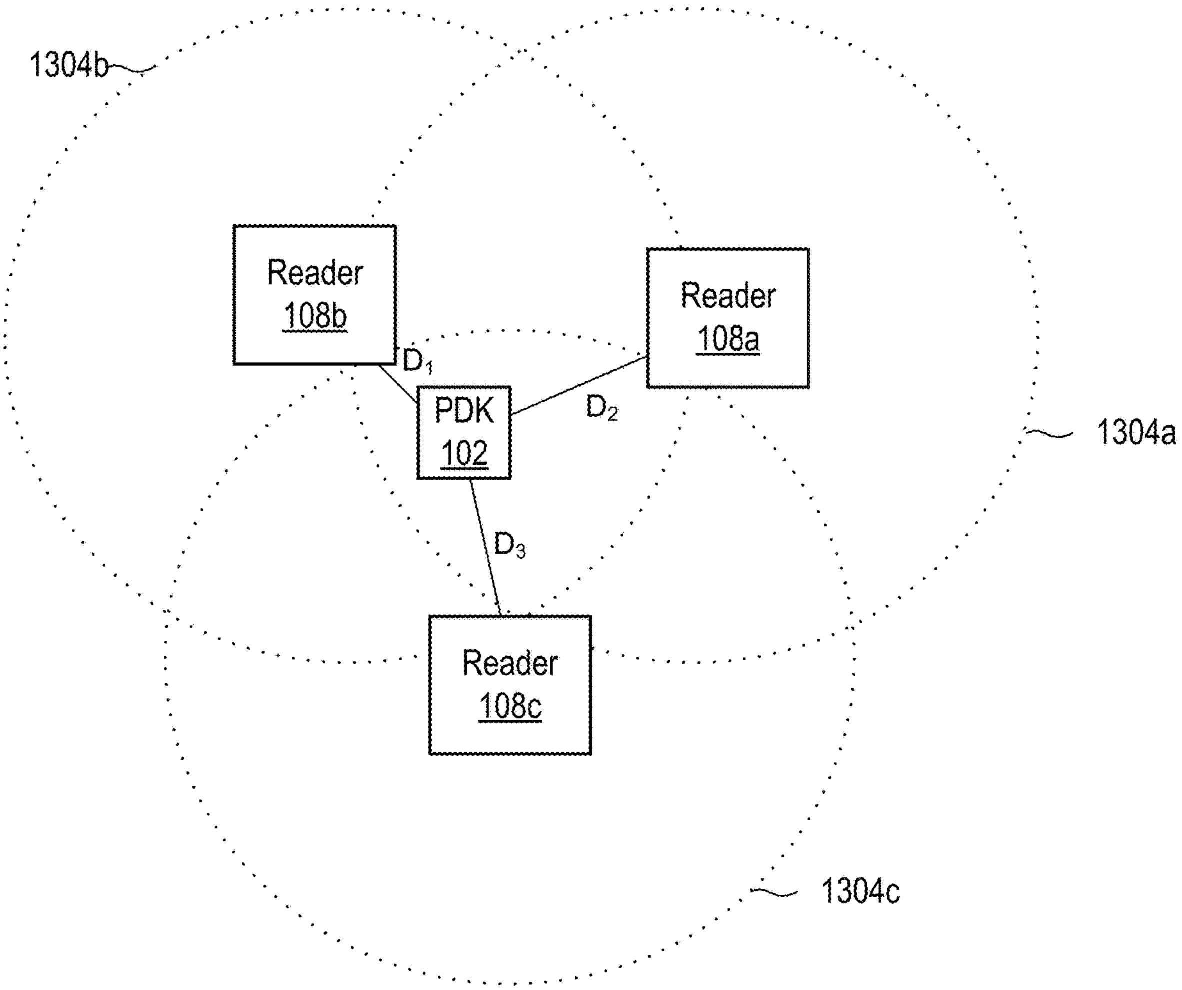
FIG. 13 is a block diagram of a system for estimating location of a PDK using coordinate triangulation in accordance with the present invention.

FIG. 13 illustrates an example system is illustrated for determining a location metric 1234 of a PDK 102 using distance metrics to triangulate the location. In one embodiment of triangulation, multiple transmitting devices (e.g., Readers 108*a-c*) are spaced throughout an area. In one embodiment, the Readers 108*a*-care coupled by a network. Each Reader 108*a-c* has a range 1304 and the ranges 1304 overlap. Each Reader 108*a-c* determines a distance D1-D3 between the Reader 108 and the PDK 102. Distance may be estimated, for example, by monitoring signal strength and/or bit error rate as previously described. Then using conventional trigonometry, an approximate location of the PDK 102 can be calculated from D1-D3. Although only three transmitters are illustrated, it will be apparent that any number of transmitters can be used to sufficiently cover a desired area. Moreover, the any number of sensors may be tied together to create an extended zone, for example, four sensors creating a "Lobby" zone. Location information can be computed at predetermined time intervals to track the movement of PDKs 102 throughout a facility. A person having ordinary skill in the art will recognize that other methods exist for determining a location metric (e.g., nearest sensor) and that one or more of these methods may be used for tracking in the same system alone or in combination. For example, triangulating provider location, using the nearest sensor method for patients, and using both nearest sensor and triangulation for locating equipment.

Figure 14:
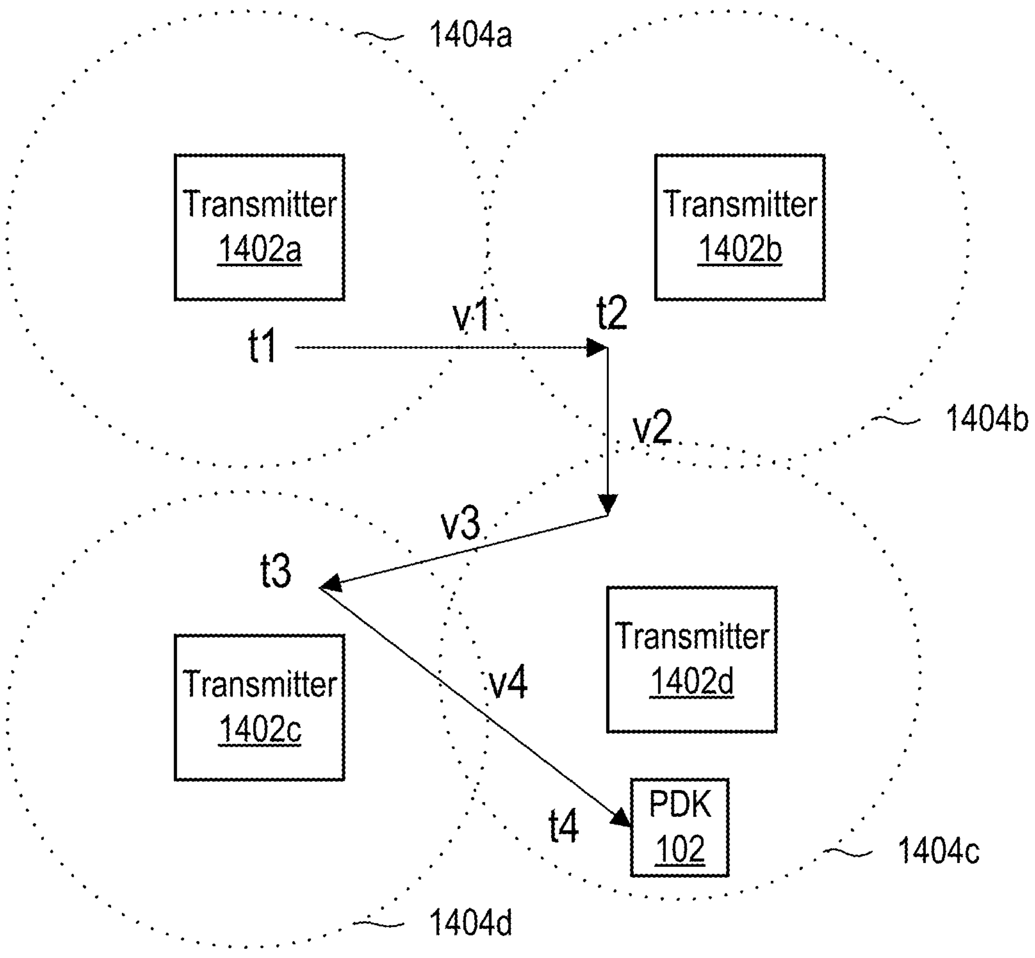
FIG. 14 is a block diagram of an alternative system for location tracking of a PDK in accordance with the present invention.

Another embodiment of location tracking is illustrated in FIG. 14. Here, transmitters 1402 having ranges 1404 are distributed throughout an area. The ranges 1404 can vary and can be overlapping or non-overlapping. In this embodiment, each transmitter 1402 can detect when a PDK 102 enters or exists its range boundaries 1404. By time-stamping the boundary crossings, a location vector can be determined to track the PDK's movement. For example, at a first time, t1, the PDK 102 is detected within the range of transmitter 1402*a*. At a second time, t2, the PDK 102 is detected within the range of transmitter 1402*b*. At a third time, t3, the PDK 102 is within the range of transmitter 1402*c* and at a fourth time, t4, the PDK 102 is within the range of transmitter 1402*d*. Using the location and time information, approximate motion vectors, v1, v2, v3, and v4 can be computed to track the motion of the PDK 102 without necessarily computing exact distance measurements.

In some embodiments, of location tracking one or more of a rule and precedent are applied during location tracking. For example, assume that vector v1 goes through a wall, in one embodiment, a rule that a PDK 102 cannot travel through a wall is applied and when the PDK's route is displayed on a computing device 120 the route will go through a doorway. For another example, again assume that vector v1 as drawn goes through a wall, that t1 and t2 are 5 seconds apart and that a PDK 102 can travel from the location of t1 to the location of t2 by taking one of two routes. In one embodiment, a precedent is applied in which it is determined that the PDK 102 used a first route because the second route has never been taken and/or would take longer than 5 seconds (e.g. based on travel times from previous tracks) and when the PDK's route is displayed on a computing device 120 the route will include the first route from the location of t1 to the location of t2.

A person having ordinary skill in the art will recognize that the resolution of tracking or an item's location can be modified based to suit users' needs. For example, triangulation may be more accurate (better resolution) but requires more readers 108 or transmitters 1402 to create the necessary overlapping coverage than locating/tracking based on presence in a reader's 108/transmitter's 1402 non-overlapping coverage zone.

Figure 15:
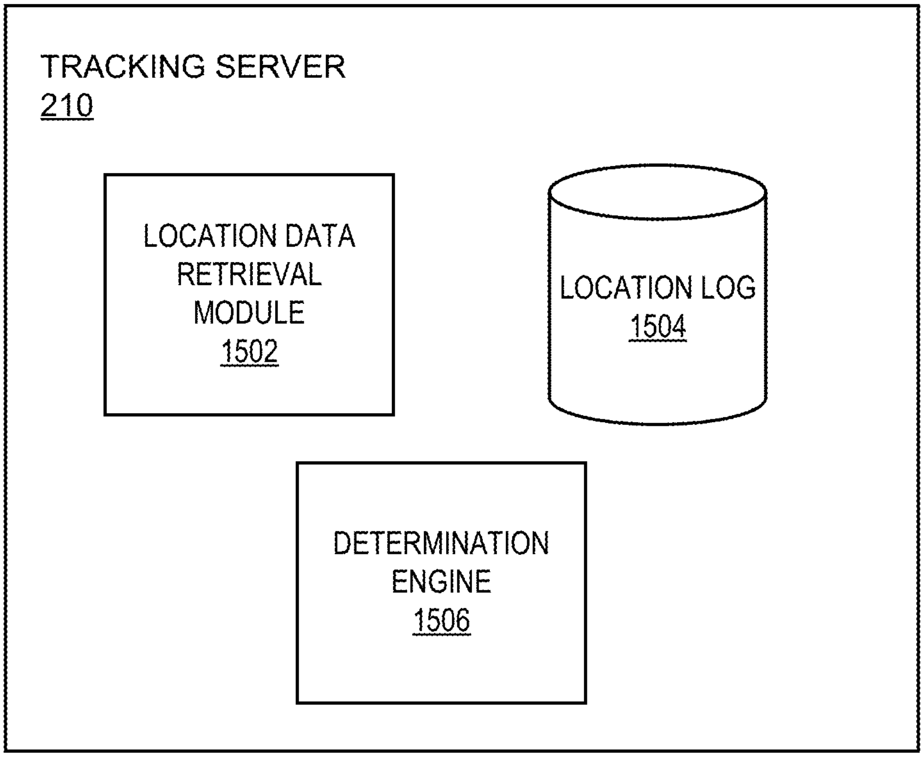
FIG. 15 is a block diagram of a tracking server in accordance with the present invention.

FIG. 15 is a block diagram illustrating an embodiment of a tracking server 210. The tracking server 210 enables real-time tracking of individuals, equipment and supplies by monitoring and storing location information of individuals, equipment or supplies with associated PDKs 102. For example, the tracking server 210 allows rapid location of healthcare providers in case of an emergency, allows monitoring of patient location to ensure timely administration of medications and allows constant monitoring of equipment or supply location to minimize search time and inventory surplus requirements. Moreover, when used in time and motion studies and reports, the tracking data may reveal areas for potential efficiency gains. For example, a time and motion study may reveal that healthcare providers walk repeatedly to a faraway supply closet and by moving the supply closet, more time can be spent with patients increasing the quality of care, the number of patients a provider can examine/treat in a day or both. One embodiment of the tracking server 210 includes a location data retrieval module 1502, a location log 1504 and a determination engine 1506. In one embodiment, the location log 1504 is a database, such as a Structured Query Language (SQL) database. In some embodiments, the tracking server 210 enables tracking and auditing of equipment by monitoring and storing information regarding one or more of the equipment's location, usage, maintenance and calibration. For example, the tracking server 210 allows for the monitoring and auditing of equipment to ensure that equipment remains calibrated and well maintained and allows for the scheduling of use, maintenance and calibration at time when the equipment is not in use or alternative equipment is available. In one embodiment, the location log 1504 stores information regarding one or more of the equipment's location, usage, maintenance and calibration. In another embodiment, the tracking server 210 comprises a service log (not shown), which stores information regarding one or more of the equipment's usage, maintenance and calibration. In one embodiment, the determination engine 1506 retrieves information from the location log 1504 to predict the location of a device.

In one embodiment, multiple Readers 108 are placed at certain and known positions throughout a facility. For example, a Reader is placed above each doorway of every room and at every computing device 120. In another embodiment, Readers 108 are placed in a grid pattern throughout the facility. In one embodiment, entities within the facility carry an associated PDK 102 uniquely identifying the entity and PDKs 102 are attached to different pieces of equipment or supplies within the facility. Example embodiments of a tracking system are described in U.S. patent application Ser. No. 11/939,451 to John Giobbi, et al., entitled "Tracking System Using Personal Digital Key Groups" and filed on Nov. 13, 2007, the entire contents of which are incorporated herein by reference.

Figure 16A:
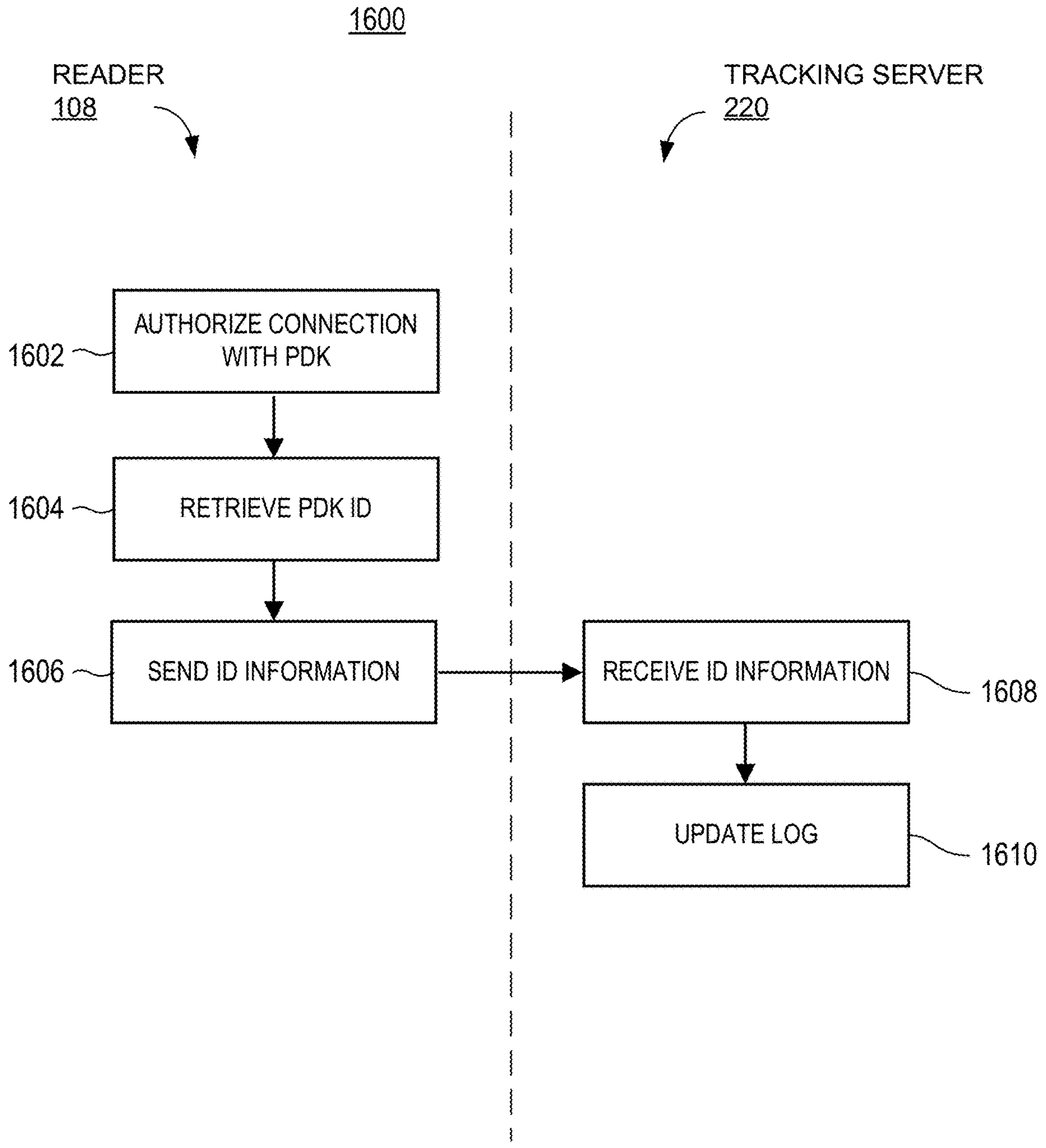
FIG. 16A is a flowchart of a method for tracking assets or users in accordance with the present invention.

A flowchart illustrating one embodiment of a process 1600 for tracking of equipment and individuals is shown in FIG. 16A. When a PDK 102 comes within the range of a Reader 108, connection is authorized 1602 between the RDC 504 of the Reader 108 and the PDK 102. In one embodiment, the RDC 504 continually transmits beacons that are detected by the PDK 102 when it enters a proximity zone of the Reader 108. In an alternative embodiment, the communication is instead initiated by the PDK 102 and acknowledged by the Reader 108. As shown in the previous FIG. 7, device authentication is first performed and once the Reader 108 establishes if the PDK 102 is a valid device and PDK 102 establishes if the Reader 108 is valid, connection can be authorized.

Once connection is authorized 1602, the Reader 108 retrieves 1604 the PDK 102 information, such as PDK ID 312 and other information identifying the owner or entity associated with the PDK 102. In one embodiment, the reader ID 518 of the Reader 108 is sent to the PDK 102 and stored in the activity log 390 of the PDK 102. In one embodiment, the sensor reading (e.g., temperature readings) are also stored in the activity log allowing for temperature tracking instead of or in addition to location tracking. The reader and PDK information (including the activity log 390) is sent 1606 to the tracking server 210. The location data retrieval module 1502 receives 1608 the PDK information, including the PDK ID 312. The information is updated 1610 in the location log 1604 of the tracking server 210.

In one embodiment, the location log data is retrieved by the computing device 120. In such embodiments, the computing device 120 displays the locations of the individuals and equipment being tracked; therefore making it possible to locate anyone and any piece of equipment at any given moment. In some embodiments, the location log data is displayed graphically, for example, with a map of the facility and indications on the map identifying locations of tracked items and people. In other embodiments, the location log data is displayed on the computing device 120 with text describing the locations of the tracked items and people.

Figure 16B:
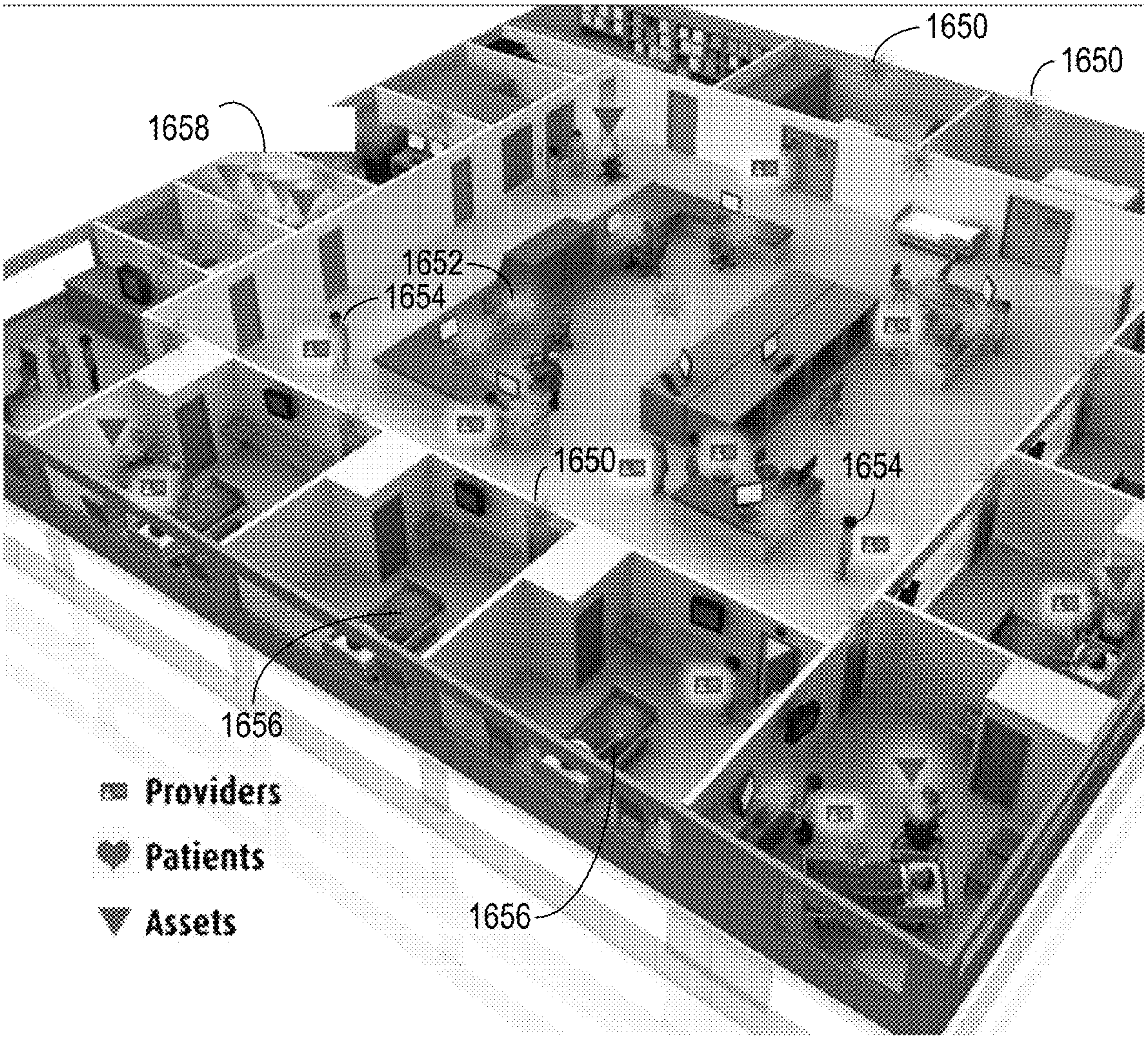
FIG. 16B is a graphical representation illustrating an example where patient, provider and equipment tracking is provided within a healthcare facility.

This process 1600 occurs whenever a PDK 102 enters the proximity zone of each Reader 108 that it passes enabling constant tracking and location of individuals carrying PDKs 102 and equipment with affixed PDKs 102. FIG. 16B is a graphical representation illustrating an example where patient, provider and equipment tracking is provided within a healthcare facility. Readers 1650 are located at various locations throughout the healthcare facility to receive PDK information. Computing devices are also equipped with readers 1652 for receiving PDK information. The Readers 1650 and 1652 receive information from the provider PDKs 1654, patient PDKs 1656 and equipment PDKs 1658 enabling the location and tracking of providers, patients and equipment anywhere throughout the healthcare facility.

In another embodiment, the determination engine 1506 uses the data stored in the location log 1504 to predict the location of a device. The determination engine 1506 uses the data collected and by the multiple Readers 108 that are placed at certain and known positions throughout a facility. In one embodiment, the determination engine 1506, via the tracking server 210, is communicatively coupled to output data to the Reader 108. In such embodiments, the determination engine 1506 outputs information to the Reader 108 modify various signals of the Reader 108 to further refine the Reader's 108 performance and functionality. For example, in one embodiment, the determination engine 1506 could use the information collected to change the signal strength of the Reader 108.

Figure 17:
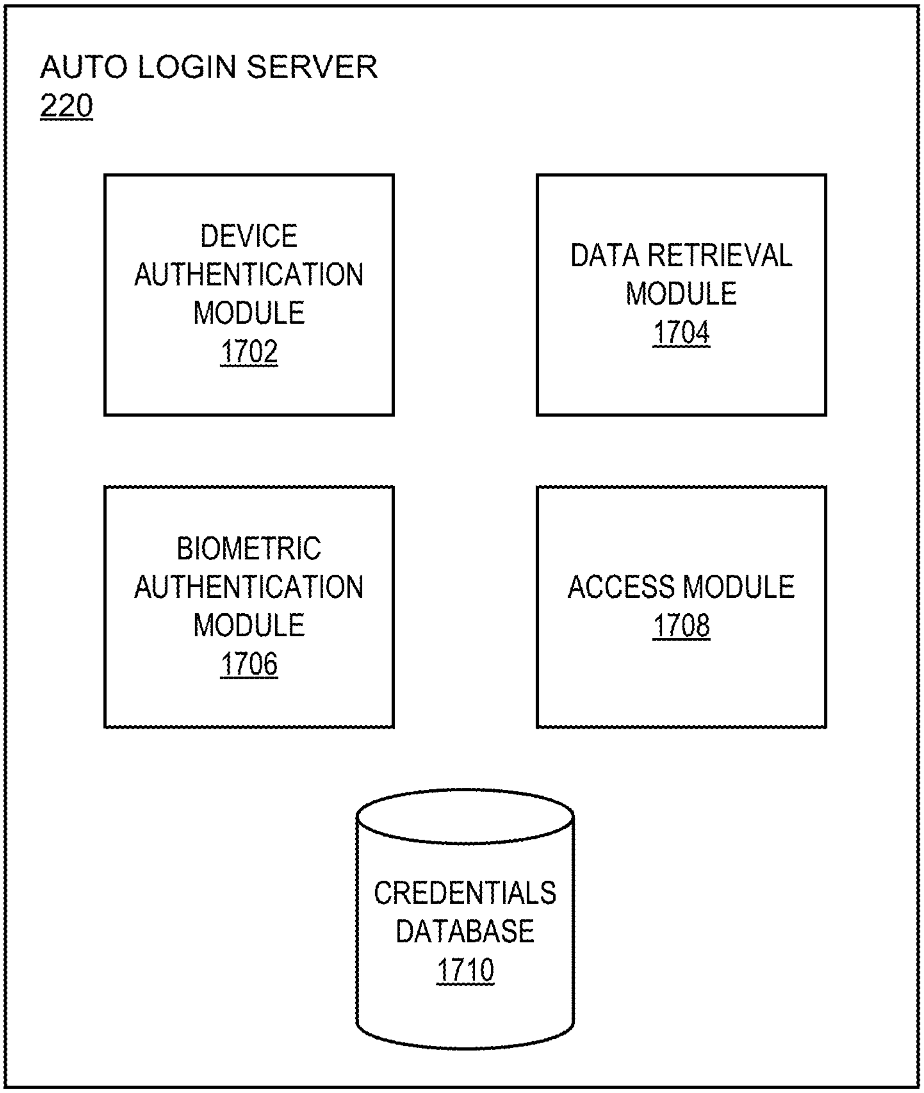
FIG. 17 is a block diagram of an auto login server in accordance with the present invention.

FIG. 17 is a block diagram illustrating an embodiment of an auto login server 220. The auto login server 220 allows for automated electronic signing on of providers into the healthcare computer system, therefore eliminating the constant and time-consuming login and logout of healthcare providers such as doctors, nurses, physician assistants, medical technicians, and other caregivers. A person having ordinary skill in the art will recognize that references to the healthcare system and healthcare providers in this specification are used by way of example and not by limitation. For instance, the auto login server 220 allows for automated electronic signing on of any type of user into any type of computer system. In one embodiment, providers can utilize their PDKs 102 to automatically log in to the application software system by simply approaching or entering the proximity zone of a Reader 620 of a computing device 120. In such embodiments, no manual input is necessary. The auto login server 220 includes a device authentication module 1702, a data retrieval module 1704, a biometric authentication module 1706, an access module 1708 and a credentials database 1710. In some embodiments the auto login server resides in the local services module 124. The auto login server includes input and output ports for receiving data from and sending data to one or more Readers 108. The device authentication module 1702 is coupled to the biometric authentication module 1706 and data retrieval module 1704. The data retrieval module 1704 is couple to communicate with the access module 1708, which is further configured to send access authorization to readers 620, 108 and computing device 120. The access module 1708 is coupled to the credentials database 1710 for comparing the received data with data stored in a credentials database 1710.

Figure 18:
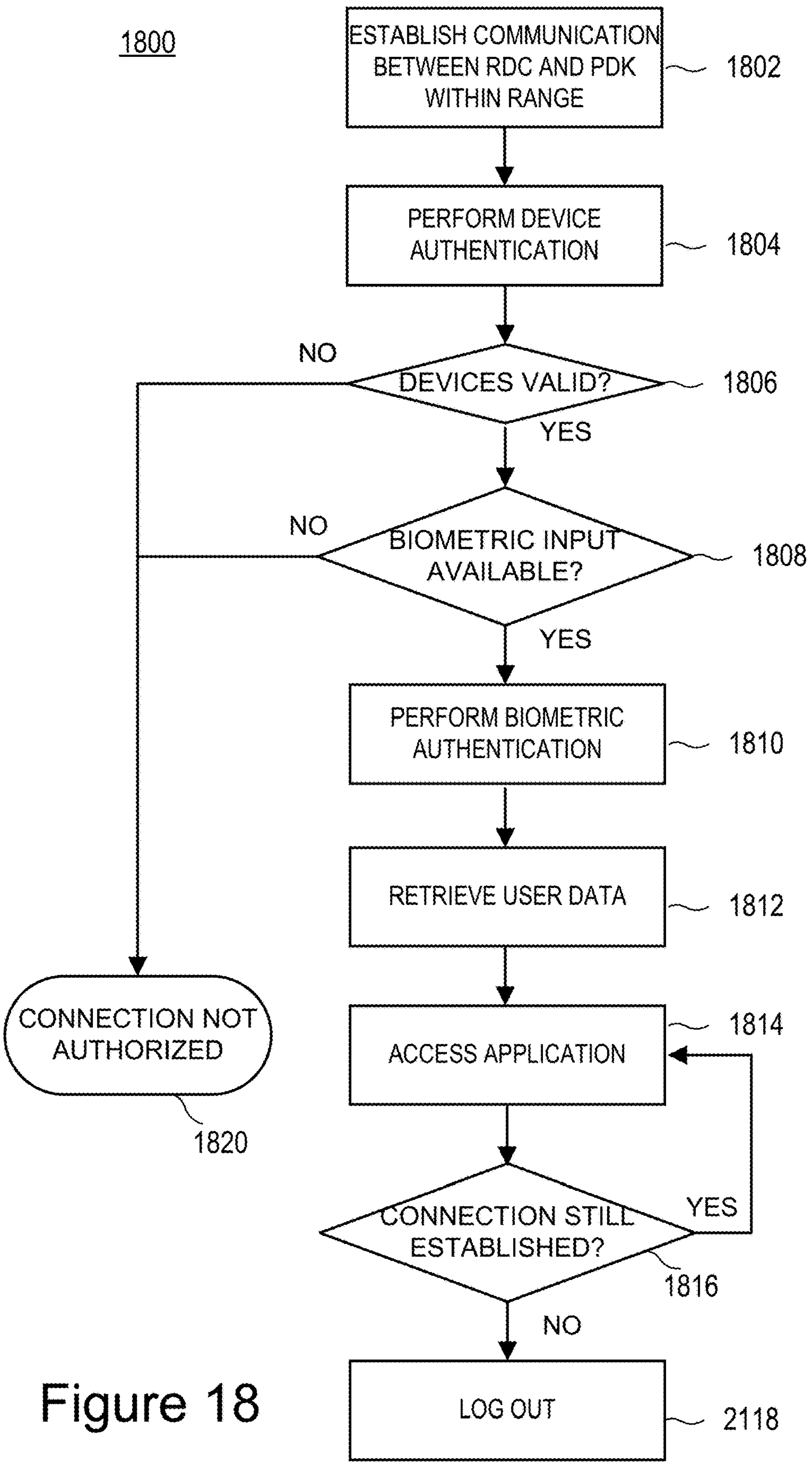
FIG. 18 is a flowchart of a method for automatic login of a user in accordance with the present invention.

FIG. 18 is a flowchart illustrating one embodiment of a method 1800 for automatic login of a user. When a user carrying or wearing a PDK 102 comes within the range of a Reader 620 communicating with a computing device 120, communication is automatically established 1802 between the RDC 504 of the Reader 620 of a computing device 120. In one embodiment, the PDK 102 is incorporated into an identification badge of the user. Once communication with the PDK 102 is established, device authentication is performed 1804.

In one embodiment, the device authentication module 1702 performs 1804 device authentication. In another embodiment, the device authentication is performed by the Reader 108 as described in step 704 of FIG. 7. An example embodiment of a method for performing 1804 device authentication is illustrated in the previous FIG. 8. In one embodiment, the device authentication is performed 1804 responsive to a user accessing an application 630 for execution by the computing device 120. For example, a user selects an application from a user bar or accesses an application 730 using the operating system of the computing device 120.

Next, the device authentication module 1702 determines 1806 whether the PDK 102 is valid. If the PDK 102 is found to be invalid, connection is not authorized 1816 and the process ends without the logging in of the user.

In one embodiment, if the PDK 102 is found to be valid, the biometric authentication module 1706 determines 1806 if biometric information is available. In one embodiment, the requirement for biometric input is configurable by an administrator. For example, in one embodiment, an administrator can configure the system to not require biometric input.

If biometric information is available, the biometric authentication module 1706 performs 1810 biometric authentication. In one embodiment, a provider provides biometric information by swiping their finger on a Reader 108 of the computing device 120. In another embodiment, the provider provides biometric information by entering a PIN number. In yet another embodiment, the provider provides biometric information be swiping their finger on the biometric reader 370 of the PDK 102. If biometric information is not available (the provider has not swiped his finger or entered a PIN number), connection is not authorized 1820 and the process ends. If biometric information is available, biometric authentication is performed 1810. Example embodiments for performing authentication, such as biometric authentication, are described above in conjunction with FIGS. 10A-D.

In one embodiment, biometric authentication is performed 1810 responsive to an accessed application requesting or requiring biometric authentication. For example, responsive to a user accessing an application from an application menu of the computing device 120, the computing device 120 determines whether a biometric check is needed by the accessed application. If a biometric check is needed by the accessed application, the computing device 120 communicates with the Reader 108 to perform 1818 biometric authentication. In one embodiment, the computing device 120 or the application server 240 includes a database specifying whether or not an application performs a biometric check.

Once biometric authentication is performed 1810, or if biometric authentication is not needed, the data retrieval module 1704 of the registration server 205 retrieves 1812 information from the PDK 102 of the user and the access module 1708 allows 1814 the user to access one or more applications. For example, the user is allowed 1814 to access one or more applications from the application server 240. In some embodiments where biometric authentication is not required, the access module 1708 compares the received data with data stored in the credentials database 1710 to allow or deny access. In one embodiment, once biometric authentication is completed, or is not required, the user is not only allowed to access one or more applications, but one or more applications are automatically launched.

In one embodiment, the data retrieval module 1704 identifies a service block of a registry profile stored by the PDK 102 to the computing device 120, which identifies the service block to the Reader 108, which retrieves 1812 data from the identified service block. For example, the data retrieval module 1704 identifies a registry identifier to specify a service block and the Reader 108 retrieves 1812 a record identifier and a key from the service block. The Reader 108 communicates the retrieved 1812 record identifier and the key and a PDK ID to the application server 240 in addition to a request to launch the accessed application.

In one embodiment, the accessed application 630 of the computing device 120 communicates the data retrieved from the PDK 102 to the application server 240, which communicates login credentials associated with the application 630 to the computing device 120. The computing device 120 uses the login credential information access the application 630. For example, the application 630 communicates a PDK ID, a record identifier and a key retrieved form the PDK 102 to the application server 240, which identifies a login and password from the PDK ID, the record identifier and the key. The login and password are communicated from the application server 240 to the computing device 120, which uses the login and password to launch the application 630. In another embodiment, the application 630 of the computing device 120 retrieves the login credential information associated with the data retrieved form the PDK 102 from the credentials database 320 to allow 1814 access to one or more applications. Allowing 1814 access to one or more applications is further described below in conjunction with FIG. 19.

In some embodiments, provider identifying information is stored in the PDK 102. As long as connection is established (1816—Yes) (the provider is in the proximity zone of the reader 620 of the computing device 120), access is allowed

1814. If the provider steps outside the proximity zone of the reader 620, connection is no longer established (1816—No) and the provider is automatically logged out 1818 of the application server 240. In one embodiment, the provider is logged out 1818 after a brief delay, e.g., 5 seconds after the connection is no longer established (1816—No). Those skilled in the art will recognize that depending on the level of authentication desired, the need for steps 1808 and 1810 may be omitted.

In some embodiments, various rules are applied. In one embodiment, one or more user-specific criteria (e.g. biometric input, a password, etc.) is required for users who have not logged in for an extended period of time. For example, assume the user has not logged in for many hours, in one embodiment, it is assumed that the user has left for the day and the user will have to provide user-specified criteria to log in when the user returns. In one embodiment, the extended period of time is eight hours. In another embodiment, the extended period of time is twenty four hours. It will be recognized that the preceding are merely examples of extended periods of time and that other examples and embodiments exist.

In one embodiment, the user, after providing a user-specific criteria, can subsequently log in without providing the user-specified to log in for a specified time interval. For example, assume the user provides a biometric input and logs in at the beginning of the user's shift, in one embodiment, the user can subsequently log in without again providing the biometric input for the duration of the user's shift (e.g. 8 hours). It will be recognized that the preceding is merely an example of a time interval and that other examples exist.

In some embodiments, one or more of the extended period of time and the specified time interval can be user defined or customizable, for example, by the user and/or an administrator. In some embodiments, one or more of the extended period of time and the specified time interval can be based at least in part on the workstation. For example, the user may be able to subsequently log into a private workstation for 8 hours without being required to provide another biometric input; however, the user is only able to subsequently log into a public workstation for 1 hour without being required to provide another biometric input. It will be recognized that the preceding is merely one example of basing one or more of the extended period of time and the specified time interval at least in part on the workstation.

In one embodiment, a secure screen saver is utilized in place of a full login/logout procedure. In another embodiment, the system allows for multiple users to be simultaneously logged in to a single workstation. In one embodiment, priority rules and/or user hierarchies are established enabling a higher-level user to override or takeover a lower-level user's session or workstation with or without (depending on the embodiment) the lower-level user's permission.

Figure 19:
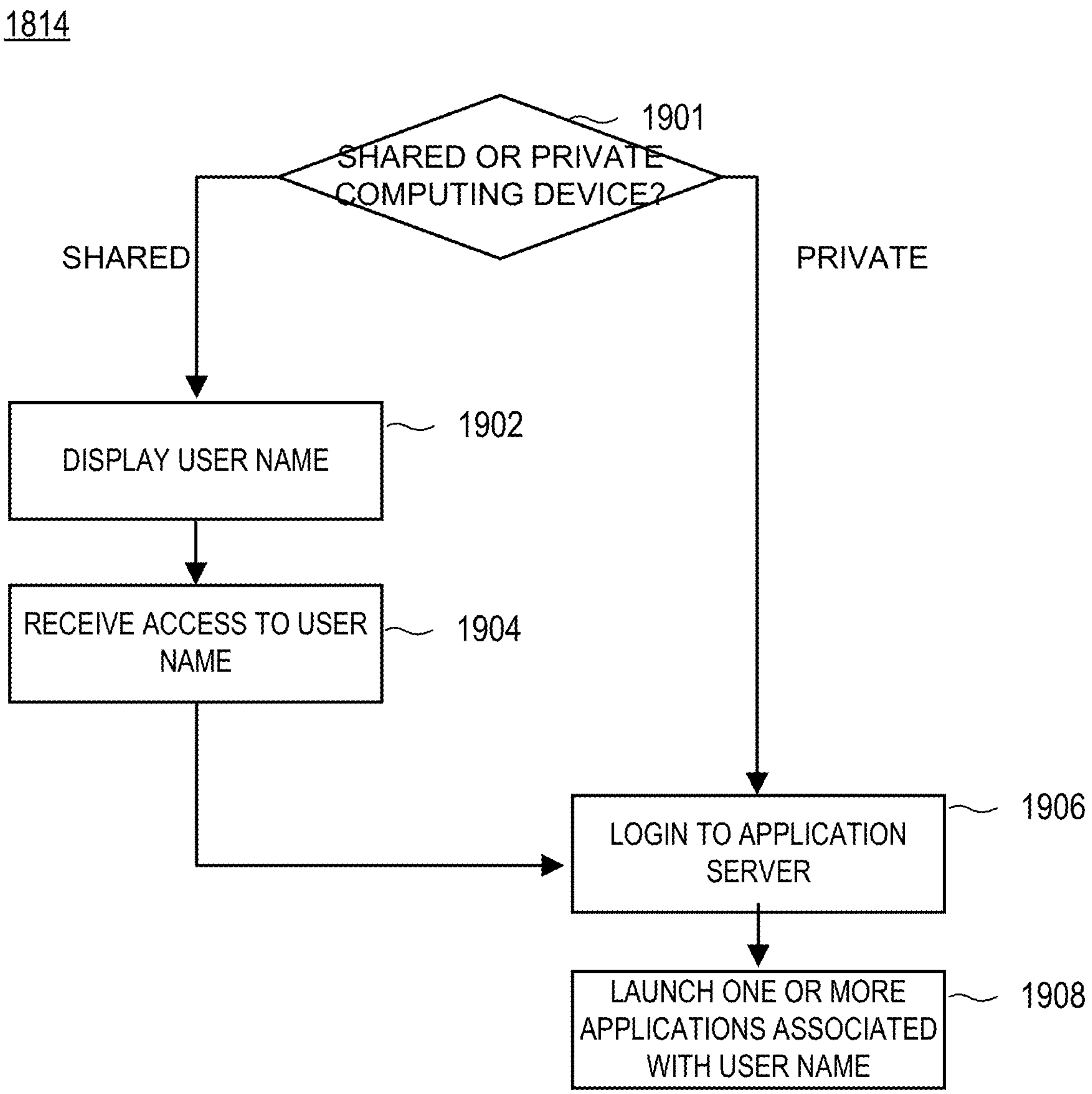
FIG. 19 is a flowchart of a method for automatically allowing access to one or more applications in accordance with the present invention.

FIG. 19 is a flowchart of one embodiment of a method 1814 for automatically allowing access to one or more applications. Initially, it is determined 1901 whether the computing device 120 is shared or private. A shared computing device 120 is able to be automatically accessed by users associated with a plurality of PDK IDs. A private computing device 120 is able to be automatically accessed by a user associated with a specific PDK ID. For example, a shared computing device 120 is included in a location where it is accessible by multiple users, such as in a clinic room or examination room in a healthcare facility for use by different healthcare providers, while a private computing device 120 is included in a location where its accessible by a specific user, such as in a doctor's office of a healthcare facility for use by a specific doctor. In one embodiment, data included in the computing device 120 indicates whether the computing device 120 is shared or public.

In an alternative embodiment, rather than determine 1901 whether the computing device 120 is shared or private, the computing device 120 determines whether a user associated with the PDK 102 is a shared user or a private user. When a PDK 102 associated with a shared user communicates with a Reader 620, the computing device 120 coupled to the Reader 620 displays 1902 the user name of the user associated with the PDK 102, as further described below. Thus, if multiple PDKs 102 associated with shared users are within the proximity zone of the Reader 620, the computing device 120 communicating with the Reader 620 displays user names associated with the different shared users, and an application is not launched until one of the displayed user names is selected, as further described below. In one embodiment, if only one PDK 102 is present within the proximity zone of the reader 620, the user's name is still displayed and an application is not launched until the user name associated that PDK 102 is selected. In one embodiment, the user can select ad hoc one or more applications in addition to the user's user name, and the one or more ad hoc selected applications will launch instead of or in addition to (depending on the embodiment) the one or more applications associated with the user for auto launch. If a PDK 102 is associated with a private user, when the PDK 102 is within the proximity zone of the Reader 620, the private user is logged into 1906 the application server 240 without displaying one or more user names. Thus, when a PDK 102 associated with a private user is within the proximity zone of a Reader 620, the private user is logged into 1906 the application server 240, as further described below.

If the computing device 120 is shared, after biometric authentication is performed 1810 and the data retrieval module 1704 of the registration server 205 retrieves 1812 information from the PDK 102 of the user, the computing device 120 displays 1902 a user name associated with the information from the PDK 102. In one embodiment, if multiple PDKs 102 are within the proximity zone of the Reader 620, and the computing device 120 is shared, the computing device 120 displays 1902 user names associated with each of the PDKs 102 within the proximity zone of the Reader 620.

The computing device 120 receives 1904 an input accessing the displayed user name. If multiple user names are displayed 1902, the computing device 120 receives 1904 an input accessing one of the displayed user names. In one alternative embodiment, the differentiation metrics discussed above are used to determine which PDK and associated user to access or select, e.g., the user associated with the PDK 102 closest to the computing device 120. It should be noted that a person having ordinary skill will recognize that the order of the preceding steps may be altered, e.g., displaying user names after device authentication but prior to biometric authentication, or requiring a user name to be selected before performing biometric authentication. The computing device 120 or the Reader 604 then logs into 1906 the application server 240, or to the application 630, using credentials associated with the accessed user name. Using the credentials associated with the accessed user name, the computing device 120 automatically launches 1908 one or more applications associated with the accessed user name.

For example, the application server 240 associates one or more applications with the accessed user name, and responsive to the computing device 120 receiving 1904 an access to the user name, the application server 240 communicates data to the computing device 120 to launch 1908 the one or more applications associated with the accessed user name. In one embodiment, the applications associated with the user name are stored in the application server 240 as a scenario and a user specifies a default scenario to identify applications that are automatically launched 1908 when a user is automatically logged into a computing device 120 using data stored on a PDK 102. In one embodiment, the user specifies the one or more applications associated with the accessed user name or default scenario (depending upon the embodiment). In another embodiment, the one or more applications associated with the accessed user name or default scenario (depending upon the embodiment) are specified by an administrator upon enrollment of the PDK either explicitly or implicitly, e.g., associating the PDK's 102 user with a group implicitly assigns the group's default scenario to the user. In another embodiment, the one or more applications associated with the accessed user name or default scenario (depending upon the embodiment) is initially specified by the administrator, but may be subsequently changed/personalized by the user associated with the PDK. In some embodiments, an administrator determines what applications a given user and/or computing device 120 may access and the user may change the one or more application associated with the accessed user name or default scenario (depending upon the embodiment) subject to the determination, or permissions granted, by the administrator. For example, the administrator uses a third party application (i.e., an application that is inaccessible to the user and not part of the computing device's operating system) to provide permission for the user to access one or more applications and associate the user name with his/her user name or create a default scenario.

In some embodiments, the one or more applications that are accessible and/or automatically launched may be based at least in part on the computing device 120 being accessed. Such embodiments beneficially provide greater customization and may improve security. For example, in some embodiments, for security reasons certain applications may be prohibited from launching on particular computing devices 120 such as public computing devices. For another example, the user may want a first set of applications to launch in the user's office and a second set of applications to launch at a workstation. It will be recognized that the preceding are merely examples of the one or more applications that are accessible and/or automatically launched may be based at least in part on the computing device 120 being accessed and that other examples exist.

In one embodiment, the user can select one or more applications to auto launch upon login ad hoc. For example, a shared user approaches a computing device 120 selects the user's username and one or more applications from a runtime menu (not shown). Without further input the user is automatically signed in and the one or more applications selected from the runtime menu are automatically launched.

The user's self selection of user name has the benefit of allowing for quick user switching while ensuring that each user logs into his or her account for audit purposes. For example, in one embodiment, a first user after utilizing the computing device 120 logs off either manually or by leaving the proximity zone of the computing device's 120 Reader 108, and the next user can simply login by clicking on his/her user name automatically launching one or more applications.

If the computing device 120 is private, after biometric authentication is performed 1810 and the data retrieval module 1704 of the registration server 205 retrieves 1812 information from the PDK 102 of the user, the computing device 120 or the Reader 620 then logs into 1906 the application server 240, or to the application 630, using credentials associated with the accessed user name. Using the credentials associated with the accessed user name, the computing device 120 launches 1908 one or more applications associated with the accessed user name. Hence, a private computing device 120 automatically launches 1908 one or more applications when the PDK 102 associated with a user authorized to use the private computing device 120. For example, when the PDK 102 associated with a doctor enters the proximity zone of the Reader 620 associated with a computing device 120 in the doctor's office, the computing device 120 automatically launches one or more applications associated with the doctor.

In addition to automatically launching one or more applications when a PDK 102 associated with a user is within a proximity zone of a reader coupled to a computing device 120, the auto login server 220 and/or the application server 240 allow a user to customize the one or more applications launched by the computing device 120. In some embodiments, the auto login server and/or the application server 240 also modify the one or more launched application responsive to user interaction with previously launched applications.

Figure 20:
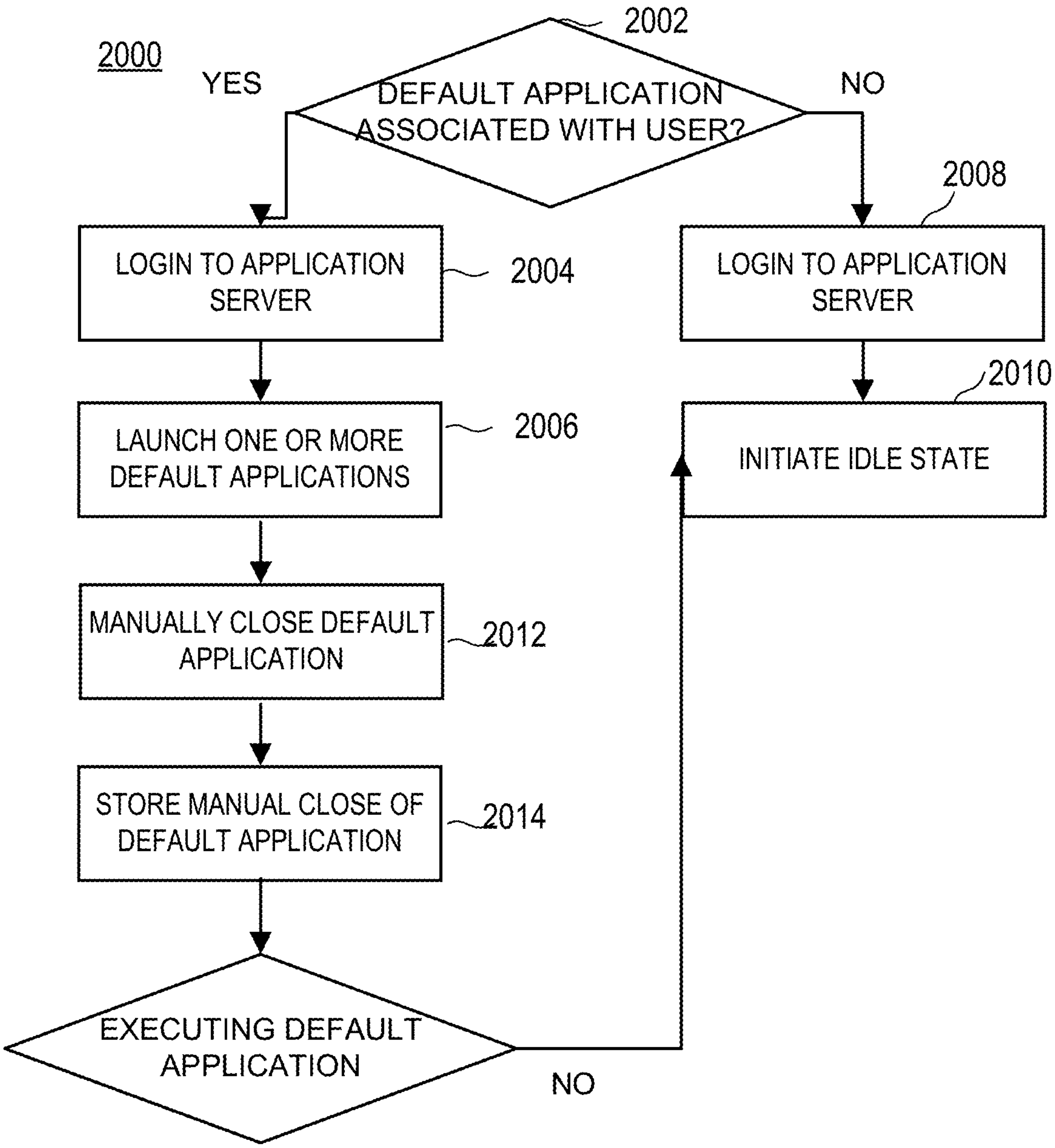
FIG. 20 is a flowchart of a method for identifying one or more applications launched when a user is within the proximity zone of a reader in accordance with the present invention.

FIG. 20 illustrates one embodiment of a method 2000 for identifying one or more applications automatically launched for a user when the user is proximate to a Reader 620. Initially, the auto login server 220 determines whether one or more default applications are associated with a user identified from a PDK 102. A default application is automatically launched when data from a PDK 102 authenticates a user to access a computing device 120. In one embodiment, the auto login server 220 determines 2002 whether one or more default applications are associated with a user and logs in 2004 to the application server 240 using login credentials identified from the data received from the PDK 102. Alternatively, the application server 240 determines 2004 whether one or more default applications are associated with the user.

If one or more default applications are associated with a user, the application server 240 launches 2006 the one or more default applications by communicating data associated with the one or more default applications to a computing device 120 coupled to the Reader 620 from which the auto login server 220 or the application server 240 received data from the PDK 102. In one embodiment, the application server 240 applies application-specific preferences when launching 2006 a default application. For example, the application server 240 associates an application location preference with a user, so that when a default application is launched 2006 the application location preference identifies a specific location within the default application that is initially accessed. For example, the application server 240 identifies a specific text entry region of an application and when the application is launched the specified text entry region is accessed, allowing a user to begin entering text data in the specified text entry region without first selecting the text entry region. While described above in conjunction with default applications, in an embodiment the user's application specific preferences are also applied when a user manually launches an application, allowing the application server 240 to provide increased user-customization to simplify application use. In one embodiment, the user can specify one or more application-specific preferences. In another embodiment, one or more application-specific preferences are specified by an administrator upon enrollment of the PDK either explicitly or implicitly, e.g., by associating the PDK's 102 user with a group having default application-specific preferences. In another embodiment, one or more application-specific preferences are initially specified by the administrator, but may be subsequently changed/personalized by the user associated with the PDK.

After a default application is launched 2006, a user may manually close 2012 the default application by interacting with the default application using the computing device 120. When a user manually closes 2012 a default application, the computing device 120 communicates data to the auto login server 220 and/or the application server indicating that the default application has been manually closed. The auto login server 220 or the application server 240 stores 2014 data indicating that a default application has been manually closed. In one embodiment, when a user logs out of the computing device 120 and does not exit the proximity zone of the Reader 620 coupled to the computing device 120 after manually closing the default application, the manually closed default application is not automatically launched 2006 when the user again logs into the computing device 120. For example, if a user logs off of the computing device 120 after manually closing a first default application and does not exit the proximity zone of the Reader 620, when the user again logs in to the computing device 120, based on the stored data, the auto login server 220 or the application server 240 does not automatically launch the first default application. However, once the user leaves the proximity zone of the Reader 620 after manually closing the first default application, once the user re-enters the proximity zone of the Reader 620 and logs into the computing device 120, the auto login server 220 or the application server 240 again automatically launches 2004 the first default application.

If a user manually closes each default application associated with the user, the application server 240 communicates data to the computing device 120 indicating that no applications are executing, causing the computing device 120 to initiate 2010 an idle state where the user is logged into the computing device 120 and to the application server 240, allowing the user to manually launch one or more applications from the computing device 120.

However, if no default applications are associated with a user, the application server 240 communicates with the computing device 120 coupled to the Reader 620 from which the auto login server 220 or the application server 240 received data from the PDK 102 to initiate 2010 an idle state. In one embodiment, the application server 240 communicates data to the computing device 120 indicating that no applications are executing, causing the computing device 120 to initiate 2010 the idle state.

The Reader 620 and PDK 102 may also be used to lock a computing device 120 coupled to the Reader 620 in addition to limiting use of the computing device 120. For example, the Reader 620 and PDK 102 may be used to limit execution of certain applications using the computing device 120 while allowing users to use other applications locally stored on the computing device 120. For example, the PDK 102 and Reader 620 are used to limit the users permitted to execute a set of healthcare applications, such as a patient record editor, while additional users may freely access a web browser included on the computing device 120. However, in some embodiments, it is desirable to further limit use of the computing device 120 so that users are unable to access applications using the computing device 120 unless a valid PDK 102 associated with the user is in the proximity zone of a Reader 620 coupled to the computing device 120.

Figure 21:
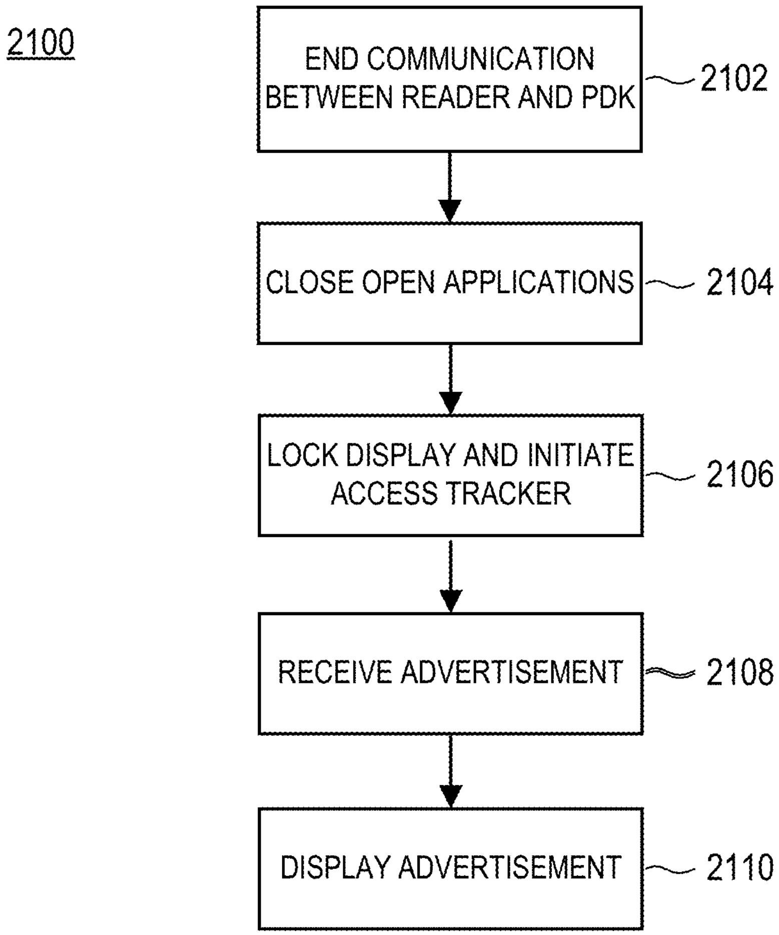
FIG. 21 is a flowchart of a method for locking a computing device coupled to a reader responsive to a PDK exiting the proximity zone of the reader in accordance with the present invention.

FIG. 21 describes one embodiment of a method for locking a computing device 120 using a Reader 620 coupled to the computing device 120 and a PDK 102. In one embodiment, there is no time-out function, i.e., the computing device 120 is not locked or the user logged off after a predetermined amount of time without user input, and the computing device 120 is only locked or the user is logged off responsive to a PDK leaving the proximity zone associated with a Reader 620 of the computing device 120. In one embodiment, responsive to a PDK 120 leaving the proximity zone associated with a Reader 620, the Reader 620 communicates data to the computing device 120 and to the application server 240 to close 2104 applications currently running on the computing device 120. In one such embodiment, the data communicated from the Reader 620 to the application server 240 logs the user associated with the PDK 102 out of the application server 240. By closing 2104 applications executed by the application server 240 and by the computing device 120 when a PDK 102 leaves the proximity zone of the Reader 620, the security of the computing device 120 is increased. In another embodiment, responsive to the PDK 120 leaving the proximity zone, the applications are not closed, but the session is saved and hidden. By not closing the applications when the PDK 102 leaves the proximity zone of the Reader 620, the user can later return to and resume using the computing device 120 without losing any data or state information.

Responsive to data from the Reader 620 indicating the PDK 102 has left the proximity zone of the Reader 620, after closing 2104 open applications, the computing device 120 locks 2106 its display device and initiates an access tracking process. In one embodiment, when the display device 618 is locked 2104, a predefined image is displayed on the display device 618, such as a logo or other image associated with the location where the computing device 120 is located. Alternatively, when the display device 618 is locked 2104, the display device 2104 does not display an image or is a blank screen. The access tracking process is computer-readable data stored in the storage device 608 or the memory 606 of the computing device 120 that, when executed by the processor 602, monitors the keyboard 610, the pointing device 614 or other input/output devices of the computing device 120 for inputs. In one embodiment, the access tracking process unlocks the display device 618 responsive to identifying an input received by an input/output device 120. However, until the access tracking process identifies an input received by an input/output device 120, the display 618 is locked 2104, as further described above. In an alternative embodiment, the access tracking process unlocks the display device 618 responsive to a PDK 102 associated with a user being detected in the proximity zone of the Reader 108.

In one embodiment, the computing device 120 receives 2108 one or more advertisements and displays 2110 the one or more advertisements when the display device 618 is locked rather than displaying a fixed image or blanking the display device 618. For example, the computing device 120 includes one or more advertisements in its storage device 608 and displays 2110 the one or more advertisements when the display device 618 is locked. In one embodiment, the computing device 120 alternates the advertisements displayed 2110 at different time intervals, allowing different advertisements to be displayed 2110 while the display device 618 is locked. In an alternative embodiment, the computing device 120 receives 2108 the one or more advertisements from a third party site 140 or from the application server 240 and displays 2110 one or more of the received advertisements while the display device 618 is locked 2106. In one embodiment, the application server 240 or the third party site 140 receives data from the computing device 120 and modifies the advertisements received 2108 by the computing device 120 responsive to the data received from the computing device 120. For example, the third party site 140 or the application server 240 receives data from the computing device 120 associated with a user or patient whose information has been recently accessed by the computing device 120. The computing device 120 then receives 2108 advertisements from third party site 140 or the application server 240 associated with the user or patient information. This allows the computing device 120 to display 2110 advertisements relevant to the recently accessed user or patient when the display device 618 is locked.

Figure 22:
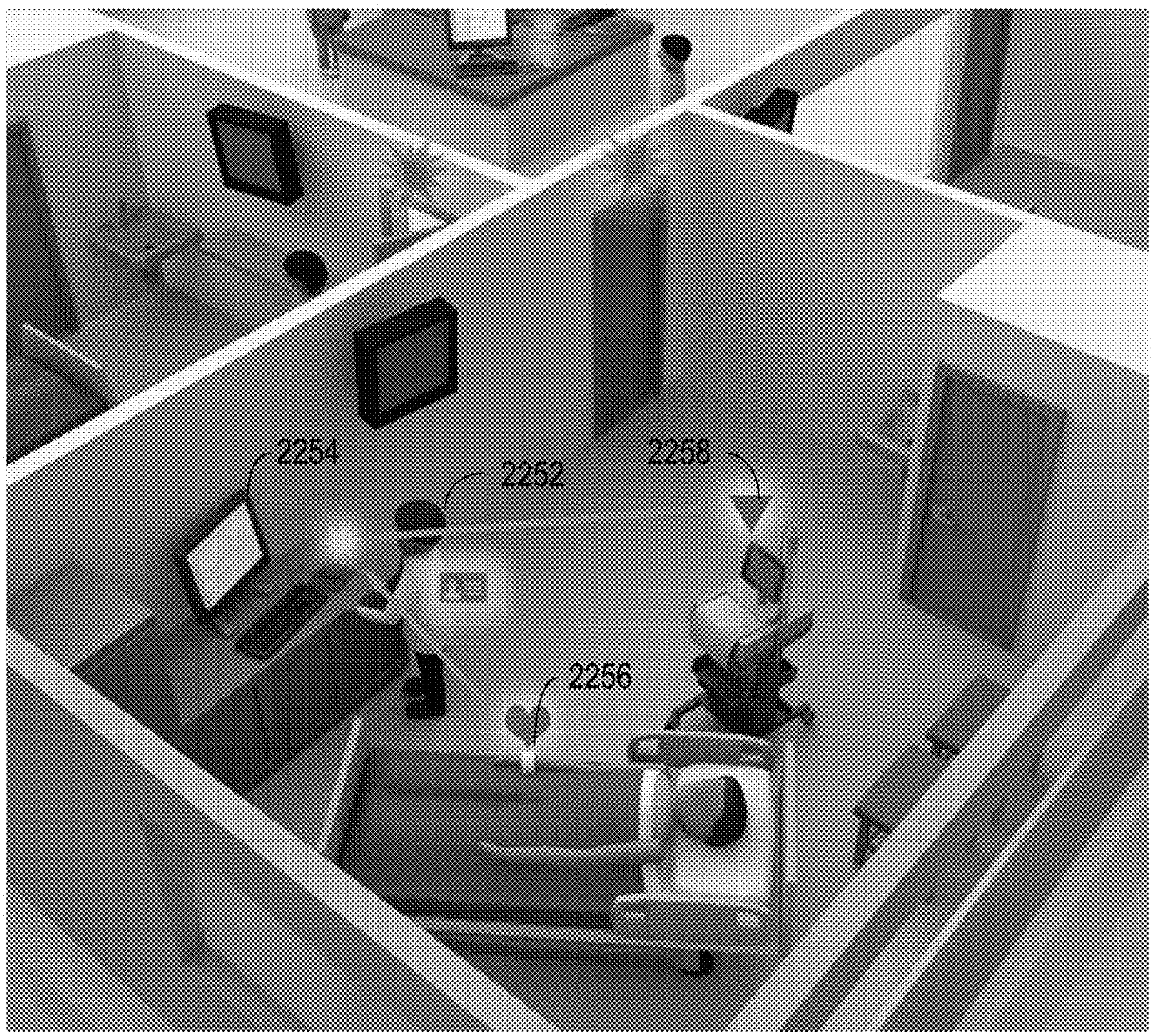
FIG. 22 is a graphical representation of one embodiment of automatic login of users.

FIG. 22 is a graphical representation of one embodiment of automatic login of users. In this illustration, the user is a healthcare provider 2252 with a unique identifying PDK. When the healthcare provider 2252 having its associated PDK enters a patient's room and walks up to a computing device 2254, the reader of the computing device 2154 retrieves information from the provider's 2252 PDK and automatically logs the provider 2252 into the software system.

If PDKs 2256, 2258 are also used to identify the patient and equipment in the patient's room, the reader of the computing device 2254 also retrieves information from those PDKs 2256, 2258. In one embodiment, the computing device displays user names associated with the PDKs 2256, 2258 as well as a user name associated with the healthcare provider 2252 and the healthcare provider 2252 selects the appropriate user name to log in to the computing device. One or more default applications are then launched by the computing device for access by the healthcare provider 2252.

Figure 23:
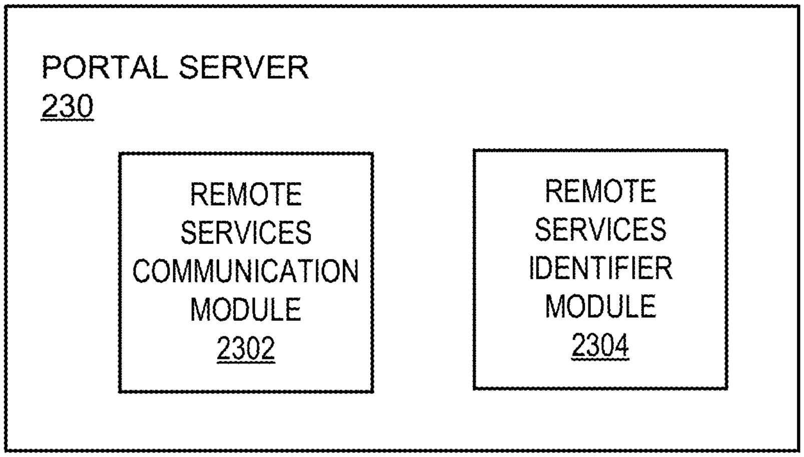
FIG. 23 is a block diagram of a portal server in accordance with the present invention.

FIG. 23 is a block diagram illustrating an embodiment of a portal server 230. The portal 230 provides a consistent interface to the third party site 140. Such services may include receiving advertisement data, accessing a patient's virtual database records or insurance information or sending prescription requests to remote pharmacies. The portal server 230 includes a remote services communication module 2302 and a remote services identifier module 2304.

Figure 24:
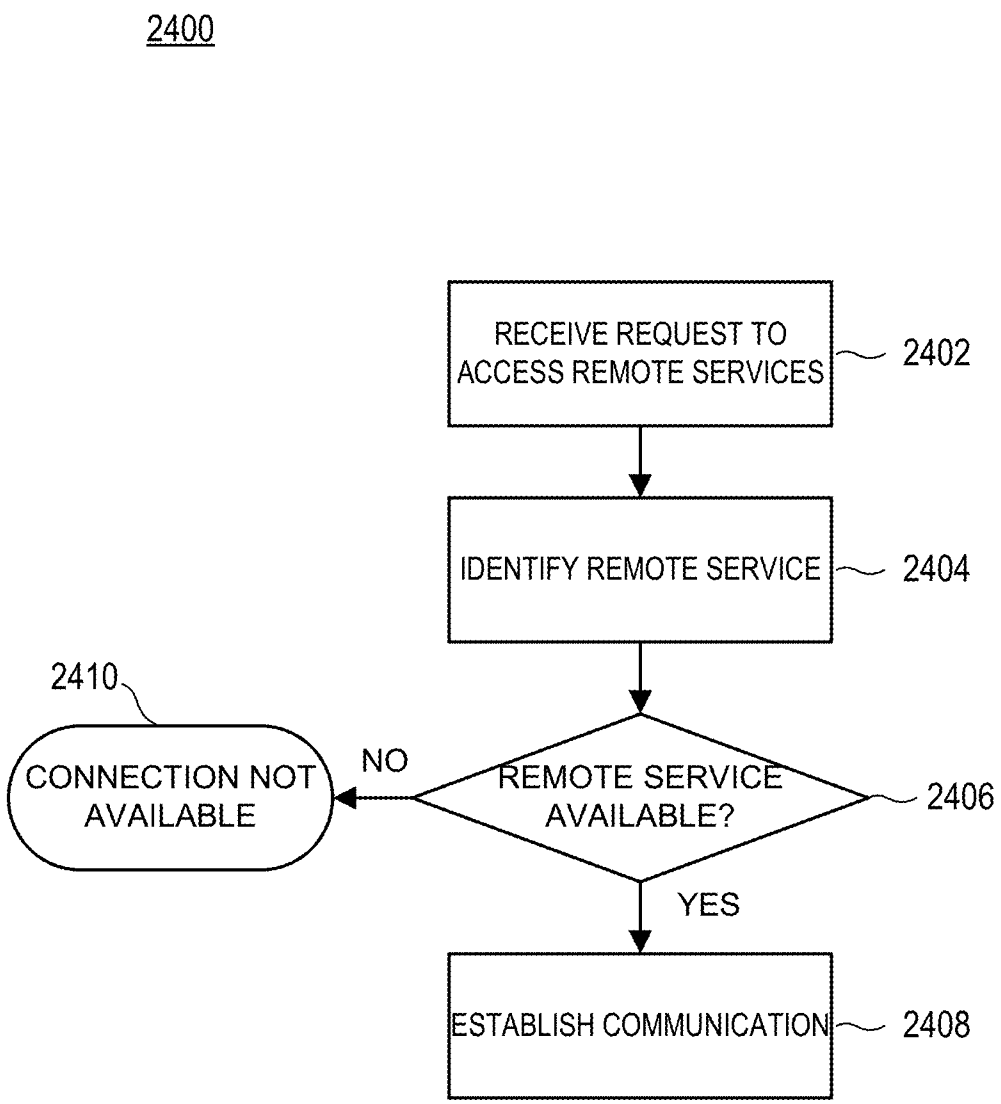
FIG. 24 is a flowchart of a method for communicating with remote services provided by a third party site in accordance with the present invention.

FIG. 24 is a flowchart illustrating one embodiment of a method 2400 for communicating with remote services provided by a third party site 140. The remote services communication module 2302 receives 2402 a request from a computing device 120 to access one or more services, or data, provide by the third party site 140. The remote services identifier module 2304 identifies 2404 which remote service to contact. For example, if the request includes insurance information as well as payment information, the remote services identifier module 2304 determines that the request from the computing device 120 needs to be communicated to a particular third party site 140.

A determination is then made to determine whether the requested remote service or data is available 2406. If the remote service is not available (2406—No), then a connection to the third party site 140 is not established. In some embodiments, an error message is sent to the computing device 120 with a notification of the unavailability of the requested remote service. If the remote service is available (2406—Yes), communication with an appropriate third party site 140 is established.

FIG. 25 is a flow chart of one embodiment of a method 2500 initially storing data on a PDK 102 during an initialization or registration process. In the example of FIG. 25, a PDK 102 is initialized using a computing device 120. Additionally, the initial configuration and data storage of the PDK 102 is witnessed and authenticated by a specialized trusted Notary. In one embodiment, the Notary is associated with a Notary PDK. For example, the computing device 120 includes data identifying PDK IDs associated with one or more notaries.

In one embodiment, the computing device 120 initially identifies 2502 one or more Notaries to witness PDK 102 initialization. For example, a user associated with a master PDK accesses the computing device 120 and identifies one or more PDK identifiers associated with one or more Notaries. Only a user associated with the master PDK 102 is permitted to identify 2102 PDK IDs associated with one or more Notaries. For example, a user associated with a Master PDK 102 identifies one or more PDK IDs associated with Notaries, allowing the computing device 120 to locate Notaries by comparing PDK IDs from a Reader 620 to the Notary PDK IDs identified by the Master PDK.

After a Notary is identified 2502, the computing device 120 establishes 2504 communication with the PDK 102 to be initialized and establishes 2504 communication with a PDK 102 associated with a Notary, as further described above. The computing device 102 receives information from the PDK 102 to be initialized to determine if the PDK 102 to be initialized is authorized for initialization and also receives information from the PDK 102 associated with the Notary to determine if the Notary is authorized to perform the initialization. If both the PDK 102 to be initialized and the PDK 102 associated with the Notary are authorized to perform the initialization, the computing device 120 receives 2508 biometric data from a user associated with the PDK 102 to be initialized. The Notary witnesses the receipt 2508 of biometric data by the computing device 120, either in person or remotely, to ensure that the received biometric data is trustworthy. The computing device 120 then stores 2510 the received biometric data. In one embodiment, the computing device 120 communicates the biometric data to the PDK 102 to be initialized for storage and also locally stores 2510 the biometric data. In another embodiment, the biometric data is stored exclusively on the PDK 102. In yet another embodiment, the computing device 120 communicates the received biometric data to a central registry 114 or a private registry 116 for storage along with the ID of the PDK 102 to be initialized. For example, the central registry 114 or a private registry 116 includes a PDK ID of the PDK 102 to be initialized, biometric data associated with the PDK ID of the PDK 102 to be initialized and other user data associated with the PDK ID of the PDK 102 to be initialized.

Figure 26:
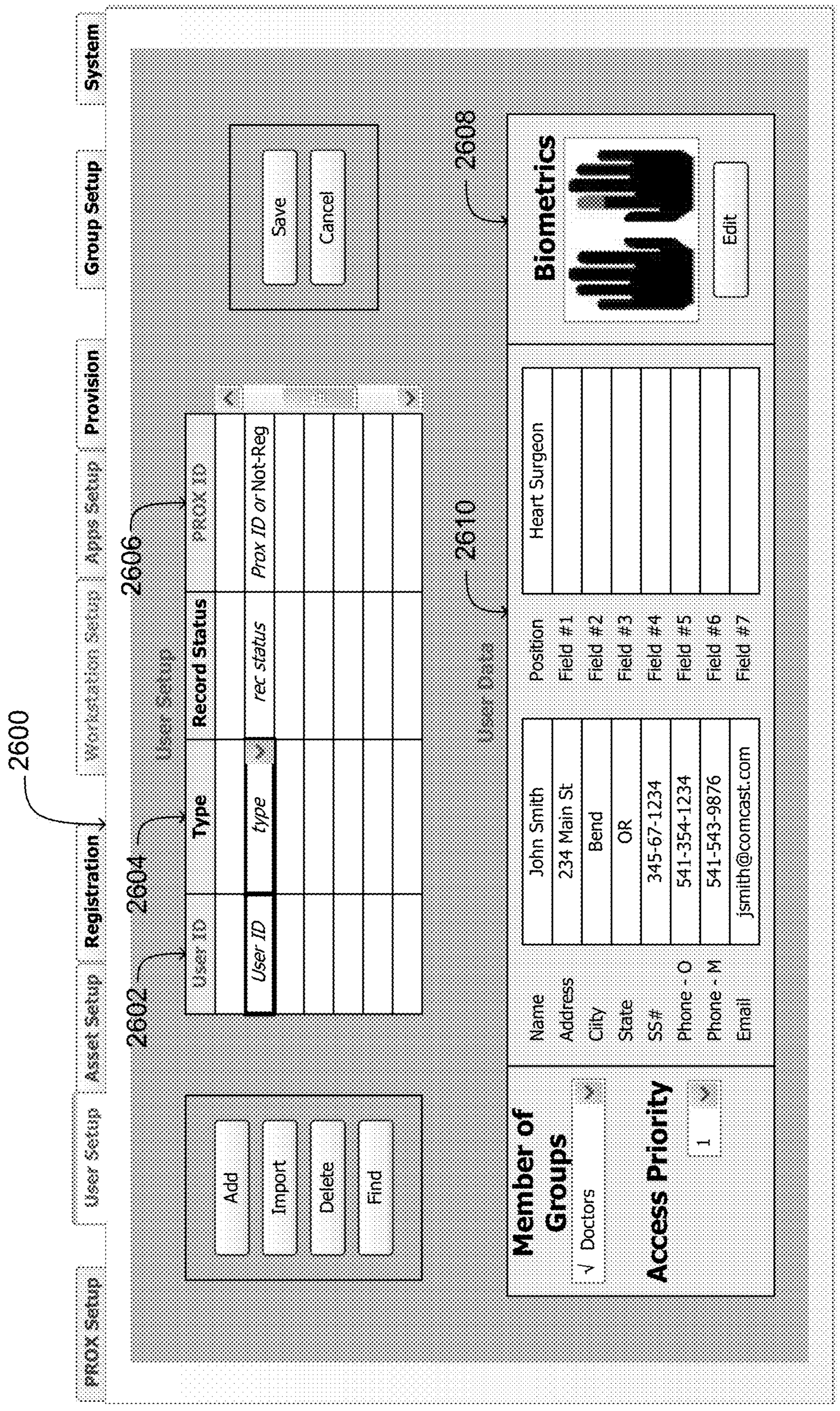
FIG. 26 is an example user interface for configuring user information associated with a PDK in accordance with the present invention.

FIG. 26 shows an example user interface 2600 for configuring user information associated with a PDK 102. In one embodiment, the user interface 2600 is displayed by a computing device 120 that is used to initialize a PDK 102. The user interface 2600 includes a user configuration region having a user identifier editor 2602, a user type editor 2604 and a PDK ID editor 2606. Interacting with the user identifier editor 2602, the user type editor 2604 and the PDK ID editor 2606 allows a user, such as an administrator, to specify a user identifier associated with a PDK ID and to associate a user type with the user name and with the associated PDK ID. In one embodiment, the user type editor 2604 allows a user to select from a predefined listing of user types. For example, the user type editor 2604 allows a user to specify whether a user identifier is associated with a general user, with an administrator or with a Notary. Depending on the user type, the functionality of a user is modified. For example, a user identifier associated with an administrator is able to modify execution of different applications or customize application execution for other users while a user identifier associated with a Notary is authorized to authenticate the accuracy of biometric data received by the computing device 120.

Additionally, the user interface 2600 includes a user data summary 2610 that displays data associated with a user identifier, such as contact information for the user, a job title for the user and a listing of groups to which the user belongs. In one embodiment, a user accesses the user data summary 2610 to identify one or more groups to which the user belongs. Depending upon the embodiment, a user or asset's group(s) can be automatically or manually assigned. In one embodiment, a user or asset's group membership determines one or more of the asset or user's general use processes, typical setup and search processes, default alert conditions, etc. Grouping dramatically simplifies and speeds-up the setup procedure for a user or asset's PDK. In one embodiment, the groups are part of established priority rules and user hierarchies, which can permit or exclude member access to particular workstations or applications. For example, not allowing a billing clerk to login at computing device 120 in an exam room. In one embodiment, a user's group membership determines a default scenario or one or more applications that auto launch. For example, a member of a "nurse" group and a member of a "doctor" group may have a different application auto launch. In one embodiment, one or more application-specific preferences are assigned based on group membership. For example, a "pharmacist" group member may automatically be taken to a current medications section of a patient's medical record, while a "nurse" group member may be automatically taken to a section to enter the patient's current vital signs. A biometric data summary 2608 is also displayed to identify the type of biometric data associated with a user and allowing a Notary to modify the biometric data by interacting with the biometric data summary. For example, a Notary may access the biometric data summary 2608 to obtain a different type of biometric data associated with the user.

Figure 27:
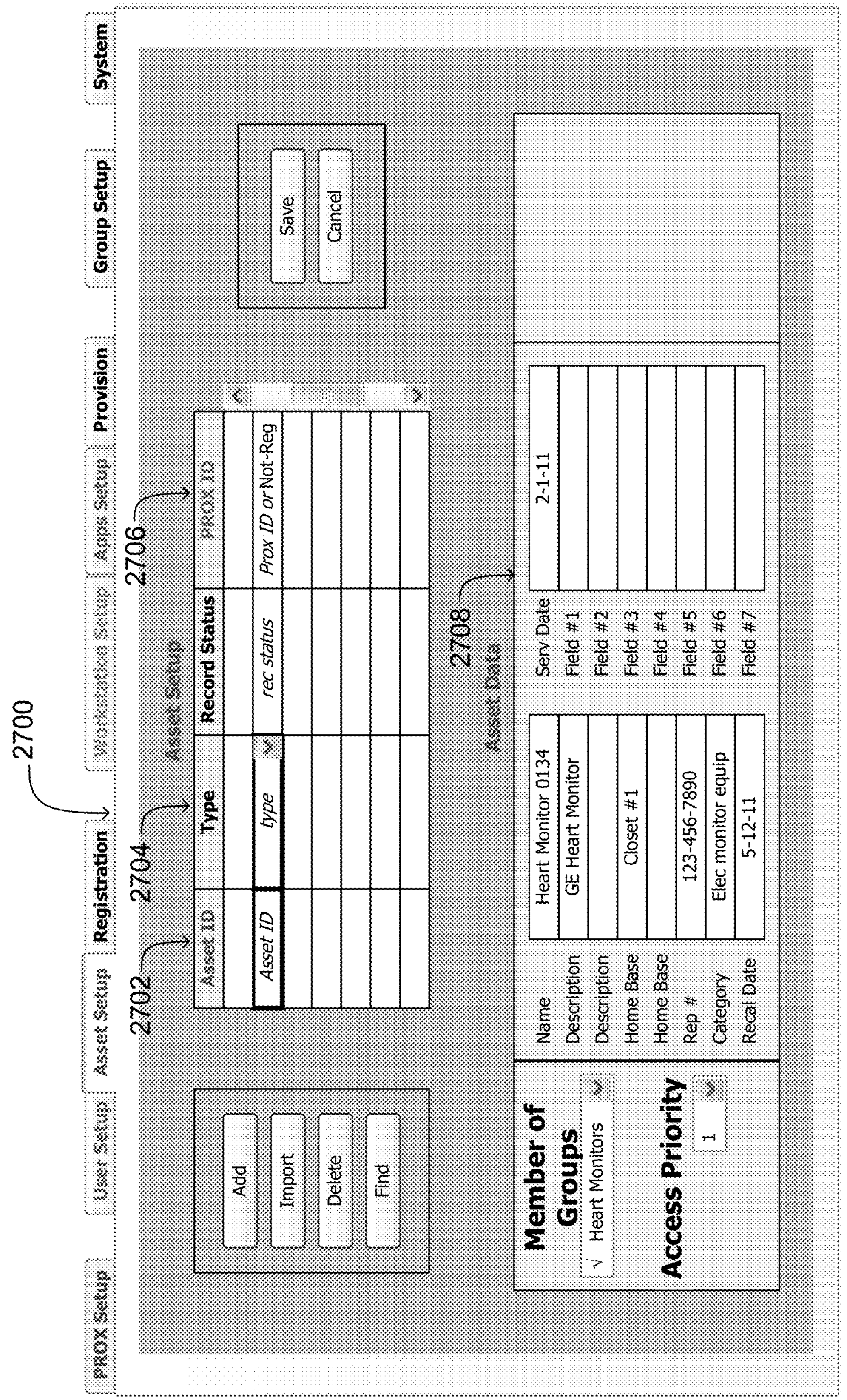
FIG. 27 is an example user interface for configuring asset information associated with a PDK in accordance with the present invention.

FIG. 27 shows an example user interface 2700 for configuring asset information associated with a PDK 102. While FIG. 26 describes configuration of a user, such as an individual, associated with a PDK 102, FIG. 27 describes configuration of information associated with an asset, such as equipment or supplies, associated with a PDK 102. In one embodiment, the user interface 2700 is displayed by a computing device 120 that is used to initialize a PDK 102. The user interface 2700 includes an asset configuration region having an asset identifier editor 2702, an asset type editor 2704 and a PDK ID editor 2706. Interacting with the asset identifier editor 2702, the asset type editor 2704 and the PDK ID editor 2706 allows a user, such as an administrator, to specify a user identifier associated with a PDK ID and to associate a user type with the user name and with the associated PDK ID. In one embodiment, the asset type editor 2704 allows a user to select from a predefined listing of asset types. For example, the asset type editor 2704 allows a user to specify whether an asset identifier is associated with a general asset, with an administrator or with a Notary. Depending on the asset type, the functionality of an asset is modified, as described above in conjunction with FIG. 26.

Additionally, the user interface 2700 includes an asset data summary 2708 that displays data associated with an asset identifier, such as an asset name, an asset description, an asset location, an asset category, an asset service data or other data describing attributes of the asset. In one embodiment, a user accesses the asset data summary 2708 to identify one or more groups to which the asset belongs.

Figure 28:
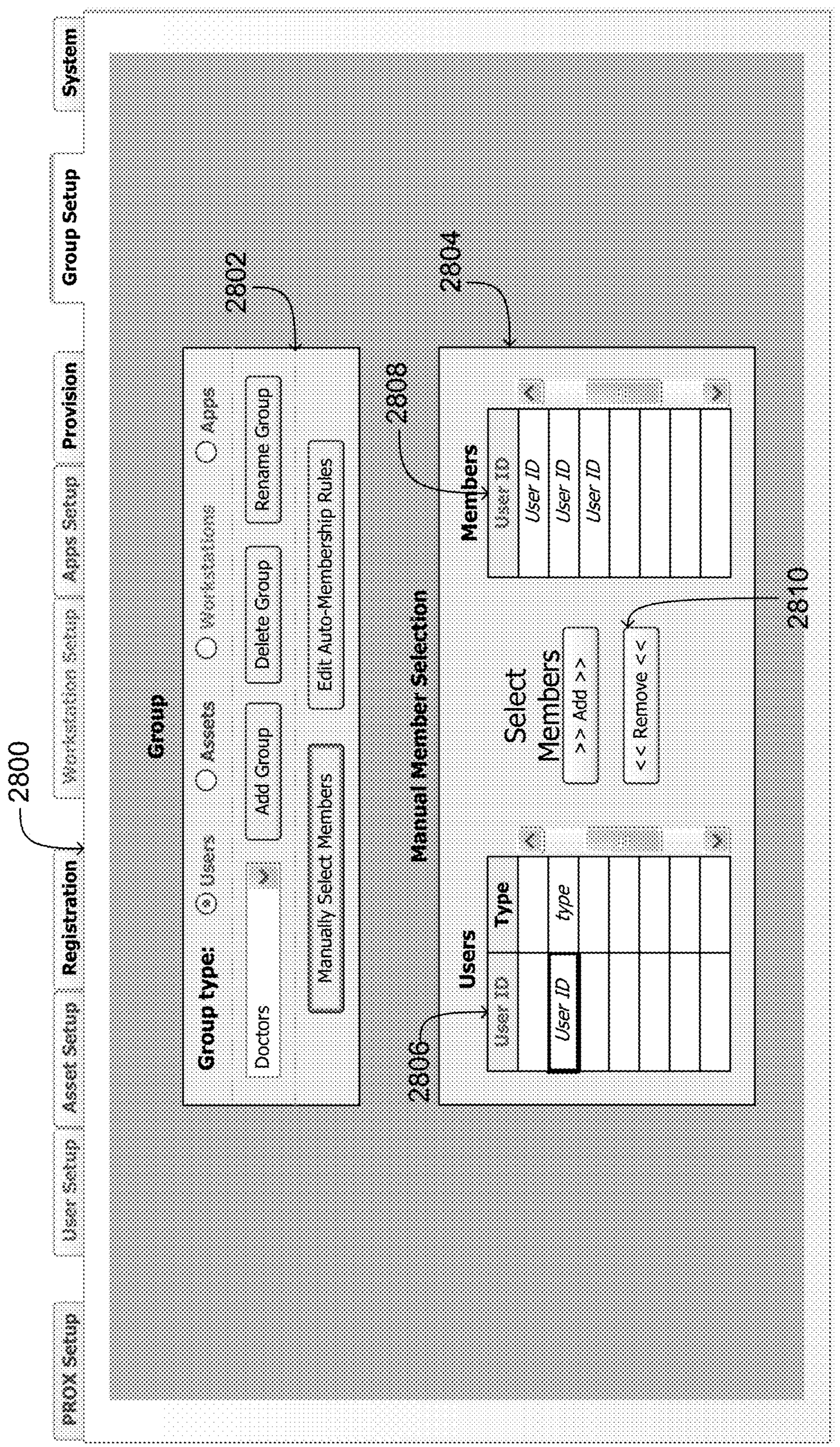
FIG. 28 is an example user interface for manually identifying assets or users included in a group in accordance with the present invention.

In addition to interacting with a user data summary 2610 or an asset data summary 2708 to associate users or assets with a group, one or more user interfaces may be used to automatically or manually associate user identifiers or asset identifiers with one or more groups. FIG. 28 illustrates an example user interface 2800 allowing a user to manually identify members, such as users and/or assets, included in a group. The user interface 2800 includes a group description 2802 allowing a user to identify a group type, specify a group name and to modify the group name or group type.

A member selection region 2804 identifies users and/or assets included in a central registry 114 and/or a private registry 116 using a user listing 2806 and identifies users and/or assets included in the group identified by the group description 2802 using a member listing 2808. In one embodiment, a user selects a user identifier, or an asset identifier, from the user listing 2806 and accesses a group modification region 2810, causing the selected user identifier or asset identifier to be included in the group identified by the group description 2802. Once the group modification region 2810 is accessed, the selected group identifier, or asset identifier, is displayed in the member listing 2808 rather than in the user listing 2806. Similarly, a user selects a user identifier, or an asset identifier, from the member listing 2808 and accesses a group modification region 2810 to remove the selected user identifier, or asset identifier, from the group identified by the group description 2802.

Figure 29:
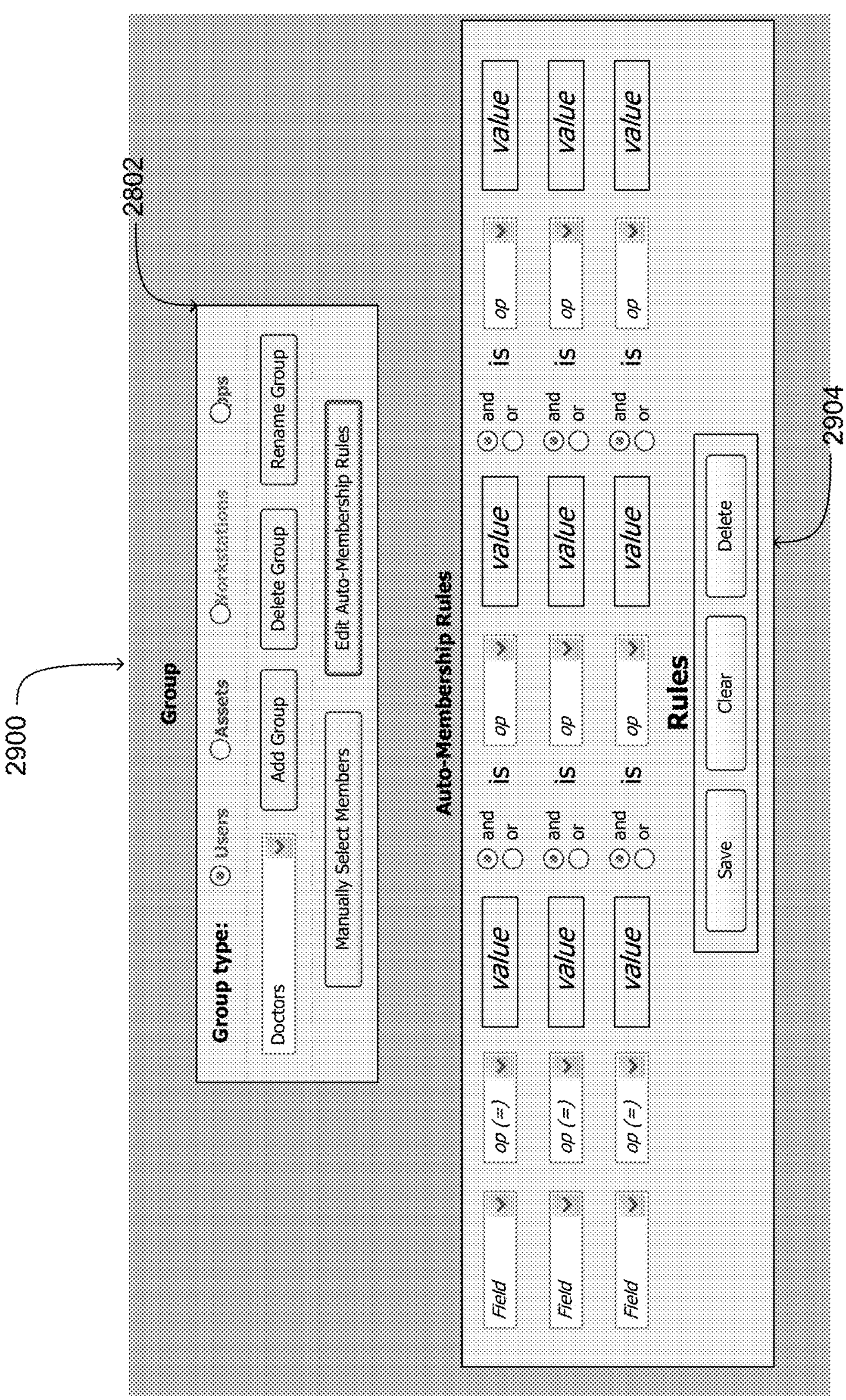
FIG. 29 is an example user interface for automatically identifying assets or users included in a group in accordance with the present invention.

FIG. 29 illustrates an example user interface 2900 allowing a user to automatically include users and/or assets in a group based on one or more criteria. The user interface 2900 includes a group description 2802 allowing a user to identify a group type, specify a group name and to modify the group name or group type.

A rule specification region 2904 receives input identifying one or more rules for identifying users and/or assets for inclusion in a group. For example, the rule specification region 2904 receives rules for including a user or asset in the group identified by the group description 2802. In one embodiment, the rule specification region 2904 receives input identifying values for one or more fields associated with a user, or an asset, and a user or asset including fields matching the values identified by the rules is automatically associated with the group identified in the group description 2802. In the example shown by FIG. 29, the rule specification region 2904 allows a user to specify combinations of fields and values associated with the fields to customize the users or assets included in the group. For example, a rule may include logical operators, such as "AND" or "OR," to describe combinations of values and/or fields.

Figure 30:
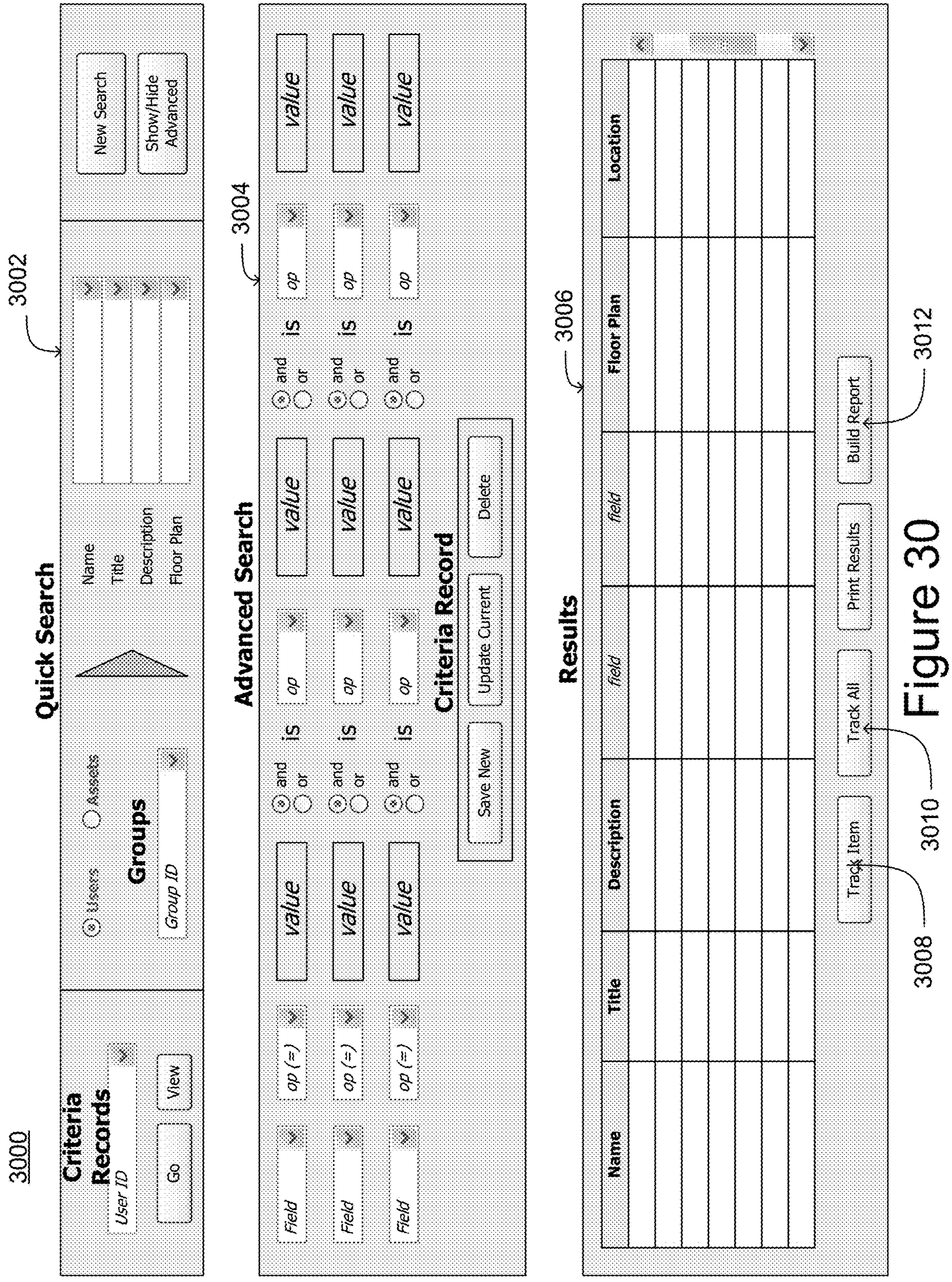
FIG. 30 is an example user interface for tracking a user or an asset associated with a PDK in accordance with the present invention.

FIG. 30 is an example of a user interface 3000 for tracking a user or asset associated with a PDK 102 from a computing device 120. The user interface 3000 receives input from a user to identify a user or asset to be tracked by the tracking server 210. In the example of FIG. 30, the user interface 3000 includes a quick search interface 3002 and an advanced search interface 3004 as well as a result listing 3006.

A person having ordinary skill will recognize that the search options for the quick search 3002 and advanced search 3004 interfaces can range from pre-defined named criteria selection, to common filters related to the tracked item type, to detailed multi-level equation-based tracked item value field specifications.

The quick search interface 3002 receives input from a user for performing simple searches based on a limited amount of data associated with a user or an asset. For example, the quick search interface 3002 receives input identifying a name, a title, a description or a location of a user or an asset and identifies the user or asset matching the received input. The quick search interface 3002 also allows specification of a group identifier to retrieve assets or users included in the specified group.

The advanced search interface 3004 receives input for performing advanced searches based on multiple data associated with a user or an asset or based on combinations of data associated with a user or an asset. In one embodiment, the advanced search interface 3004 receives input identifying values for one or more fields associated with a user or an asset that are used to identify one or more users or assets including fields having values matching those identified by the values, or combination of values, received by the advanced search interface 3004. In the example shown by FIG. 30, the advanced search interface 3004 allows a user to specify combinations of fields and values associated with the fields to identify assets or values. For example, the advanced search interface 2004 receives input identifying values for multiple fields and logical operators describing a number of values for different fields. For example, the advanced search interface 3004 allows values for fields to be combined using logical operators, such as "AND" or "OR," to describe combinations of values and/or fields.

The result listing 3006 displays data associated with users or assets that match the search criteria received by the quick search interface 3002 or the advanced search interface 3004. In one embodiment, the results listing 3006 dynamic, i.e., the results are dynamically modified and displayed as a user inputs or modifies search criteria enabling the user to review and accept or continue entry of criteria. For example, in such an embodiment, if the user is searching for a heart monitor on a specific floor of a hospital, the user inputs or selects "heart monitor" in a name or description field causing all heart monitors in the system to be displayed in the results listing 3006. The user then scrolls through the floor plan options in a floor plan drop-down menu. As the user mouses-over each floor plan the heart rate monitors located on the moused-over floor plan are automatically displayed in the result listing 3006 without the user selecting the floor plan. For example, the result listing 3006 displays a name, a title, a description, a floor plan and a location associated with different assets or users matching the search criteria. In one embodiment, the result listing 3006 receives input selecting one or more of the search results and a tracking input 3008 causes the tracking server 210 to monitor the location of the assets or users selected via the result listing 3006. In one embodiment, a first input received by the tracking input 3008 causes the tracking server 210 to track the selected assets or users while a second input received by the tracking input 3010 causes the tracking server 210 to track each of the assets or users identified by the result listing 3006. In one embodiment, a third input 3012 causes the tracking server to generate a report and a fourth input (not shown) causes the tracking server to generate an alarm regarding one or more of the users or assets in the result listing 3006. The search results and/or subsequent locations, tracking, or reports can be displayed in any number of forms including, but not limited to textually, graphically or in time and motion study reports. Types of reports other than motion reports may be generated, for example, an audit report may be generated in order to monitor and document one or more of the usage, maintenance and calibration of equipment. Such reports may subsequently be used by a user or by the tracking server to schedule one or more of future maintenance and future calibration when a piece of equipment is not typically in use or when an alternative piece of equipment is typically available.

In some embodiments, the user interface may be used to audit multiple items in a geographic area, sort the items based on one or more criteria and cause the items that meet a condition to produce an audio and/or visual indication. For example, in one embodiment, the floor plan section of 3002 is used to select a geographic area. The results are displayed in the result listing 3006 where the results may be sorted and displayed based on a field including calibration dates or usage metrics. The items that are out of calibration or due for servicing based on usage metrics are sent a signal that causes the items to create a visual and/or audible alert. Depending on the embodiments, the signal may be automatic (e.g., as part of an alert condition) or manual (e.g., sent based on user input from a user auditing the maintenance of the items). In some embodiments, the items that are out of calibration are sent a signal that causes the items to create a visual and/or audible alert (e.g., flashing and/or beeping) when the item is proximate to one or more similar items.

Figure 31:
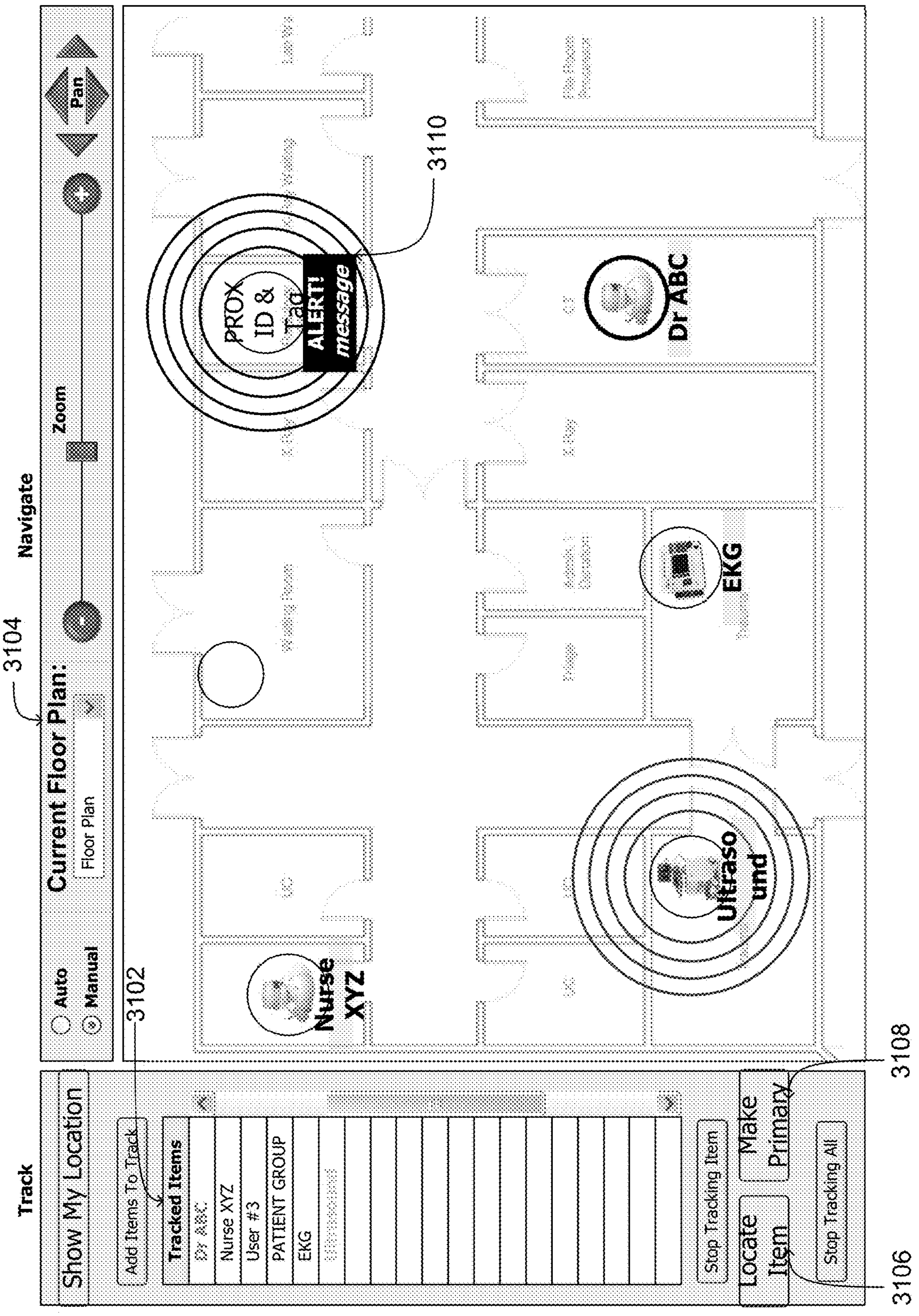
FIG. 31 is an example user interface for identifying the location of a tracked user or asset associated with a PDK in accordance with the present invention.

FIG. 31 is an example of a user interface 3100 for identifying the location of a tracked user or asset associated with a PDK 102 from a computing device 120. The user interface 3100 displays data from the tracking server 210 indicating the location of one or more assets or users tracked by the tracking server 210. In the example of FIG. 30, the user interface 3100 includes a tracked item listing 3102, a navigation interface 3104, an item location selector 3106 and a primary item selector 3108.

The tracked item listing 3102 displays an item identifier associated with users or assets tracked by the tracking server 210. For example, the tracked item listing 3102 displays a user name or asset name associated with the tracked items. The tracked items list 3102 can include selected items from a single or most recent search result or can accumulate items from a plurality of search results. In one embodiment, the tracked item listing 3102 receives input selecting a user or asset and a subsequent input received by the item location selector 3106 or the primary item selector 3108 modifies the user interface 310. Items included in the tracked item listing 3102 may be manually identified by user input or may be automatically included based on one or more criteria of a user or an asset.

After selecting a user or asset from the tracked item listing 3102, an input received by the item location selector 3106 causes the user interface 3100 to visually distinguish the location of the selected item in the navigation interface 3104. For example, the navigation interface 3104 visually distinguishes the selected item from other tracked items responsive to the item location selector 3106 thus making the item easier to find on a crowded display. In the example of FIG. 31, the navigation interface 3104 modifies the color used to display the selected item and displays rings around the selected item responsive to the item location selector 3106 receiving an input. In one embodiment, tracking is in or near real-time or periodically updated (e.g., every few minutes). In one embodiment, historic tracking is possible, i.e., showing the item's change in location and time intervals of location change or being able to playback the items route over a time interval. In one embodiment, the historic tracking is utilized for time and motion reports and/or study, which includes one or more textual reports for any combination of tracked items and site map tracking zones and time periods including relative time periods (e.g., yesterday, last night, etc.) showing various formats of tracking time and location data. In one embodiment, the historic tracking data capable of being output for external playback or recording.

In some embodiments, the system 100 enables the item(s) on the tracked item listing 3102 to produce one or more of a visual and audio alert at the item(s). For example, assume an item is required for a procedure and is placed on a track items list 3102, in one embodiment, one or more of a visual device and an audio device are either integrated into the PDK 102 or connected (e.g. via the programmer I/O 340) to the PDK 102. In one such embodiment, the item(s) may provide visual or audio instructions to move the equipment to the location of the procedure. Such embodiments may beneficially expedite the process of locating and/or collecting items.

After selecting a user or asset from the tracked item listing 3102, an input received by the primary item selector 3108 causes the user interface 3100 to make the selected item the primary item so that the navigation interface 3104 is modified to keep the selected item visible. For example, the navigation interface 3104 scrolls as the primary item moves (even between floor plans) to keep the primary item visible in the navigation interface 3104. Additionally, the navigation interface 3104 may visually differentiate the primary item from other tracked items by changing the color used to display the primary item or otherwise modifying the presentation of the primary item relative to other tracked items. In one embodiment, other items near the primary item are displayed. This may be important for reducing response times. For example, a heart monitor detects heart failure and alert is sent to the nearest provider. In one embodiment, the user may select a tracked item using a pointing device 614 to display information regarding the item, e.g., the item's ID, tracking data, reference data, calibration and service history, etc.

In some embodiments, selecting an item as the primary item causes one or more of a visual and audio alert at the item itself. For example, assume an item has been selected as a primary item, in one embodiment, one or more of a visual device and an audio device are either integrated into the PDK 102 or connected (e.g. via the programmer I/O 340) to the PDK 102. In one such embodiment, the item will begin to audibly beep or visually flash. In another such embodiment, the item begins to audibly beep and/or flash when the item is in proximity to other similar items. Such embodiments may beneficially expedite the process of locating the primary item. For example, it may be easier to locate and/or track wandering Alzheimer's patient (i.e., an example of a primary item) in a crowded area if the PDK 102 associated with the patient is beeping.

The navigation interface 3104 displays the location of the items identified in the tracked item listing 3102 in a graphical representation of the environment including the tracked items. For example, the navigation interface 3104 displays a floor plan of an environment including the tracked items with the location of the tracked items overlaid on the floor plan. In one embodiment, the navigation interface 3104 includes navigation controls allowing a user to zoom in or out of the graphical representation of the environment including the tracked items or to pan across the graphical representation of the environment including the tracked items. In one embodiment, the navigation interface 3104 displays the current location (not shown) of the user and/or the computing device 120 the user is using to track the items from in addition to the one or more items the user desires to track. In one such embodiment, the navigation interface 3104 includes an auto navigate function which will automatically pan or zoom to the user's location or the tracked item's location. In one embodiment, the navigation interface 3104 will also display a route the user can take to reach the tracked item. The navigation interface 3104 may also include a selector allowing modification of the graphical representation of the environment including the tracked items. For example, the navigation interface 3104 allows modification of the floor plan on which the positions of the tracked items are overlaid.

In one embodiment, the navigation interface 3104 also displays one or more alert notifications 3110 associated with tracked items. An alert notification 3110 is displayed responsive to a tracked item meeting one or more criteria. The one or more criteria can include a particular PDK 102 or event being detected (e.g., psychiatric patient leaves the psychiatric ward or enters a restricted zone, a minimum or maximum number of qualified PDKs entering or leaving a zone, or paired PDKs 102 being separated) or not being detected (e.g., a doctor not making rounds) including sudden or unexpected detection or loss of detection (e.g., loss of signal without low battery warning), which may indicate PDK 102 or system malfunction (e.g., a broken PDK) or tampering (e.g., a person hiding the signal by covering the PDK with metal or otherwise disabling the device, one or more sensor readings (e.g., temperature proximate to an asset enters or exits a user specified range or a low battery is detected) or at a predetermined time (e.g., when an asset must be serviced, calibrated or decommissioned). The alert notification 3110 visually differentiates the item meeting the criteria from other tracked items. In one embodiment, the alert notification 3110 displays a text message describing the alert. In one embodiment, one or more alerts may be temporarily disabled for a brief period of time by selecting a "reset in process" status. In one embodiment, one or more of the type of alert, frequency of alert, response time to alert and user responding to an alert are logged and available for review and analysis. A user interface, such as the one described below in conjunction with FIG. 32, allows customization of the criteria that cause display of an alert notification 3110.

In some embodiments, an alert causes one or more of a visual and audio alert at the item itself. For example, assume an item has met alert criteria, in one embodiment, one or more of a visual device and an audio device are either integrated into the PDK 102 or connected (e.g. via the programmer I/O 340) to the PDK 102. In one such embodiment, the item (e.g., a piece of equipment) begins to audibly beep and/or flash its display when alert criteria are met (e.g., the equipment is due to be recalibrated). In another such embodiment, the item begins to audibly beep and/or flash when the item is in proximity to other similar items. Such embodiments may beneficially expedite the process of locating the item associated with the alert. For example, it may be easier to locate the equipment that needs recalibration in a closet full of similar equipment if the equipment flashes and beeps when it needs recalibration. For another example, it may be easier to identify the patient who is due to receive his/her medication if the patient is beeping.

Figure 32:
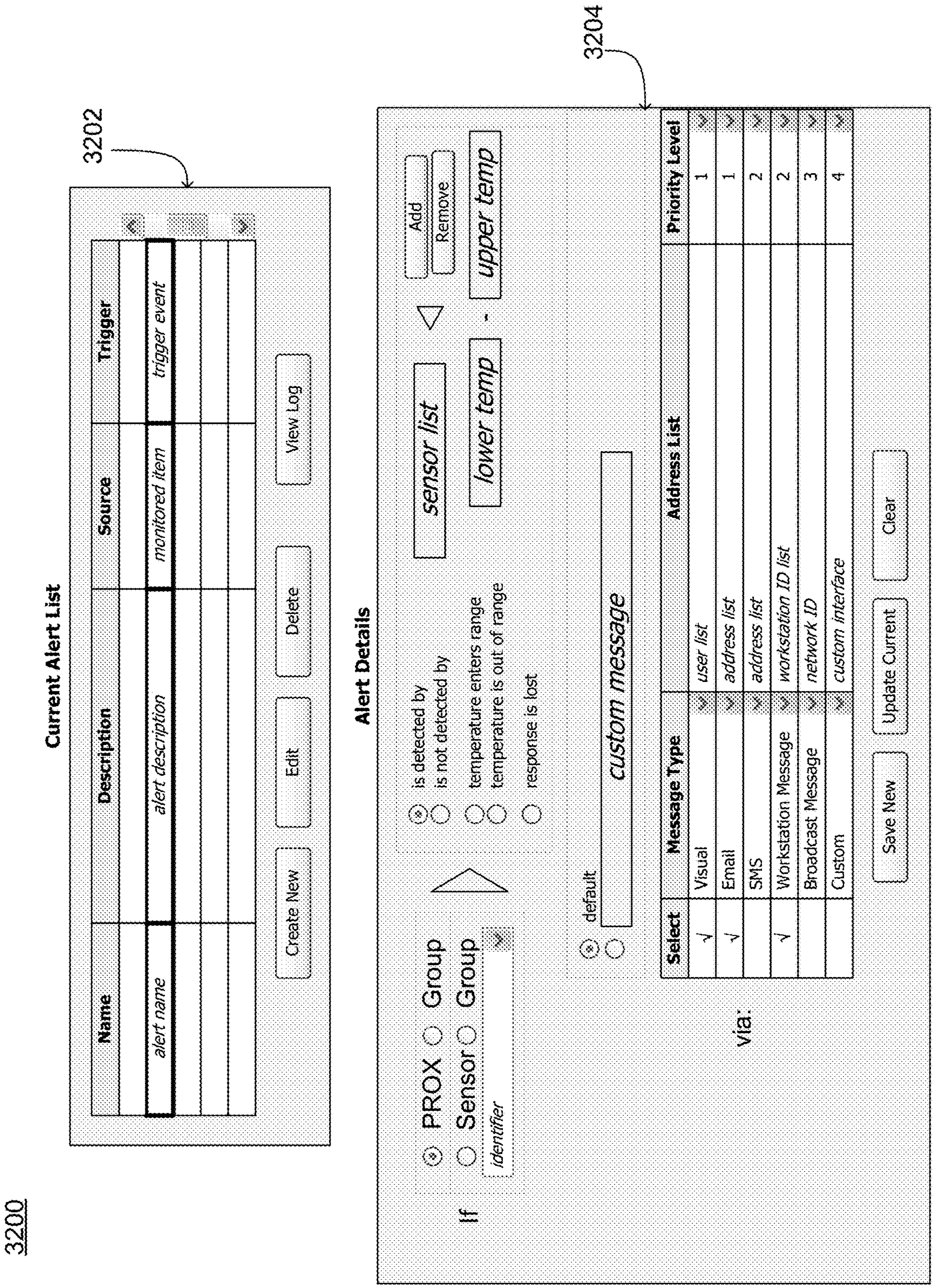
FIG. 32 is an example user interface for describing an alert for a tracked user or asset in accordance with the present invention.

FIG. 32 is an example of a user interface 3200 for specifying generation of an alert for an asset or user tracked by the tracking server 210. The user interface 3200 includes a current alert listing 3202 and an alert editor 3204. In one embodiment, data received by the user interface 3200 is communicated to the alert server 250, which generates alerts responsive to the received data. The current alert listing 3202 identifies alerts which are applied by the alert server 250 to data received from the tracking server 210 and/or from one or more PDKs 102. For example, the current alert listing 3202 displays an alert identifier and a description of the alerts currently being monitored by the alert server 250. The alerts in the current alert listing 3202 may be monitored simultaneously, randomly or in a preconfigured priority order. The current alert listing 3202 also receives input stopping the alert server 250 from applying an alert to received data. Also, the current alert listing 3202 receives input for creating a new alert for application by the alert server 250.

The alert editor 3204 receives input for specifying a new alert or for modifying attributes of an existing alert. For example, the alert editor 3204 receives data identifying the source of data for which the alert server 250 applies the alert, such as from the tracking server 210, from a PDK 102 or from a Reader 108 or other sensor. The alert editor 3204 also receives data specifying the criteria causing an alert to be generated. For example, the alert editor 3204 receives data specifying a temperature range so that an alert is generated when the alert server 250 receives data from a source indicating the temperature is within the specified range.

The alert editor 3204 also receives data specifying how the alert server 250 notifies a user that an alert is generated. In one embodiment, the alert editor 3204 receives data identifying one or more communication protocols and contact information used to communicate an alert notification to a user. For example, the alert editor 3204 receives a user telephone number and e-mail address associated with a user, allowing the user to receive notification of an alert via a telephone call, a text message and/or an e-mail. In one embodiment, the alert editor 3204 associates a priority level to be associated with different communication protocols to allow a user to specify how the user is notified when an alert is generated. For example, the alert editor 3204 associates a first communication protocol with a first priority level and if the tracking server 210 does not receive a response within a specified time interval after notifying a user of an alert, a second communication protocol having a second priority level is used to again notify the user of the alert.

Figure 33:
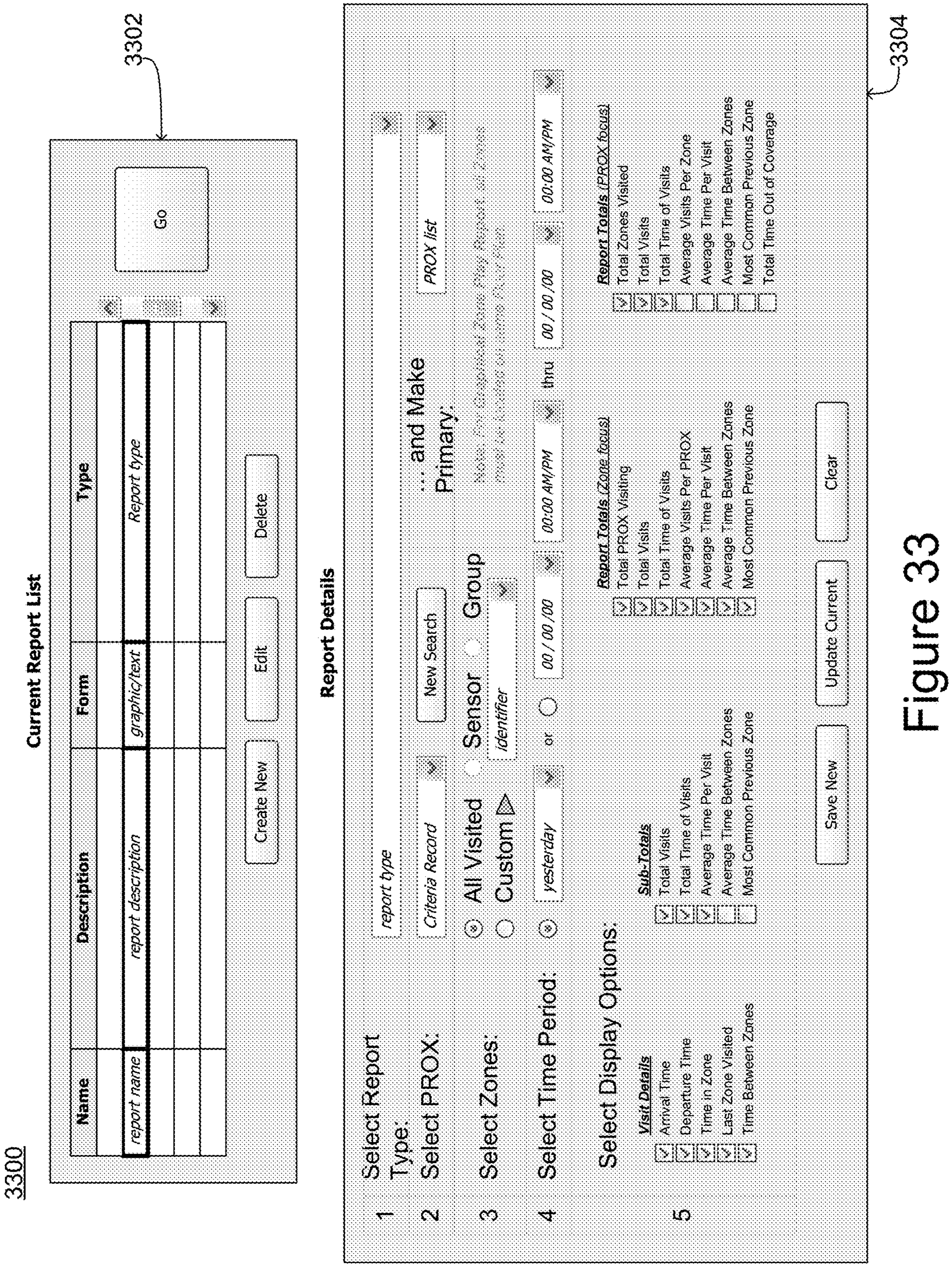
FIG. 33 is an example user interface for describing a report for a tracked user or asset in accordance with the present invention.

FIG. 33 is an example of a user interface 3300 for describing reports generated by data received from the tracking server 210 describing movement of assets or users. The user interface 3300 includes a current report listing 3302 and a report editor 3304. The current report listing 3302 identifies reports which are generated by the tracking server 210 based on data received from PDKs 102 or other sources. For example, the current report listing 3302 displays a report identifier and a description of the reports being generated by the tracking server 210. The current report listing 3302 also receives input stopping the generation of a report by the tracking server 210 from received data. Also, the current report listing 3302 receives input for creating a new report for generation by the tracking server 210 or for editing a report generated by the tracking server 210.

The report editor 3304 receives input for specifying a new report for generation or for modifying a currently generated report. For example, the report editor 3304 receives data identifying a type of report, a PDK 102 from which data for the report is received, one or more locations from which data included in the report is received, a time interval associated with the report and a description of data included in the generated report. For example, the report editor 3304 receives data indicating that the report includes the number of PDKs 102 visiting a location, the total number of locations visited by a PDK 102, the length of time a PDK 102 was in a location or other suitable data. In one embodiment, the report editor 3304 also receives data describing how the content included in the report is presented.

The foregoing description of the embodiments of the present embodiment of invention has been presented for the purposes of illustration and description. It is not intended to be exhaustive or to limit the present embodiment of invention to the precise form disclosed. Many modifications and variations are possible in light of the above teaching. It is intended that the scope of the present embodiment of invention be limited not by this detailed description, but rather by the claims of this application. As will be understood by those familiar with the art, the present embodiment of invention may be embodied in other specific forms without departing from the spirit or essential characteristics thereof. Likewise, the particular naming and division of the modules, routines, features, attributes, methodologies and other aspects are not mandatory or significant, and the mechanisms that implement the present embodiment of invention or its features may have different names, divisions and/or formats. Furthermore, as will be apparent to one of ordinary skill in the relevant art, the modules, routines, features, attributes, methodologies and other aspects of the present embodiment of invention can be implemented as software, hardware, firmware or any combination of the three. Also, wherever a component, an example of which is a module, of the present embodiment of invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present embodiment of invention is in no way limited to implementation in any specific programming language, or for any specific operating system or environment. Accordingly, the disclosure of the present embodiment of invention is intended to be illustrative, but not limiting, of the scope of the present embodiment of invention, which is set forth in the following claims.

What is claimed is:

1. A method comprising:

detecting a first device coupled to a first asset within a proximity zone of a reader device;

wirelessly receiving, at a first rate of response, logged data from the first device coupled to the first asset within the proximity zone of the reader device;

detecting a movement of the first asset within the proximity zone of the reader device;

responsive to detecting the movement of the first asset within the proximity zone of the reader device, wirelessly receiving, at a second rate of response, the logged data from the first device coupled to the first asset;

determining whether the logged data received at one of the first rate of response or the second rate of response from the first device coupled to the first asset satisfies a criterion; and responsive to determining that the logged data received at one of the first rate of response or the second rate of response from the first device coupled to the first asset satisfies the criterion, triggering an alert signal to be automatically generated at the first device coupled to the first asset, wherein the alert signal further causes the first device to emit an audio/visual response.

2. The method of claim 1, wherein wirelessly receiving the logged data from the first device coupled to the first asset at the second rate of response indicates a detection of movement of the first asset.

3. The method of claim 1, further comprising:

tracking a change in location of the first asset based on the second rate of response; and determining a route of the first asset over an interval of time responsive to tracking the change in location of the first asset.

4. The method of claim 1, further comprising:

wirelessly receiving, at the first rate of response, logged data from the first device coupled to the first asset within the proximity zone of the reader device, the first rate of response being at a reduced rate compared to the second rate of response.

5. The method of claim 4, wherein wirelessly receiving the logged data from the first device coupled to the first asset at the first rate of response indicates an idle state of the first asset.

6. The method of claim 1, further comprising:

detecting a second device coupled to a second asset proximate to the first device coupled to the first asset; and responsive to determining that the logged data from the first device coupled to the first asset satisfies the criterion and detecting the second device coupled to the second asset proximate to the first device coupled to the first asset, triggering an alert signal to be automatically generated at the second device coupled to the second asset, wherein the alert signal further causes the second device to emit an audio/visual response.

7. The method of claim 6, wherein the first asset includes a healthcare equipment and the second asset includes a healthcare provider.

8. The method of claim 1, wherein the audio/visual response includes an instruction to move the first asset to a specific location.

9. The method of claim 1, wherein the logged data includes an activity associated with the first asset.

10. The method of claim 9, wherein the activity associated with the first asset includes usage, maintenance, and calibration of the first asset.

11. The method of claim 1, wherein the criterion includes a sensor reading of the first asset in the logged data matching a predetermined range.

12. A system comprising:

a processor; and a memory including instructions that, when executed by the processor, causes the system to:

detect a first device coupled to a first asset within a proximity zone of a reader device;

wirelessly receive, at a first rate of response, logged data from the first device coupled to the first asset within the proximity zone of the reader device;

detect a movement of the first asset within the proximity zone of the reader device;

responsive to detecting the movement of the first asset within the proximity zone of the reader device, wirelessly receive, at a second rate of response, the logged data from the first device coupled to the first asset;

determine whether the logged data received at one of the first rate of response or the second rate of response from the first device coupled to the first asset satisfies a criterion; and responsive to determining that the logged data received at one of the first rate of response or the second rate of response from the first device coupled to the first asset satisfies the criterion, trigger an alert signal to be automatically generated at the first device coupled to the first asset, wherein the alert signal further causes the first device to emit an audio/visual response.

13. The system of claim 12, wherein the logged data wirelessly received from the first device coupled to the first asset at the second rate of response indicates a detection of movement of the first asset.

14. The system of claim 12, wherein the instructions further cause the system to:

track a change in location of the first asset based on the second rate of response; and determine a route of the first asset over an interval of time responsive to tracking the change in location of the first asset.

15. The system of claim 12, wherein the instructions further cause the system to wirelessly receive, at the first rate of response, logged data from the first device coupled to the first asset within the proximity zone of the reader device, the second first rate of response being at a reduced rate compared to the second rate of response.

16. The system of claim 15, wherein the logged data wirelessly received from the first device coupled to the first asset at the first rate of response indicates an idle state of the first asset.

17. The system of claim 12, wherein the instructions further cause the system to:

detect a second device coupled to a second asset proximate to the first device coupled to the first asset; and responsive to determining that the logged data from the first device coupled to the first asset satisfies the criterion and detecting the second device coupled to the second asset proximate to the first device coupled to the first asset, trigger an alert signal to be automatically generated at the second device coupled to the second asset, wherein the alert signal further causes the second device to emit an audio/visual response.

18. The system of claim 17, wherein the first asset includes a healthcare equipment and the second asset includes a healthcare provider.

19. The system of claim 12, wherein the audio/visual response includes an instruction to move the first asset to a specific location.

20. The system of claim 12, wherein the criterion includes a sensor reading of the first asset in the logged data matching a predetermined range.

* * * * *